United States Patent [19]
Soman et al.

[11] Patent Number: 5,985,631
[45] Date of Patent: Nov. 16, 1999

[54] **METHOD FOR PREVENTING THE ACTIVATION OF INACTIVE, RECOMBINANT *HELICOBACTER PYLORI* APOUREASE**

[75] Inventors: Gopalan Soman, Belmont; William D. Thomas, Jr., Somerville; Thomas P. Monath, Harvard, all of Mass.

[73] Assignee: OraVax-Merieux Co., Cambridge, Mass.

[21] Appl. No.: 08/928,081

[22] Filed: Sep. 12, 1997

[51] Int. Cl.$^6$ .............................. C12N 9/99; C12N 9/96; C12N 9/80; A01N 37/18; C07K 1/00
[52] U.S. Cl. .................... 435/184; 435/188; 435/228; 530/404; 530/405; 514/2
[58] Field of Search .................................. 435/184, 188, 435/227, 228; 514/2; 530/350, 402, 408, 409

[56] References Cited

U.S. PATENT DOCUMENTS

| | | | |
|---|---|---|---|
| 5,538,729 | 7/1996 | Czinn et al. | 424/234.1 |
| 5,783,436 | 7/1998 | Hausinger | 435/252.3 |

FOREIGN PATENT DOCUMENTS

| | | |
|---|---|---|
| WO 94/09823 | 5/1994 | WIPO. |
| WO 95/22987 | 8/1995 | WIPO. |
| WO 96/33732 | 10/1996 | WIPO. |

OTHER PUBLICATIONS

Nagata et al. "Potent inhibitory action of the gastric proton pump inhibitor lansoprazole againest urease activity of *Helicobacter pylori*: Unique action selective for *H. pylore* cells," Atnimicrob. Agents Chemotherapy (Mar. 1993) 37(4): 769–774.
Fishbein et al. "Urease catalysis and structure," J. Biol. Chem. (Nov. 1973) 218(22): 7870–77.
Riddles et al. "Jack bean urease: VI. Determination of thiol and disulfide content; Reversible inactivation of te enzyme by the blocking of the unique cysteine residue," Biochimica Biophys. Acta (1983) 743: 115–120.
Blakely et al., "Thiolate–Nickel(II) Charge–Transfer Peaks in the Spectrum of the β–Mercaptoethanol–Urease Complex", Biochimica et Biophysica Acta, 744:219–229 (1983).
Buchner et al., "Renaturation, Purification and Characterization of Recombinant $F_{ab}$–Fragments Produced in *Escherichia Coli*", Bio/Technology, 9:157–162 (1991).
Czinn et al., "Oral Immunization against *Helicobacter pylori*", Infect Immun., 59:2359–2363 (1991).
Fágáin, "Understanding and increasing protein stability", Biochimica et Biophysica Acta, 1252:1–14 (1995).
Kühler et al., "Structure–Activity Relationship of Omeprazole and Analogues as *Helicobacter pylori* Urease Inhibitors", J. Med. Chem., 38:4906–4916 (1995).

Lee et al., "Oral Immunization with Recombinant *Helicobacter pylori* Urease Induces Secretory IgA Antibodies and Protects Mice from Challenge with *Helicobacter felis*", J. Inf. Dis., 172:161–172 (1995).
Martin et al., "Site–directed Mutagenesis of the Active Site Cysteine in *Klebsiella aerogenes* Urease", J. Biol. Chem., 267:20024–20027 (1992).
Mobley et al., "Microbial Ureases: Significance, Regulation, and Molecular Characterization", Microbiol. Rev., 53:85–108 (1989).
Mobley et al., "Molecular Biology of Microbial Ureases", Microbiol. Rev., 59:451–480 (1995).
Nagata et al., "Inhibitory Action of Lansoprazole and Its Analogs against *Helicobacter pylori*: Inhibition of Growth Is Not Related to Inhibition of Urease", Antimicrobial Agents and Chemotherapy, 39:567–570 (1995).
Nagata et al., "Growth Inhibition of *Ureaplasma urealyticum* by the Proton Pump Inhibitor Lansoprazole: Direct Attribution to Inhibition by Lansoprazole of Urease Activity and Urea–Induced ATP Synthesis in *U. urealyticum*", Antimicrobial Agents and Chemotherapy, 39:2187–2192 (1995).
Park et al., "Site–directed mutagenesis of *Klebsiella aerogenes* urease: Identification of histidine residues that appear to function in nickel ligation, substrate binding, and catalysis", Protein Science, 2:1034–1041 (1993).
Park et al., "Requirement of Carbon Dioxide for in Vitro Assembly of the Urease Nickel Metallocenter", Science, 267:1156–1158 (1995).
Pérez–Pérez et al., Effects of Cations on *Helicobacter pylori* Urease Activity, Release, and Stability, Infection and Immunity, 62:299–302 (1994).
Sriwanthana et al., "*Proteus mirabilis* Urease: Histidine 320 of UreC Is Essential for Urea Hydrolysis and Nickel Ion Binding within the Native Enzyme", Infection and Immunity, 61:2570–2577 (1993).
Todd et al., "Purification and Characterization of the Nickel–containing Multicomponent Urease from *Klebsiella aerogenes*", J. Biol. Chem., 262:5963–5967 (1987).
Todd et al., "Reactivity of the Essential Thiol of *Klebsiella aerogenes* Urease", J. Biol. Chem., 266:10260–10267 (1991).
Todd et al., "Identification of the Essential Cysteine Residue in *Klebsiella aerogenes* Urease", J. Biol. Chem., 266:24327–24331 (1991).

*Primary Examiner*—Jean C. Witz
*Assistant Examiner*—Susan Hanley
*Attorney, Agent, or Firm*—Clark & Elbing LLP

[57] ABSTRACT

A method for preventing the activation of inactive, recombinant *Helicobacter pylori* apourease is presented. The method comprises contacting the apourease with a compound that modifies a sulfhydryl or lysyl residue of the urease. The covalently modified apourease is prevented from molecular aggregation.

4 Claims, 45 Drawing Sheets

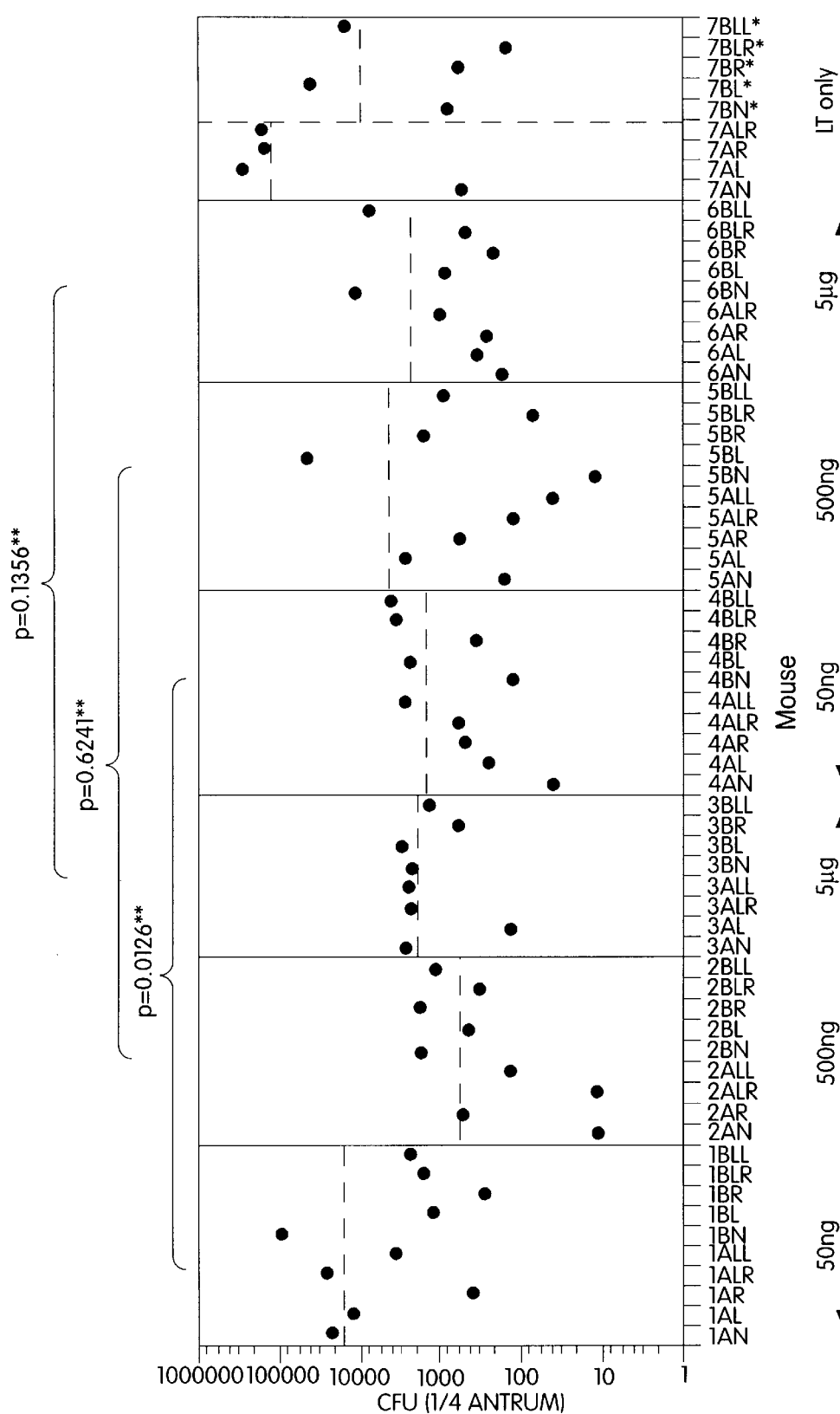

5,985,631

METHOD FOR PREVENTING THE ACTIVATION OF INACTIVE, RECOMBINANT *HELICOBACTER PYLORI* APOUREASE

BACKGROUND OF THE INVENTION

This invention relates to chemical and genetic methods for stabilizing Helicobacter urease.

*Helicobacter pylori* is a gram-negative bacterium and a gastroduodenal pathogen that causes gastritis, gastric and duodenal ulceration, and possibly gastric carcinoma in humans (Graham et al., Am. J. Gastroenterol. 82:283–286, 1987; Homick, N. Eng. J. Med. 316:1598–1600, 1987; Lee et al., Microb. Ecol. Health Dis. 1:1–16, 1988; Cover et al., Annu. Rev. Med. 40:269–285, 1989; Buck, Clin. Microbiol. Rev. 3:1–12, 1990). The bacterium produces large amounts of the enzyme urease, which is a multimeric nickel metallohydrolase that cleaves urea to ammonia and carbon dioxide (Hu et al., Infect. Immun. 58:992–998, 1990). *H. pylori* urease is localized both in the cytosol and on the extracellular surface of the bacterium (Hawtin et al., J. Gen. Microbiol. 136:1995–2000, 1990). Extracellular urease may protect the bacteria in the highly acidic stomach by hydrolyzing urea to ammonia, thereby creating a buffering cloud of ammonia that neutralizes the acid around the bacteria (Ferrero et al., Microbiol. Ecol. Health Dis. 4:121–134, 1991; Mobley et al., In *Helicobacter pylori: Basic Mechanisms to Clinical Cure*, Hunt et al. (Eds.) Kluver Acad. Pub., Dordrecht, 1994). Urease may also contribute to the pathogenicity of *H. pylori* by direct toxicity of ammonia and monochloramine to cells lining the gastric mucosa.

*H. pylori* urease is immunogenic to humans and antigenicity is highly conserved among *H. pylori* strains (Ferrero et al., Mol. Microbiol 9:323–333, 1993; Gootz et al., Infect. Immun. 62:793–798, 1994). Antigenic conservation among ureases is the basis of protection of mice against *H. felis* infection when vaccinated with *H. pylori* urease (Ferrero et al., Mol. Microbiol 9:323–333, 1993). Antigenic cross-reactivity has also been demonstrated between *H. pylori* and *H. mustelae* ureases (Gootz et al., Infect. Immun. 62:793–798, 1994).

Urease enzymatic activity is toxic to animals and humans (Thomson et al., Am. J. Med. 35:804–812, 1963; Mobley et al., Microbiol. Rev. 53:85–108, 1985; LeVeen et al., Biomed. Pharmacother. 48(3–4):157–166, 1994). Anti-urease antibodies bind to urease, but generally do not inhibit urease enzymatic activity. For example, there is one report that claims to show inhibition of urease activity by monoclonal antibodies to urease (Nagata et al., Infect. Immun. 60:4826–4831, 1992). We tested monoclonal and polyclonal antibodies to urease and urease subunits, and found no inhibition of urease activity. Thomas et al. (J. Clin. Microbiol. 30:1338–1340) measured urease inhibitory activity in serum samples from children infected with *H. pylori*, and found that among thirteen serum samples showing urease binding activity, only one sample showed any urease inhibitory activity. These observations show that the catalytic and immunogenic domains of urease are different. This is further supported by a recent report that antigenic reactivity of a urease preparation was retained under storage conditions in which enzymatic activity was lost (Perez-Perez, Infect. Immun. 62:299–302, 1994). These results suggest that immunogenicity can be separated from potentially toxic enzymatic activity, which is an important characteristic of a potential vaccine.

Specific human antibody responses to urease are absent or weak in a high proportion, if not the majority, of infected individuals. Antibodies to urease administered to animals together with live Helicobacter protect against infection (Blanchard et al., Infect. Immun. 63:1394–1395, 1995). Together, these observations support the basis for the effectiveness of urease as a vaccine that induces a high-grade, urease-specific immune response protective against *H. pylori*.

Nine genes have been identified in the *H. pylori* urease gene cluster (Cussac et al., J. Bacteriol. 174:2466–2473, 1992; Labigne et al., J. Bacteriol. 173:1920–193, 1992). These include the urease structural genes, encoding UreA and UreB, and the accessory genes, encoding Ure I, E, F, G, and H. These genes have been shown to be essential for urease activity. Hu et al. (Infect. Immun. 60:2657–2666, 1992) expressed genes encoding the UreA and UreB subunits of *H. pylori* urease in *E. coli* and showed that these two genes alone are sufficient to encode a fully assembled apoenzyme, which was structurally and immunologically identical to native urease, but catalytically inactive, due to the absence of nickel ions. Addition of nickel ions alone did not restore catalytic activity. Similar results were reported with other bacterial ureases. In other studies, recombinant *Klebsiella aerogenes* apourease, which differs substantially from *H. pylori* urease in subunit structure and overall amino acid sequence, was shown to be activated in vitro by incubation with carbon dioxide or bicarbonate, together with nickel ions (Park et al., Science 267:1156–1158, 1995). Based on crystallographic analysis, the *K. aerogenes* urease bi-nickel center is thought to include His 272, His 246, His 136, His 134, Asp 360, and Lys 219 of the Ure C subunit. By analogy, the *H. pylori* urease metallocenter may be described as including His 248, His 138, His 136, Asp 362, and Lys 219 of the Ure B subunit.

SUMMARY OF THE INVENTION

We have shown that treatment of Helicobacter urease with compounds that chemically modify urease amino acids can prevent in vitro activation of urease, as well as molecular aggregation of urease. We have also shown that including amino acid substitutions in urease can prevent in vitro activation of urease.

Accordingly, in one aspect, the invention features methods of stabilizing Helicobacter (e.g., *H. pylori*) urease. In these methods, urease (e.g., recombinant or native urease) is contacted with a compound that modifies an amino acid of the urease. Stabilization of urease according to the invention can prevent activation of the urease, or prevent molecular aggregation of the urease.

Compounds used in these methods can be, for example, sulfhydryl-reactive compounds. For example, iodoacetamide (IAM), iodoacetic acid (IAA), 5-5'-dithio-bis-2-nitrobenzoic acid (DTNB), 2,2'-dithiodipyridine (DTDP), cystine, cystamine, methyl methanethiolsulfonate (MMTS), N-ethyl maleimide (NEM), dinitrofluorobenzene (DNFB), or trinitrobenzene sulfonic acid (TNBSA) can be used. Additional compounds that can be used in the invention are described further below.

Also included in the invention are Helicobacter (e.g., *H. pylori*) urease polypeptides, for example, recombinant or native urease polypeptides, that have been stabilized by any of the methods described above. The stabilized urease polypeptides can be present in a pharmaceutically acceptable carrier or diluent.

In another aspect, the invention provides Helicobacter (e.g., *H. pylori*) urease polypeptides having an amino acid mutation (or mutations) that prevents activation of the urease polypeptides. For example, the urease polypeptides can contain an amino acid mutation in urease amino acid histidine 136, histidine 248, or lysine 219 in UreB. The urease polypeptides having such a mutation can be present in a pharmaceutically acceptable carrier or diluent.

Also included in the invention are methods of inducing an immune response to Helicobacter in a patient. In these methods, one of the urease polypeptides described above is administered to a patient that is at risk of developing, but does not have, Helicobacter infection, or to a patient that has Helicobacter infection. The urease polypeptide can be administered to a mucosal surface of the patient, or it can be administered parenterally, e.g., by intravenous, intramuscular, or percutaneous administration.

As used herein, a polypeptide, such as a Helicobacter urease polypeptide, is said to be "stabilized" if it has been treated or modified so that it maintains its molecular structure, to a degree sufficient to retain immunogenicity. Urease that has been treated with a compound, e.g., iodoacetamide (IAM), 5,5'-dithiobis(2-nitrobenzoic acid) (DTNB), N-ethyl maleimide (NEM), or dinitrofluorobenzene (DNFB), so that it is prevented from the molecular aggregation or activation (e.g., in vitro activation) characteristic of untreated urease (see below) is said to be "stabilized." The term "urease," as used herein, includes urease polypeptides that have been purified from an organism, such as a bacterium from the genus Helicobacter (e.g., a bacterium of the species $H.$ $pylori$), fragments of purified urease, as well as urease polypeptides (e.g., urease apoenzyme), urease subunits (e.g., UreA and UreB subunits), and urease fragments produced using recombinant or chemical synthetic methods.

The invention provides several advantages. For example, maintenance of urease in a stable molecular form can contribute to consistency in the results of methods employing urease, such as prophylactic, therapeutic, and diagnostic methods. In addition, because activated urease has been shown to be toxic in cell culture assays, animals, and humans (Thomson et al., Am. J. Med. 35:804–812, 1963; Mobley et aL, Microbiol. Rev. 53:85–108, 1985; LeVeen et aL, Biomed. Pharmacother. 48(3–4):157–166, 1994) prevention of urease activation enables production of a safer urease product for use in prophylactic and therapeutic methods.

Other features and advantages of the invention will be apparent from the detailed description, the drawings, and the claims.

Figure 1:
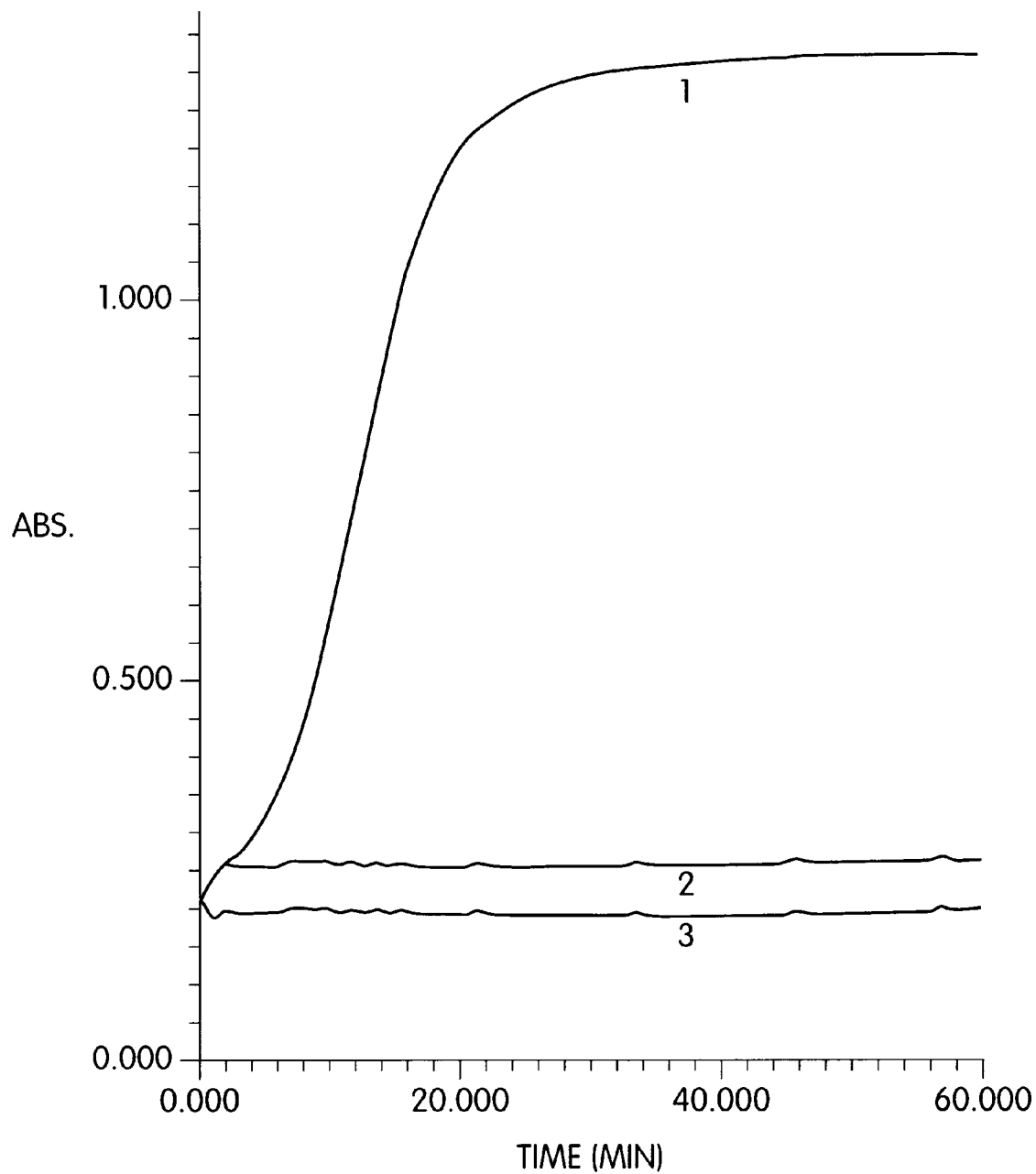
FIG. 1 is a graph showing the activation of recombinant $H.$ $pylori$ urease by nickel ions and bicarbonate. Urease that was freeze-dried in 2% sucrose was reconstituted in water to a concentration of 4.0 mg/ml in 2% sucrose. Reconstituted urease was mixed with an equal volume of HEPES (0.1 M), NaCl (0.3 M), EDTA (1 mM) buffer, with or without sodium bicarbonate and/or $Ni^{++}$ ions. The sample (1) incubation mixture contained 0.2 M sodium bicarbonate and 200 µM $Ni^{++}$, the sample (2) incubation mixture contained 0.2 M sodium bicarbonate and no $Ni^{++}$, and the sample (3) incubation mixture contained 200 µM $Ni^{++}$ and no bicarbonate. All of the samples were incubated for 40 minutes at 37° C. and were then assayed for urease activity using the urease-broth assay. Twenty µl of each sample were added to 1 ml of urease broth, mixed well, and immediately scanned at 550 nm to monitor the pH-dependent deprotonation of phenol red to produce pink colored phenolate anion. Time course scanning was carried out in a Shimadzu model UV-1 PC spectrophotometer using a CPM 260 multi-channel cuvette holder. The scans were normalized for zero time correction.

for 1 hour and 53 minutes with activation buffer containing 200 mM bicarbonate and 200 μM $Ni^{++}$. The samples were then separated by 6% native PAGE and stained for urease activity by urease-specific silver staining. Conditions used for the samples fractionated in each of the lanes of the gel are as follows: lane 1, 25 mM imidazole; lane 2, 12.5 mM imidazole; lane 3, 5 mM imidazole; lane 4, 0.5 mM imidazole; lane 5, urease incubated with 5 mM $MgCl_2$, but no $Ni^{++}$. Lane 6 contains jack bean urease.

Figure 16A:
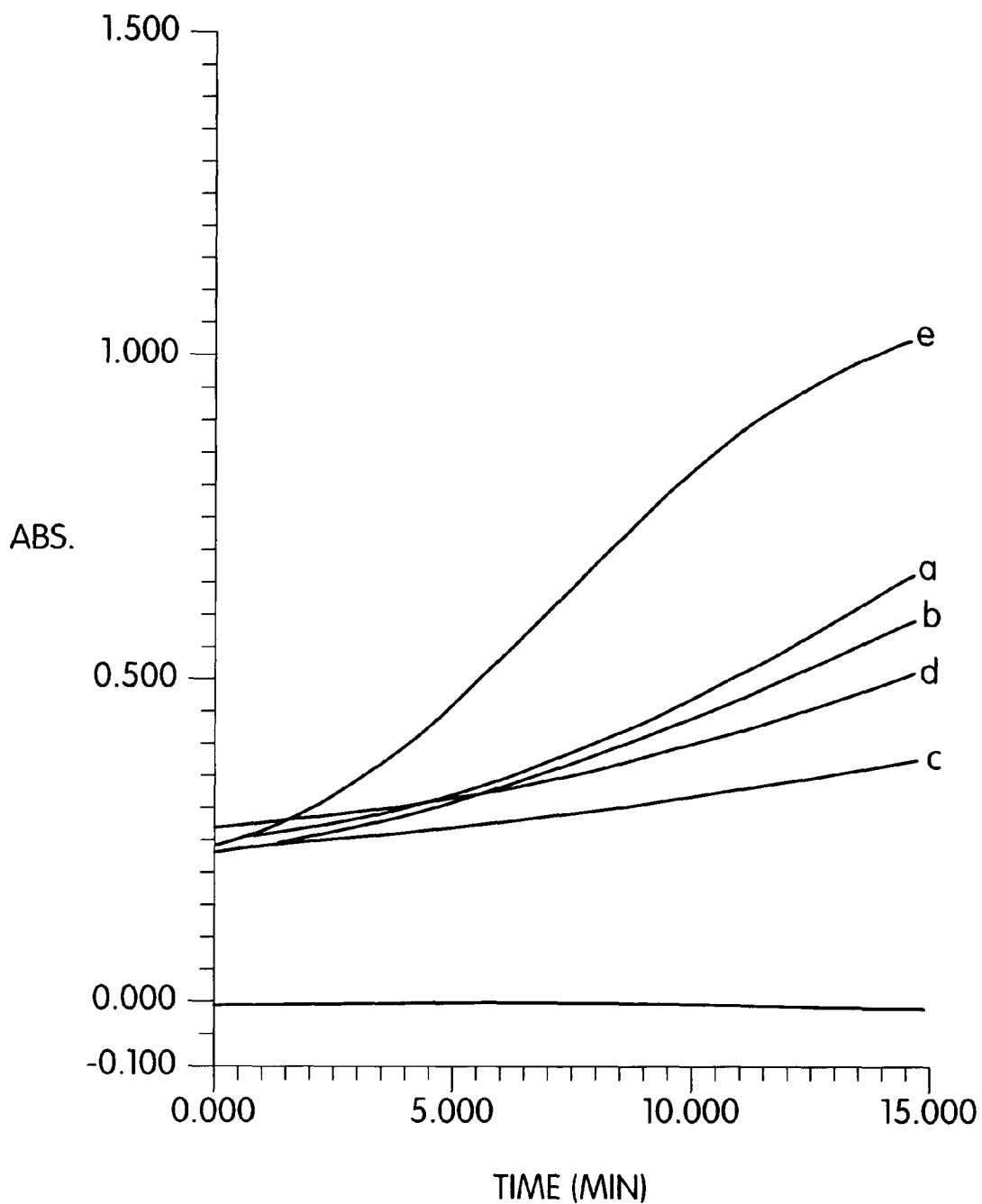

FIG. 16A is a graph showing that chemical modification of recombinant H. pylori apourease with iodoacetamide inhibits activation of urease with nickel ions and bicarbonate. Iodoacetamide was added to a recombinant urease solution (4 mg/ml) to a final concentration of 1 mM and incubated at room temperature (Ure-IAA). At time zero, 100 μl of the Ure-IAA was mixed with 100 μl of urease activation buffer and incubated at 37° C. (a). At five minutes, 250 μl of the (Ure-IAA) was transferred to a Macrosep 100 filter centrifuge, 5 ml of 2% sucrose was added, and the sample was concentrated to approximately 250 μl. The process of diafiltration was carried out two more times by adding 5 ml of 2% sucrose and concentrating the sample down to 250 μl. One hundred μl of sample was mixed with 100 μl of urease activation buffer, and the mixture was incubated at 37° C. for 1 hour (b). After 60 minutes of incubation at room temperature, 100 μl of the Ure-IAA mixture was mixed with 100 μl of urease activation buffer and incubated for 1 hour at 37° C. (c). At the 60 minute time point, 250 μl of the Ure-IAA mixture was diafiltered in 2% sucrose using the Macrosep 100, as described for sample b. One hundred μl of the diafiltered material was mixed with 100 μl of urease activation buffer and incubated for 37° C. for 1 hour (d). Untreated urease (100 μl) was mixed with 100 μl of urease activation buffer and incubated for 1 hour at 37° C. (e). At the end of 1 hour of incubation of the urease in activation buffer, 10 μl was added to 1 ml of urea broth and the urease activity was monitored by following the increase in absorption at 550 nm.

Figure 16B:
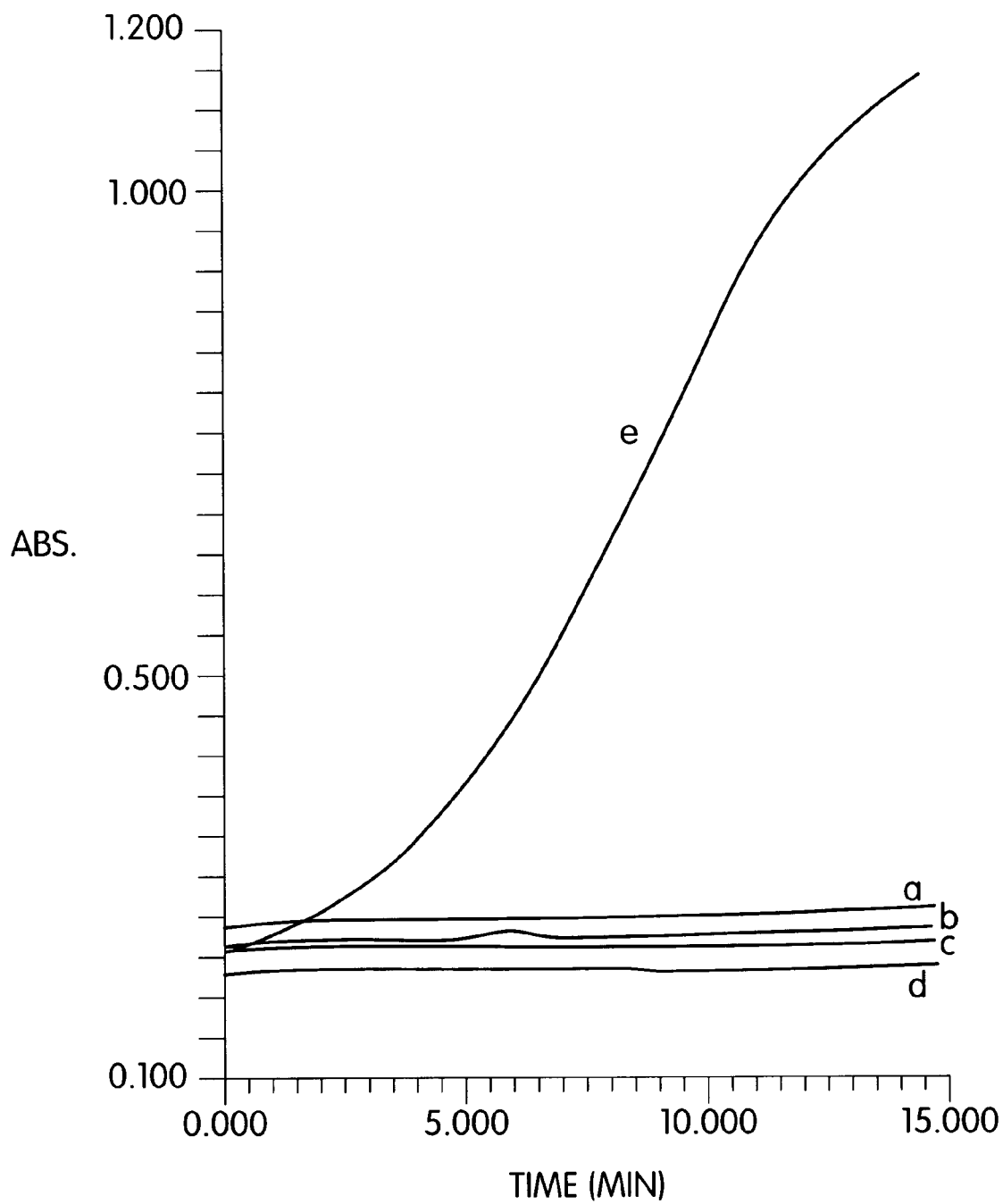

FIG. 16B is a graph showing the results of the same experiments as those described above for FIG. 16A, except that recombinant H. pylori urease was treated with DTNB (50 μl of DTNB (5 mg/ml) was mixed with 1 ml urease (4 mg/ml)). Samples a–e were treated exactly the same way as described for the Ure-IAA mixture described above for FIG. 16A.

Figure 17A:
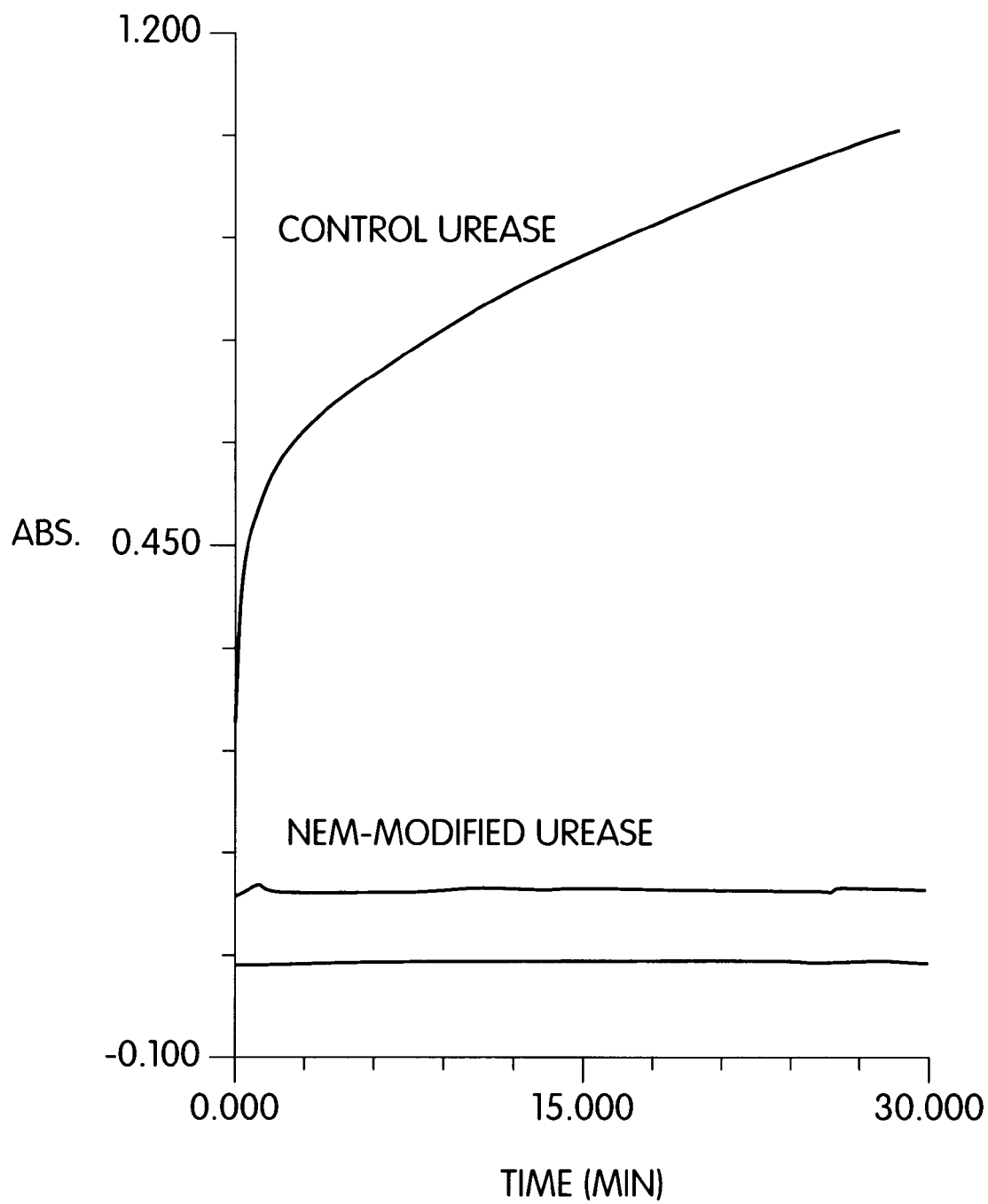

FIG. 17A is a graph showing the effect of N-ethyl maleimide on the sulfhydryl reactivity and in vitro activation of recombinant apourease. Recombinant apourease (3–4 mg/ml) in 20 mM Hepes buffer-2% sucrose (pH 7.5) was incubated with 9 mM NEM for 60 minutes at room temperature. After incubation, excess reagent was removed by dialysis against 20 mM HEPES-2% sucrose at 2–8° C. The untreated urease was processed similarly. After dialysis, the DTNB-reactive sulfhydryl groups were analyzed. Urease samples were incubated with 0.3 mM DTNB solution and the absorbance increase at 412 nm was monitored.

Figure 17B:
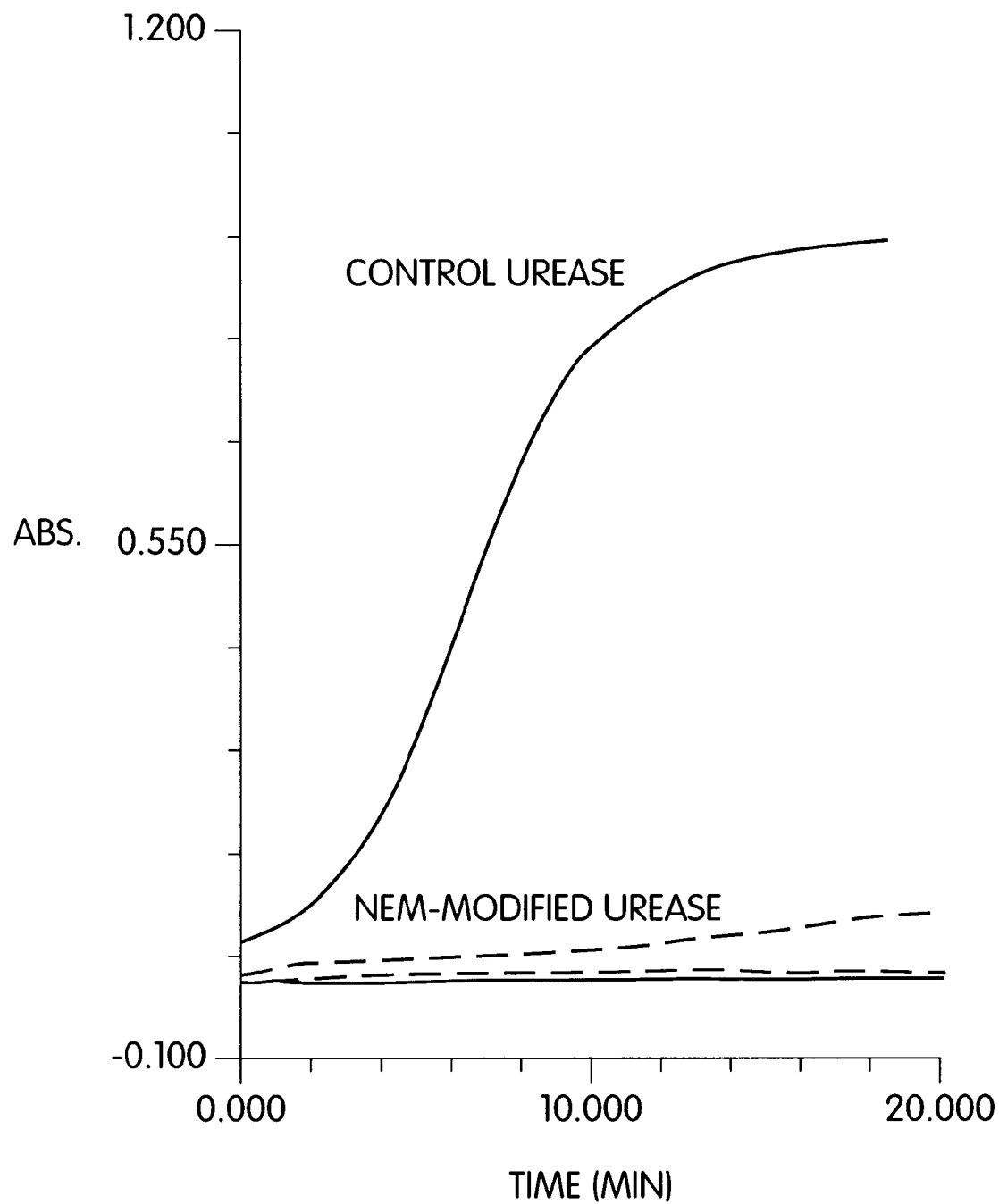

FIG. 17B is a graph showing measurements of enzymatic activity of modified and control urease (see description of FIG. 17A) incubated with bicarbonate/$Ni^{++}$ reagent using phenol broth, as described in above in reference to FIG. 1.

Figure 18A:
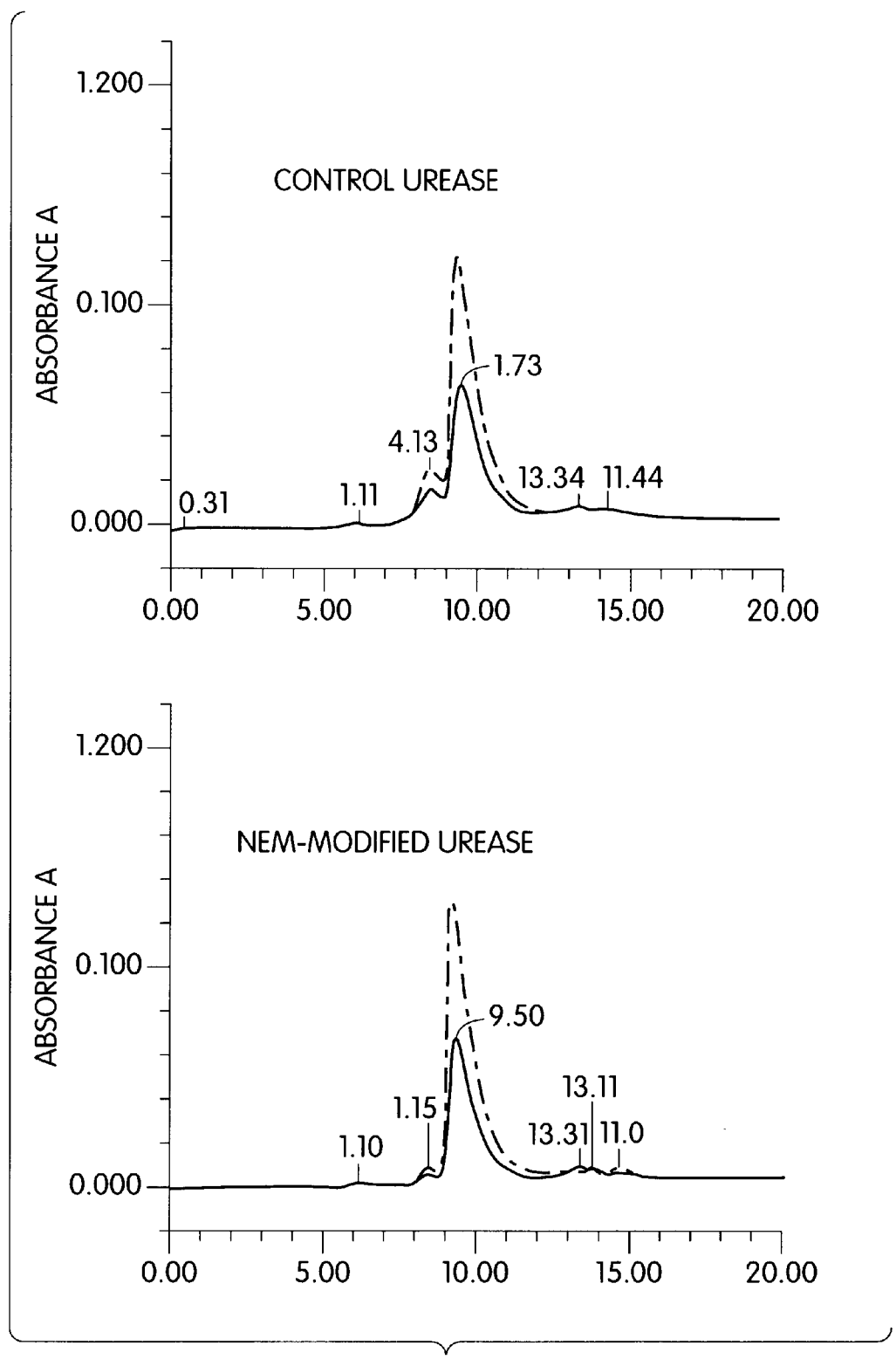

FIG. 18A is a set of graphs showing the effect of NEM treatment on the molecular stability of recombinant Helicobacter apourease, as studied by analytical size-exclusion HPLC on a progel TSK-4000 column (5 mm×30 cm id) with GSXL guard column. Chromatography was carried out immediately after modification and dialysis.

Figure 18B:
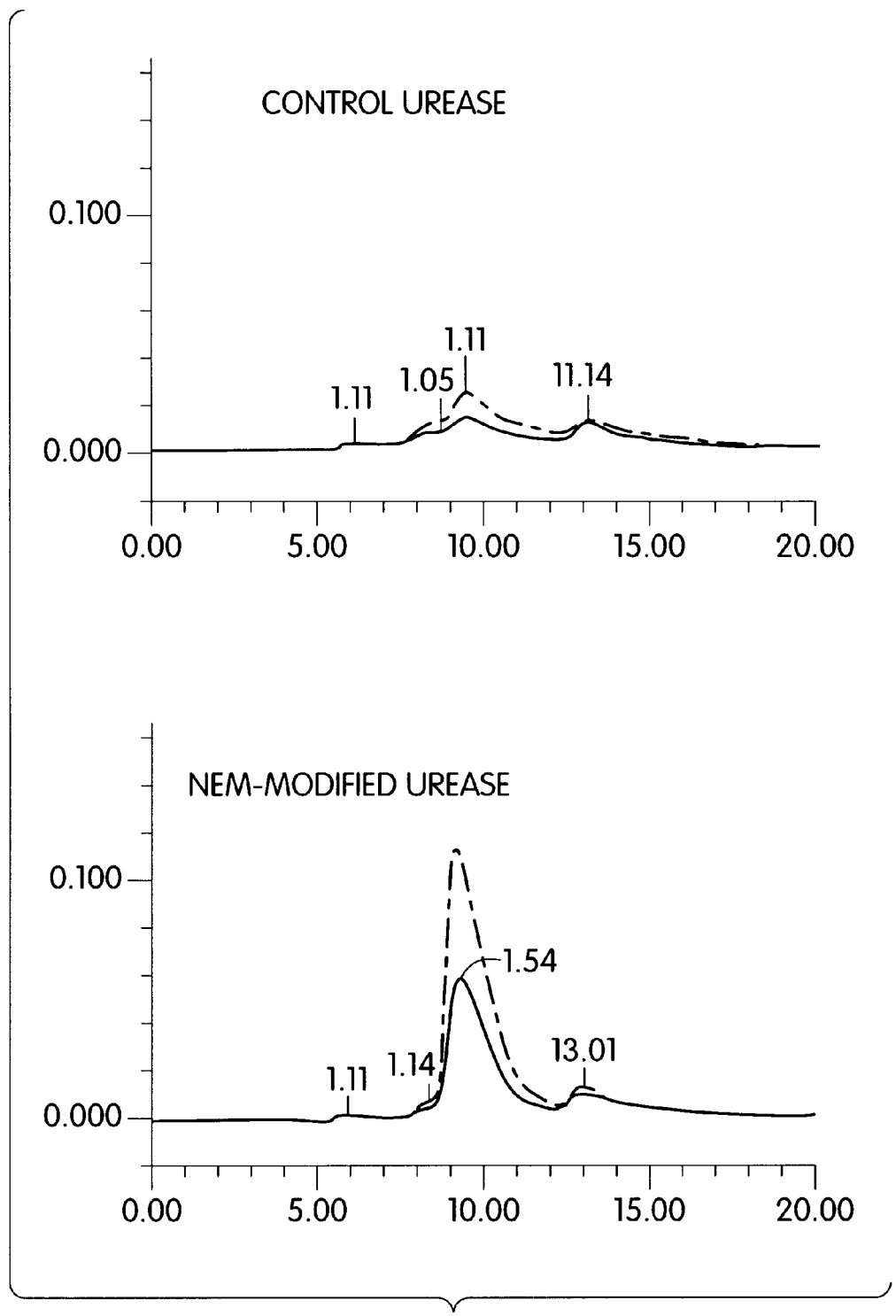

FIG. 18B is a set of graphs showing the effect of NEM treatment on the molecular stability of recombinant Helicobacter apourease, as studied by analytical size-exclusion HPLC on a progel TSK-4000 column (5 mm×30 cm id) with a GSXL guard column. Chromatography of the modified, dialyzed sample was carried out after 15 days of storage at 2–8° C.

Figure 19A:
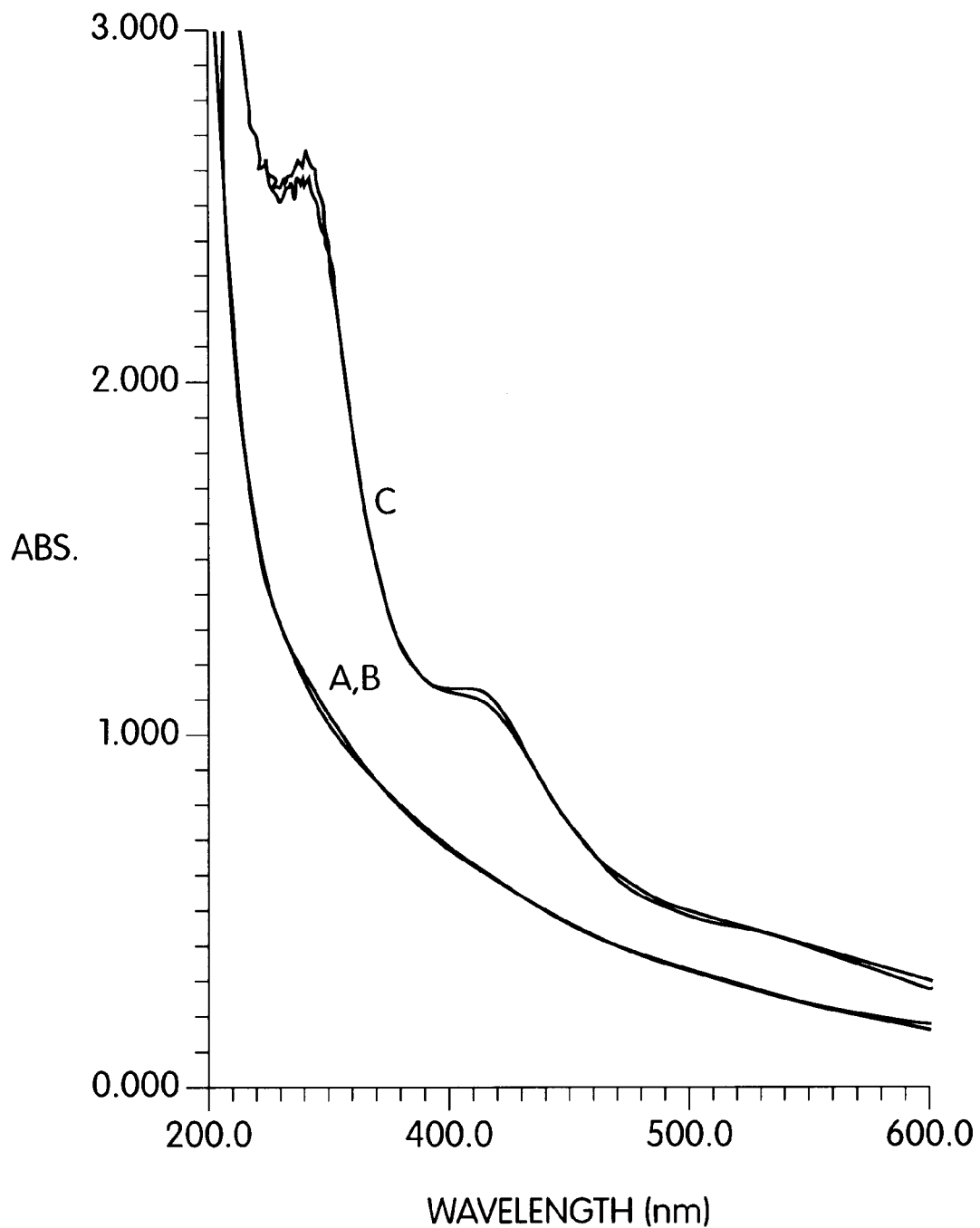

FIG. 19A is a graph showing that β-mercaptoethanol perturbs the UV-visible absorption spectrum of activated recombinant H. pylori urease. Recombinant H. pylori urease was activated by incubation in 100 mM HEPES, 1 mM EDTA, 0.3 M NaCl, 200 mM sodium bicarbonate, and 1 mM $Ni^{++}$. After 1 hour of incubation at 37° C., the unbound $Ni^{++}$ and bicarbonate were removed by dialysis over two changes of 2% sucrose for 24 hours at 4° C. The absorption spectrum is shown in the graph, and was recorded on a Shimadzu model UV2101 PC spectrophotometer. Spectrum (a) was recorded in the absence of β-mercaptoethanol, spectrum (b) was recorded in the presence of 1 mM β-mercaptoethanol, and spectrum (c) was recorded in the presence of 10 mM β-mercaptoethanol.

Figure 19B:
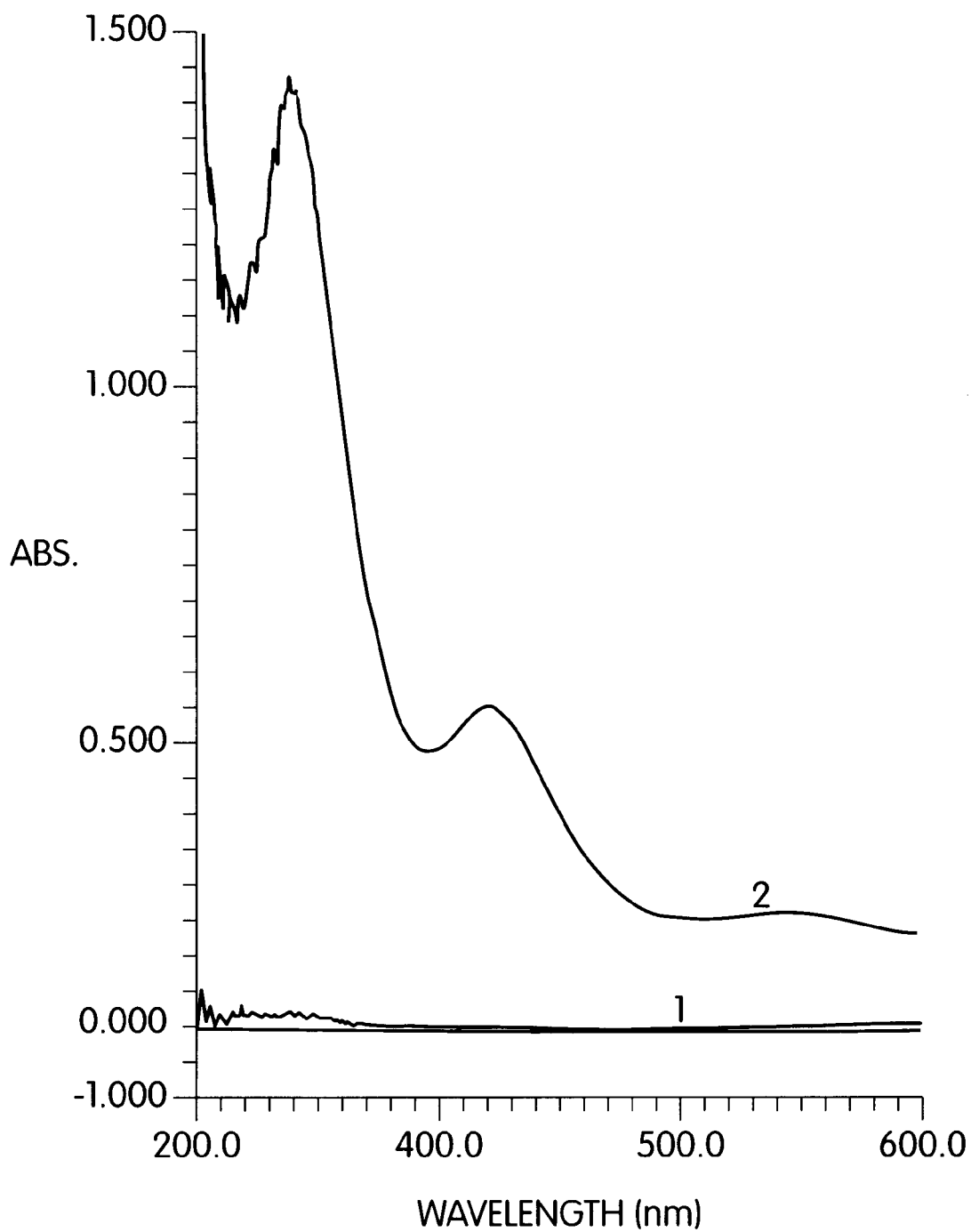

FIG. 19B is a graph showing the difference spectrum of activated urease in the presence and absence of β-mercaptoethanol. Curve (1) is spectrum (b)-spectrum (a), and curve (2) is spectrum (c)-spectrum (a).

Figure 20A:
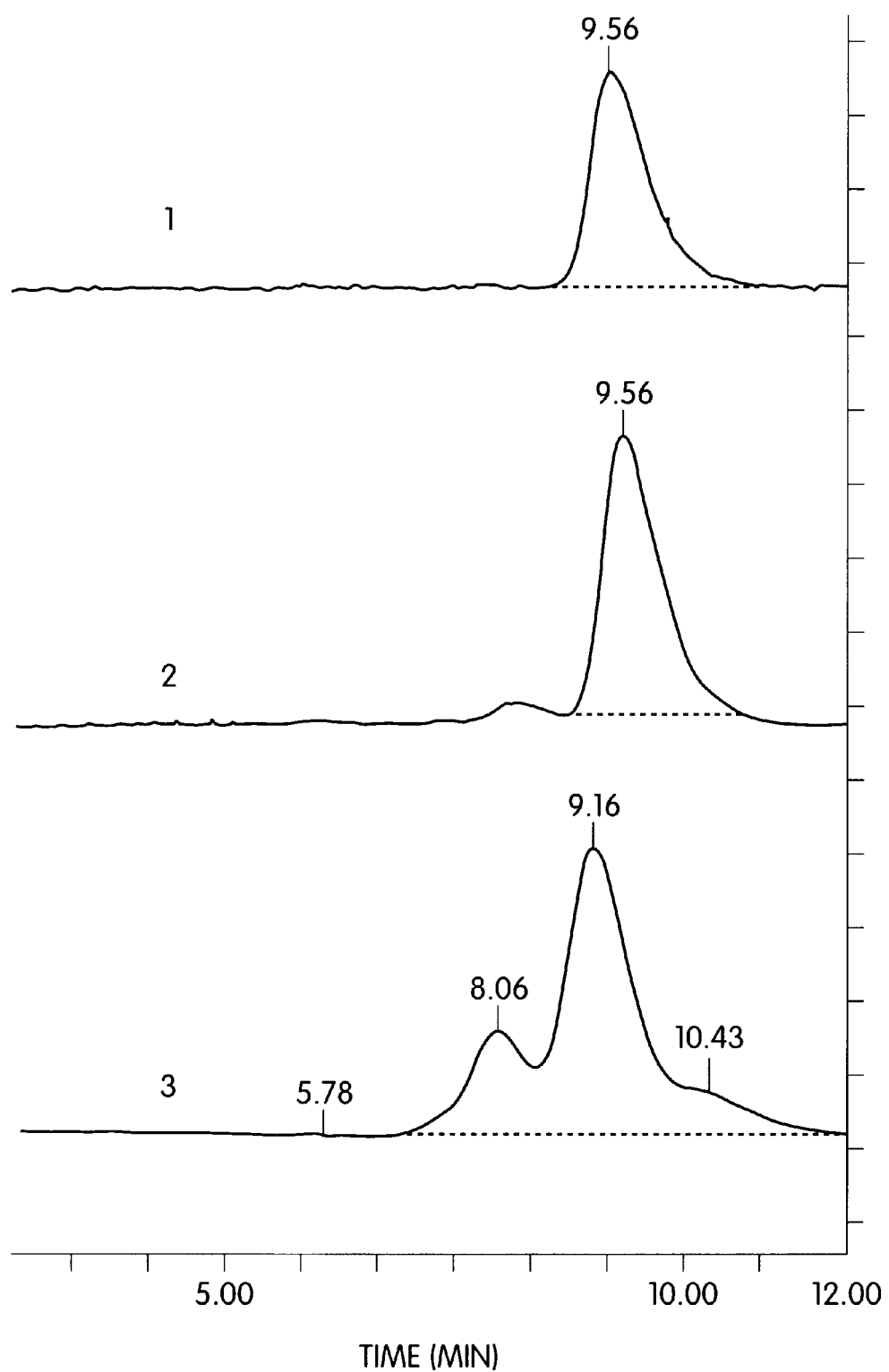

FIG. 20A is a series of graphs showing a comparison of the properties of (1) native H. pylori urease dialyzed in PBS, (2) native H. pylori urease dialyzed in 50% glycerol, and (3) recombinant urease dialyzed in 50% glycerol, as analyzed by analytical size exclusion HPLC on a Progel TSK-4000 column (5 mm×30 cm id) with a GSXL guard column. Recombinant urease from E. coli strain ORV214 and native H. pylori urease from the H. pylori strain CPM 630 were purified as is described further below. The purified urease was dialyzed against 10 mM phosphate, 0.15 M NaCl (pH 7.4), with or without 50% glycerol.

Figure 20B:
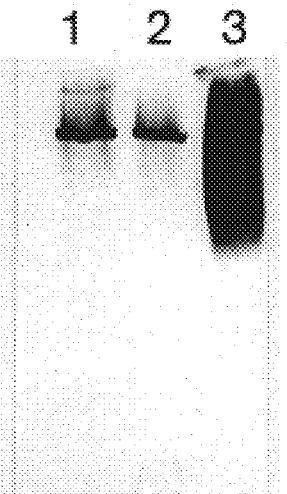

FIG. 20B is a photograph of native PAGE and Western blot analysis of the three samples described above for FIG. 20A using antibody MPA3.

Figure 20C:
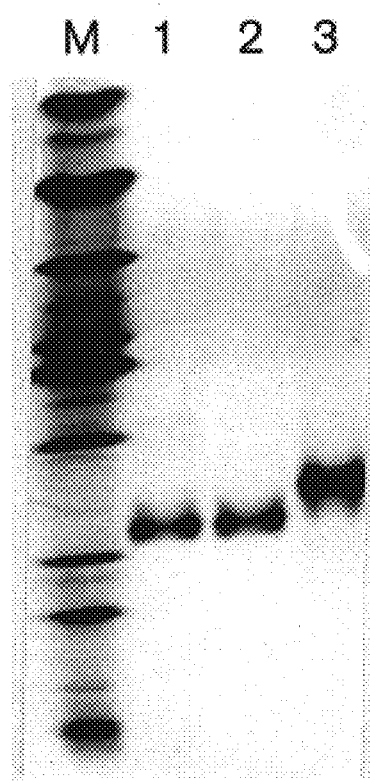

FIG. 20C is a photograph of isoelectric focusing analysis of the three samples described above for FIG. 20A, carried out in a 5% polyacrylamide gel (pH 3–10).

Figure 21A:
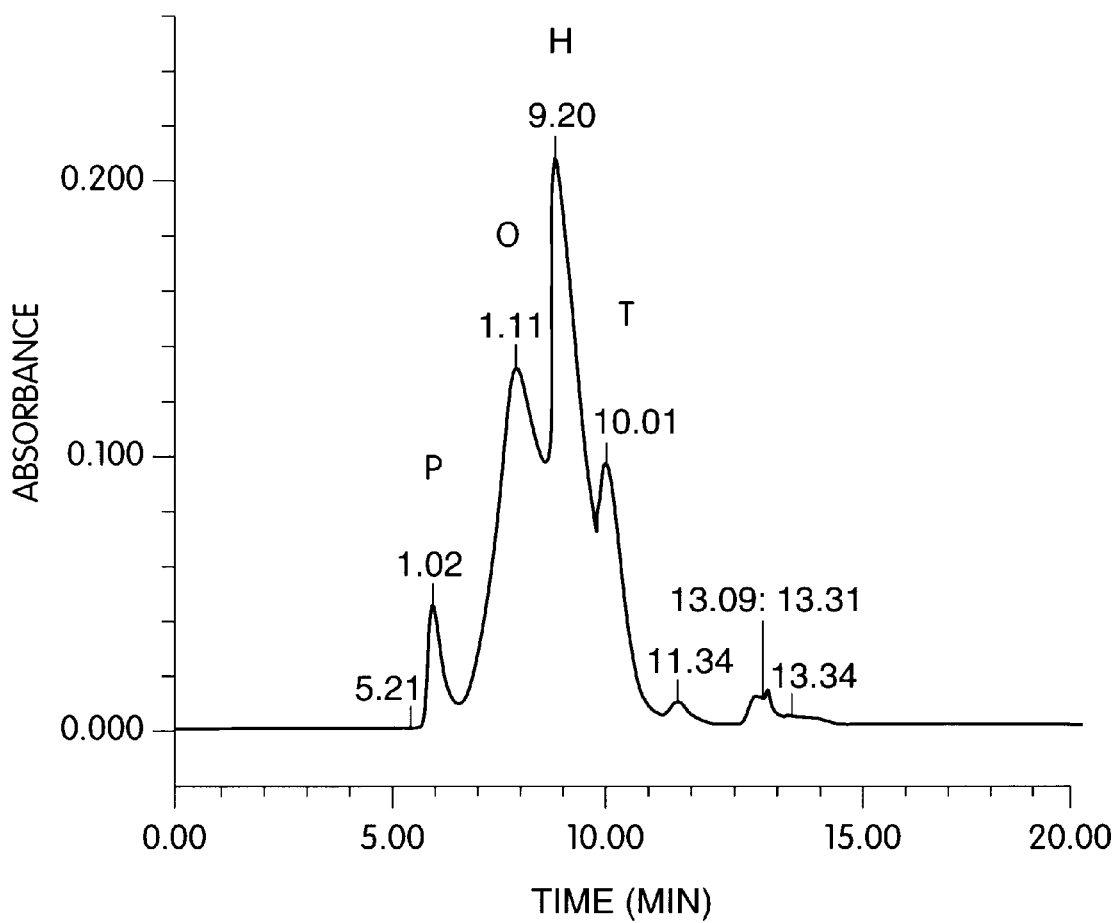

FIG. 21A is a graph showing the isolation and characterization of four different forms of urease separated by analytical size exclusion HPLC. Recombinant urease solution was stored at 4° C. for 2–3 weeks. The different molecular forms of urease were separated by analytical size exclusion HPLC on a Progel-TSK 4000 SW×L column. The individual peaks were collected and analyzed. The different peaks are labeled as follows: P—high molecular weight polymeric urease (lower retention time in HPLC), O—octomeric urease, H—hexameric urease, and T—tetrameric urease.

Figure 21B:
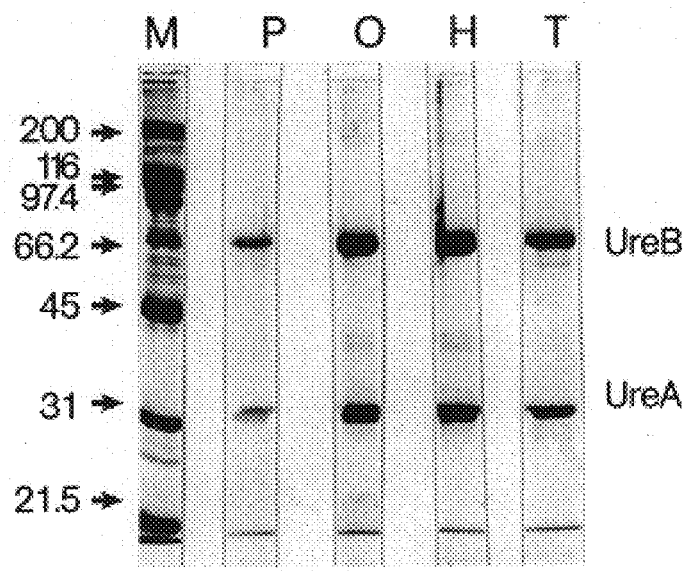

FIG. 21B is a photograph of reducing SDS-PAGE and Coomassie staining analysis of the different molecular forms of urease separated by analytical size exclusion HPLC, as described above for FIG. 21A.

Figure 21C:
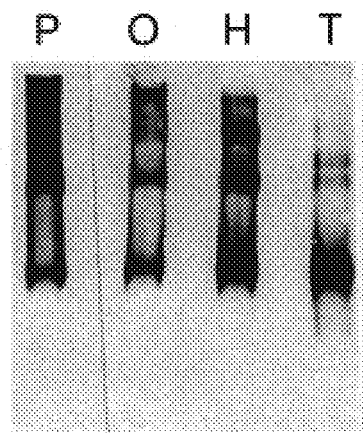

FIG. 21C is a photograph of native PAGE and immunoblot analysis of the different molecular forms of urease separated by analytical size exclusion HPLC, as described above for FIG. 21A using MPA3.

Figure 21D:
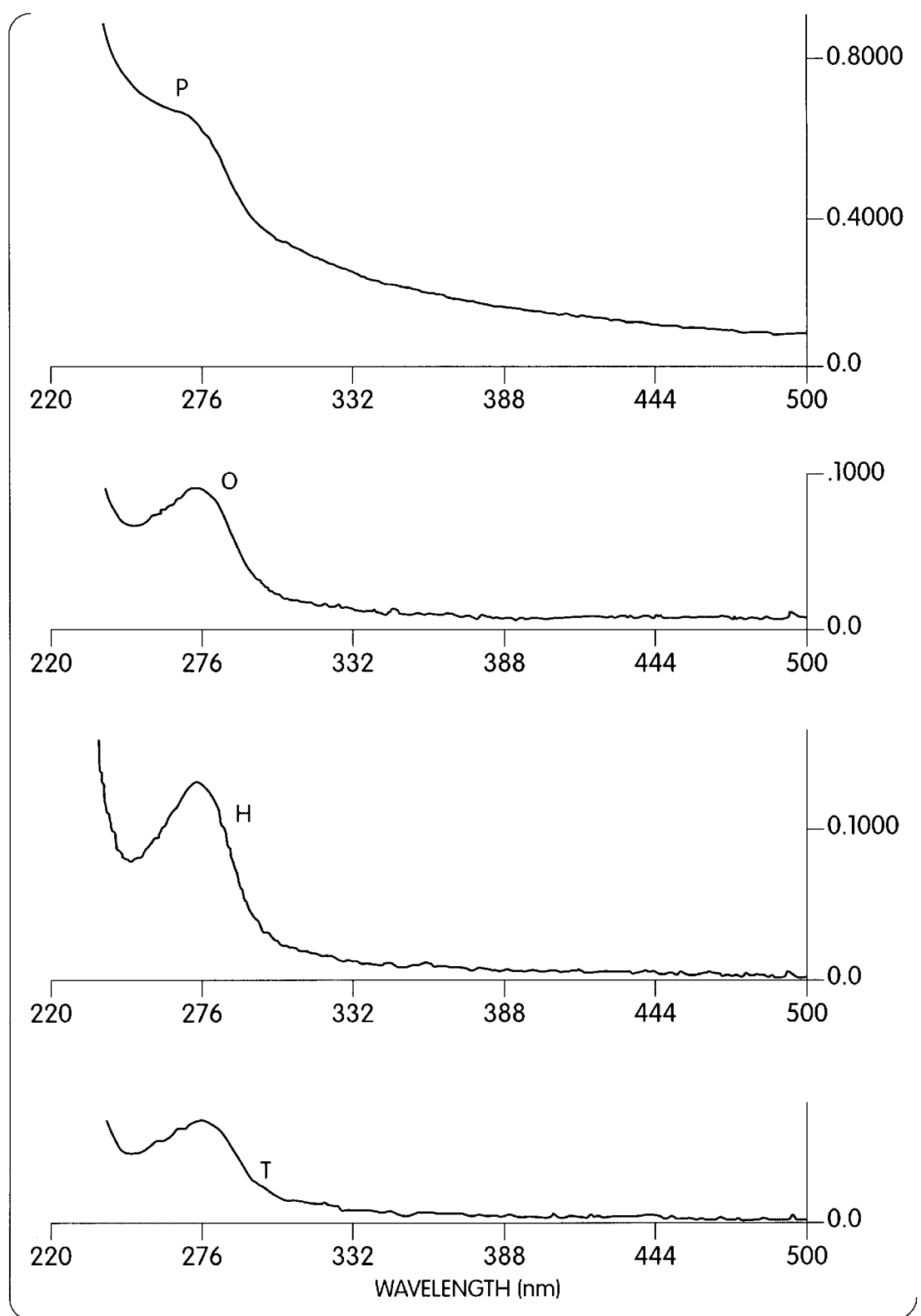

FIG. 21D is a UV-Visible absorption spectrum of the different molecular forms of urease separated by analytical size exclusion HPLC, as described above for FIG. 21A.

Figure 22A:
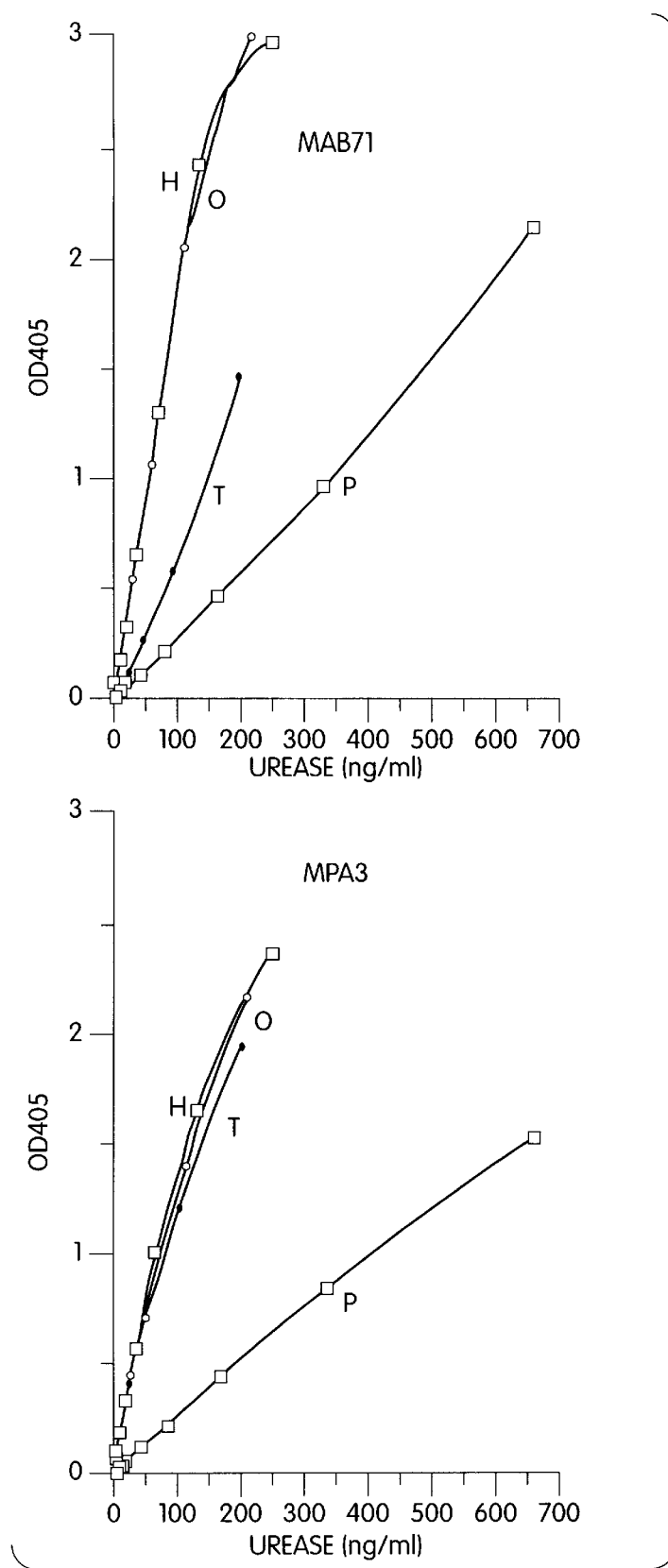

FIG. 22A is a set of graphs showing the ELISA reactivity of different forms of urease, isolated as described above for FIG. 21A, with MPA3 and MAB71.

Figure 22B:
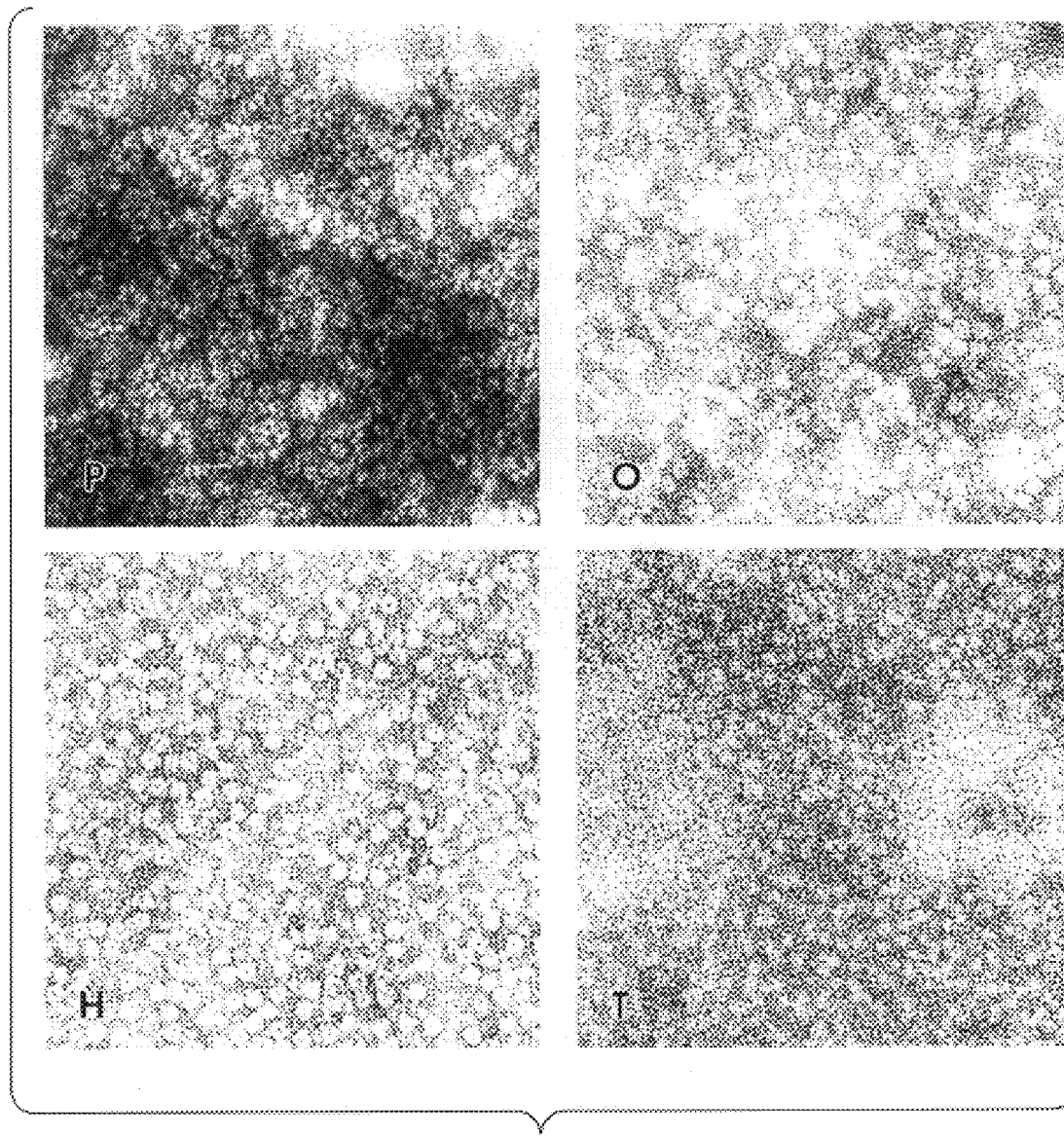

FIG. 22B is a photograph of electron microscopic analysis of different forms of recombinant urease. The different forms of urease were isolated as described above for FIG. 21A. The different forms are labeled as follows: P—polymeric urease, O—octomeric urease, H—hexameric urease, and T—tetrameric urease. Experimental details are described below in analytical methods (page 51, lines 13–17).

Figure 23A:
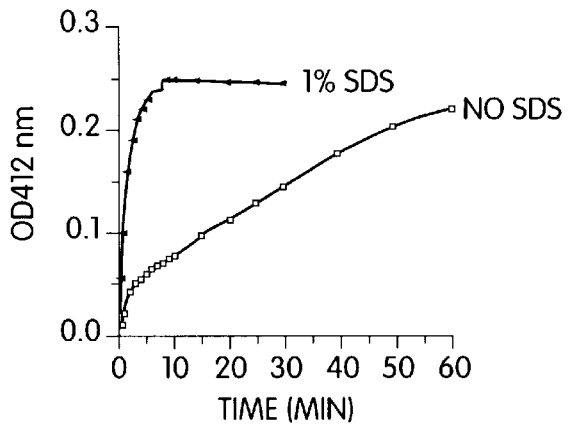

FIG. 23A is a graph showing the effect of SDS on the SH group reactivity in a titration of sulfhydryl groups of recombinant urease. Recombinant urease (4.0 mg/ml) was titrated with DTNB (1 mM) in 100 mM Tris-HCl (pH 8.0) in the absence or presence of 1% SDS. The absorbance at 412 nm is plotted against the time of the reaction.

Figure 23B:
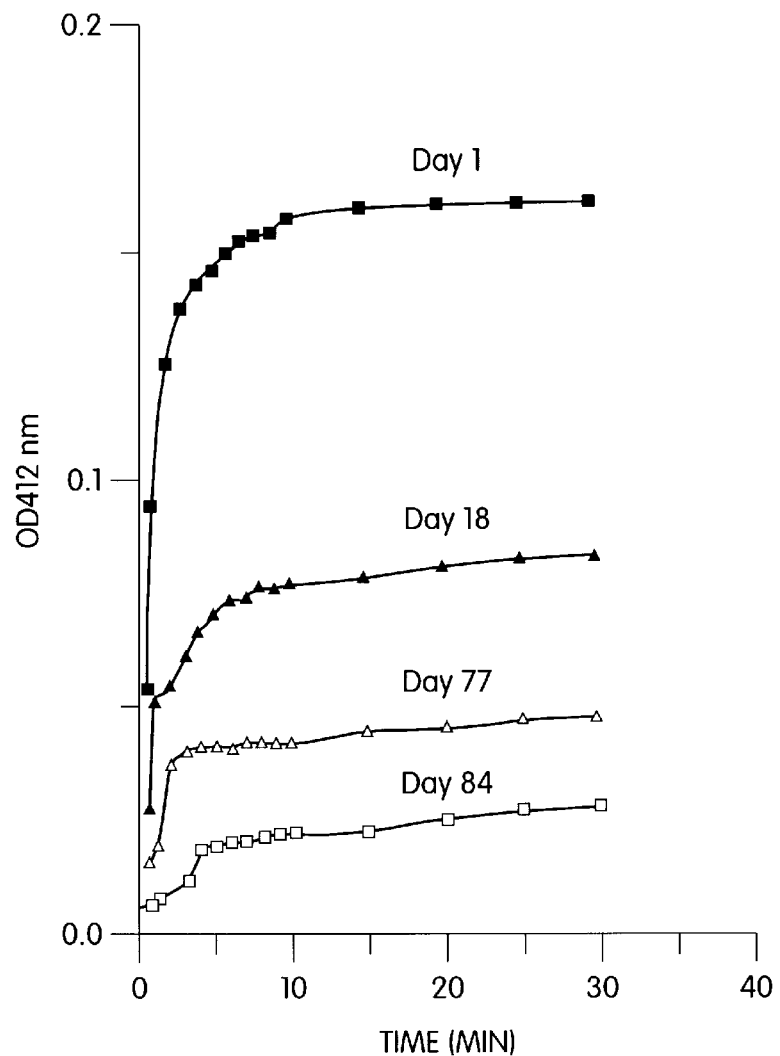

FIG. 23B is a graph showing the effect of storage time on the SH group reactivity in a titration of sulfhydryl groups of recombinant urease. Recombinant urease in 2% sucrose was stored at 4° C. for different periods of time. The DTNB titration was performed in the presence of 1% SDS, as described above.

Figure 23C:
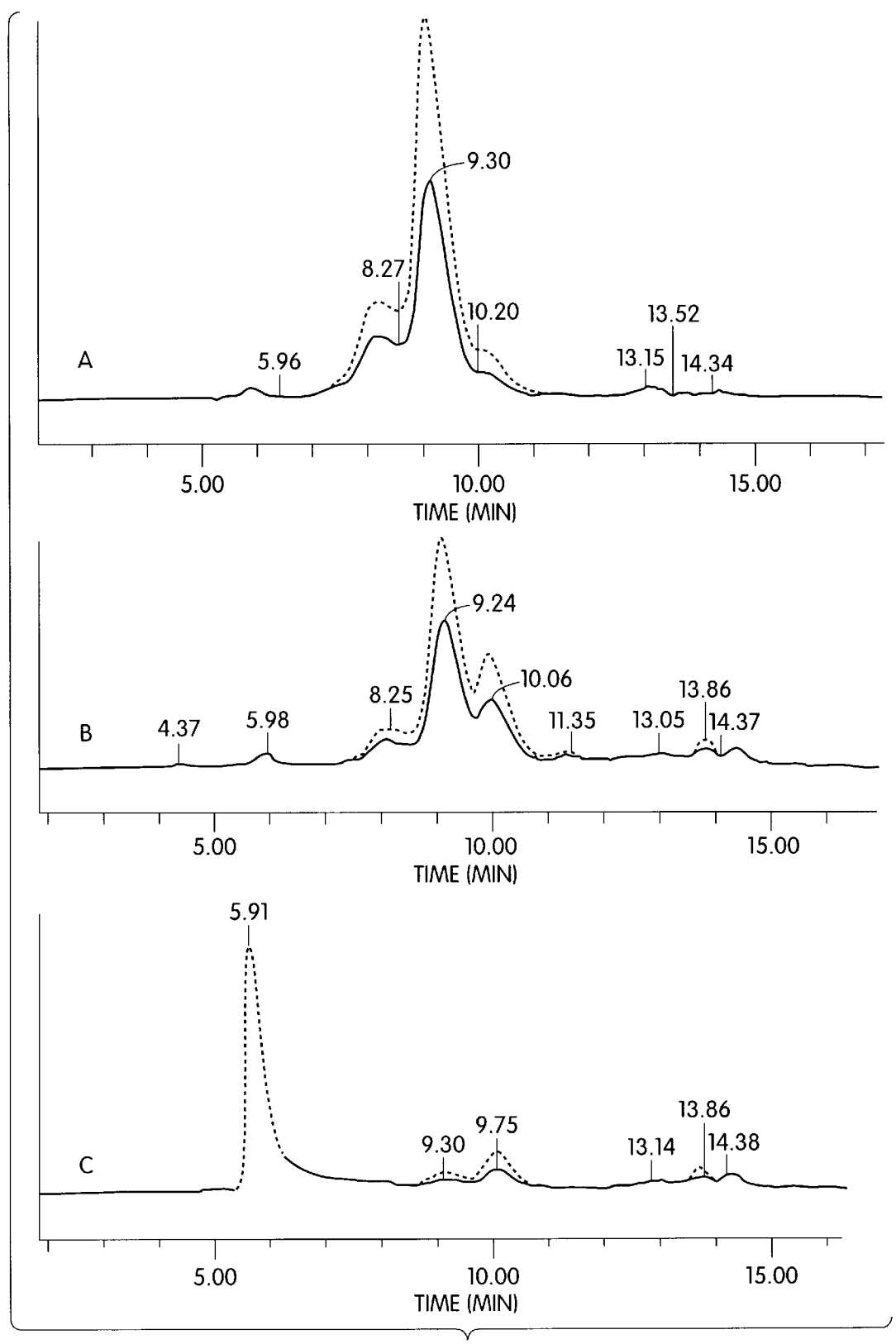

FIG. 23C is a set of graphs showing the effect of DTNB treatment on the molecular state of urease, as analyzed by analytical size exclusion HPLC. Recombinant urease (4.0 mg/ml) in 100 mM Tris (pH 8.0) was incubated with 1 mM DTNB for 1 hour at room temperature. The DTNB-treated and control samples were then dialyzed against phosphate buffered saline (pH 7.4) for 12–24 hours. Samples were subsequently stored at 4° C. for 48 hours, and then analyzed by HPLC. The samples used in the experiments shown in the three graphs are as follows: (a) recombinant urease solution in 2% sucrose, (b) DTNB-treated and dialyzed (PBS) urease, and (c) control urease dialyzed in PBS.

Figure 24A:
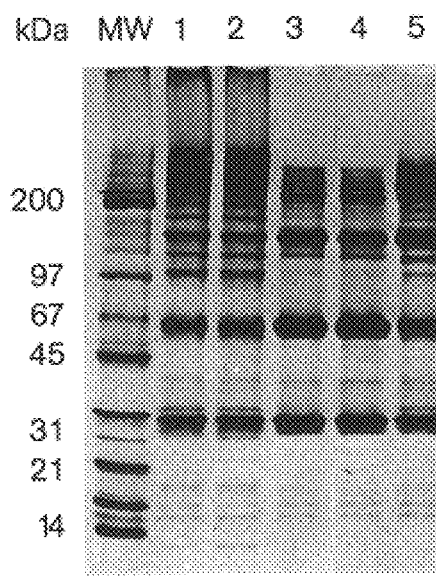

FIG. 24A is a photograph of reducing SDS-PAGE and Coomassie staining analysis showing the effect of storage time and SH group blocking on the protein profile of recombinant urease. DTNB-treated and control samples dialyzed in PBS were prepared as described above for FIG. 23C. Recombinant urease stored for different time periods at 4° C. in 2% sucrose was also analyzed. The lanes of the gel are labeled as follows: lane MW, molecular weight markers; lane 1, urease solution stored at 4° C. for 9 weeks; lane 2, urease solution stored at 4° C. for 5 weeks; lane 3, urease solution stored at 4° C. for 3 10 days; lane 4, urease solution dialyzed against PBS for 48 hours; lane 5, urease solution treated with DTNB and then dialyzed against PBS for 48 hours.

Figure 24B:
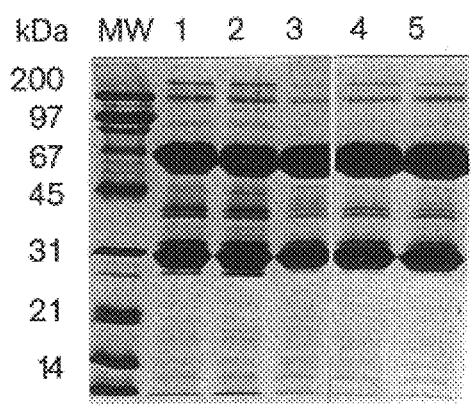

FIG. 24B is a photograph of non-reducing SDS-PAGE and Coomassie staining analysis showing the effect of storage time and SH group blocking on the protein profile of recombinant urease. Sample preparation and lane labels are as described above for FIG. 24A.

Figure 24C:
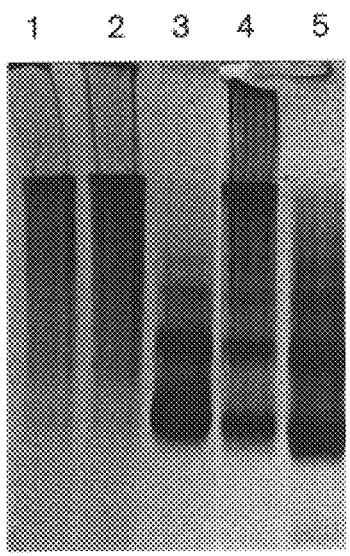

FIG. 24C is a photograph of native PAGE and Coomassie staining analysis showing the effect of storage time and SH group blocking on the protein profile of recombinant urease. Sample preparation and lane labels are as described above for FIG. 24A.

Figure 25A:
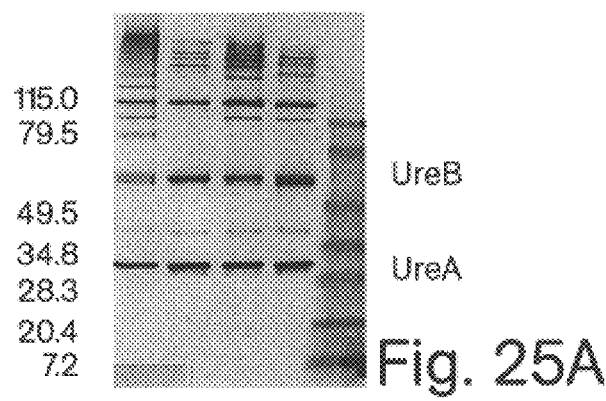

FIG. 25A is a photograph of Western blot analysis of urease stored under different conditions and treated with DTNB using MPA3 (see analytical methods, below). The conditions used for the samples present in each lane are as follows: 1, urease stored in solution for 9 weeks; 2, urease solution stored at 4° C. for 3 days; 3, urease solution dialyzed against PBS; 4, DTNB-treated urease dialyzed against PBS.

Figure 25B:
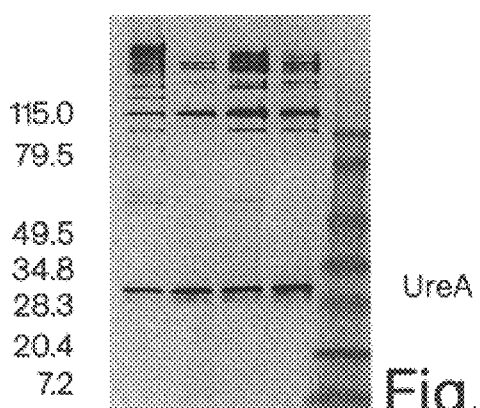

FIG. 25B is a photograph of Western blot analysis of the urease samples described above for FIG. 25A using MPA4 (see analytical methods, below).

Figure 25C:
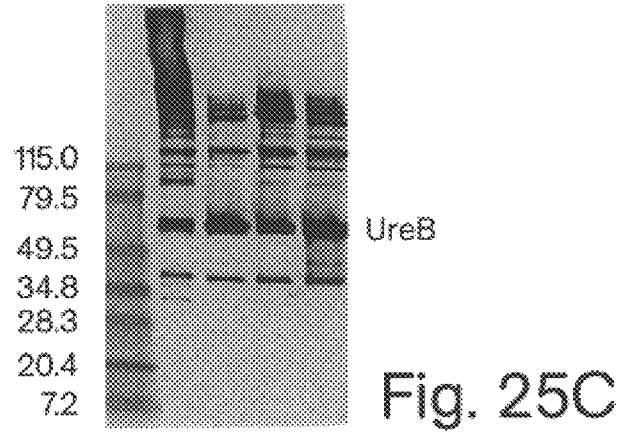

FIG. 25C is a photograph of Western blot analysis of the urease samples described above for FIG. 25A using MPA6 (see analytical methods, below) and non-reducing SDS-PAGE.

Figure 26A:
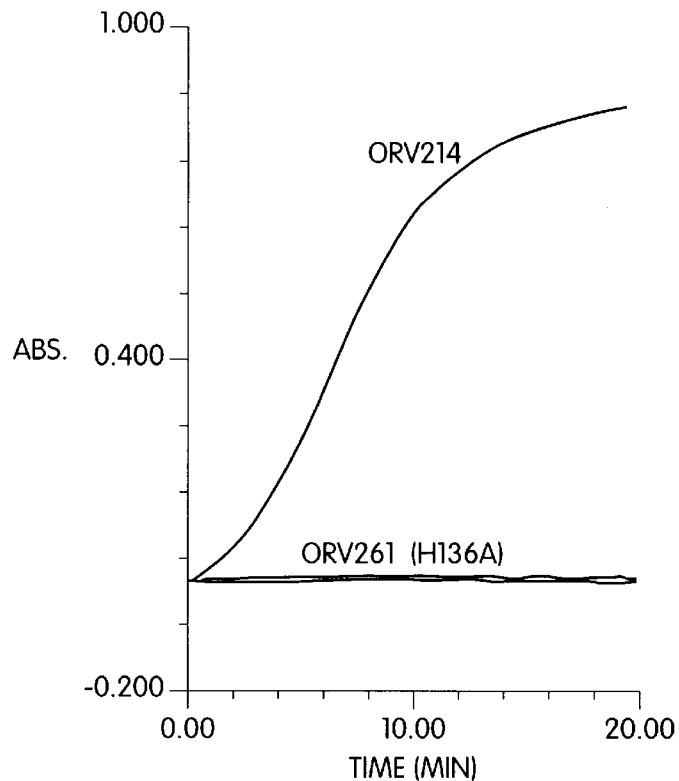

FIG. 26A is a graph showing that recombinant apourease obtained from an E. coli pellet carrying mutant ureA-ureB structural genes (H136A mutation) cannot be activated. Recombinant urease produced from ORV261-H136A mutant and ORV214 pellets were purified by a combination of ion-exchange and membrane filtration procedures, incubated with activation buffer, and tested for activity, as described above for FIG. 1.

Figure 26B:
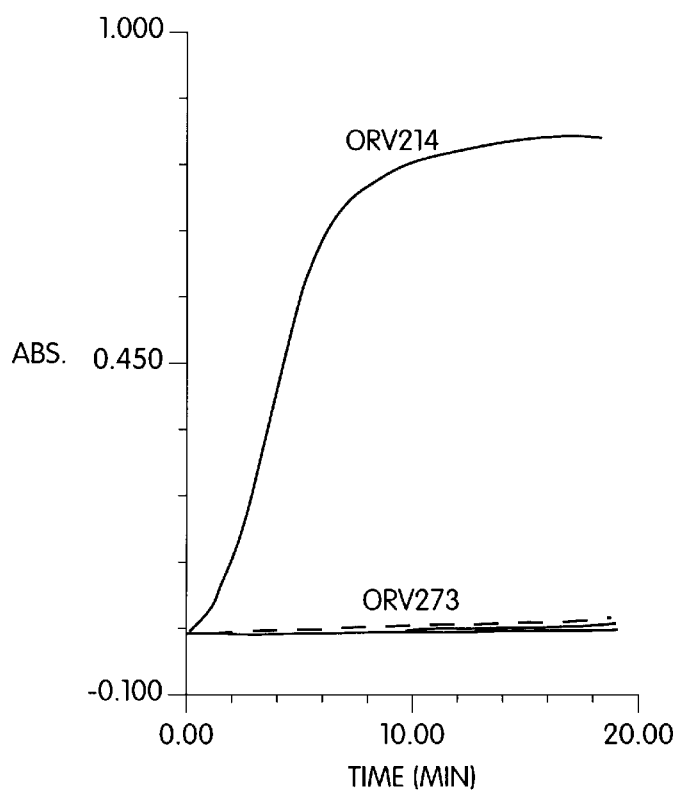

FIG. 26B is a graph showing that recombinant apourease produced from E. coli strain ORV273, which carries mutant urease structural genes (K219A plus H248A double mutation), is not activated by incubation with bicarbonate and nickel ions. Recombinant urease produced from the ORV273 mutant and ORV214 pellets was purified by a combination of ion-exchange and membrane filtration procedures, incubated with activation buffer, and tested for activity as described above in reference to FIG. 1.

Figure 26C:
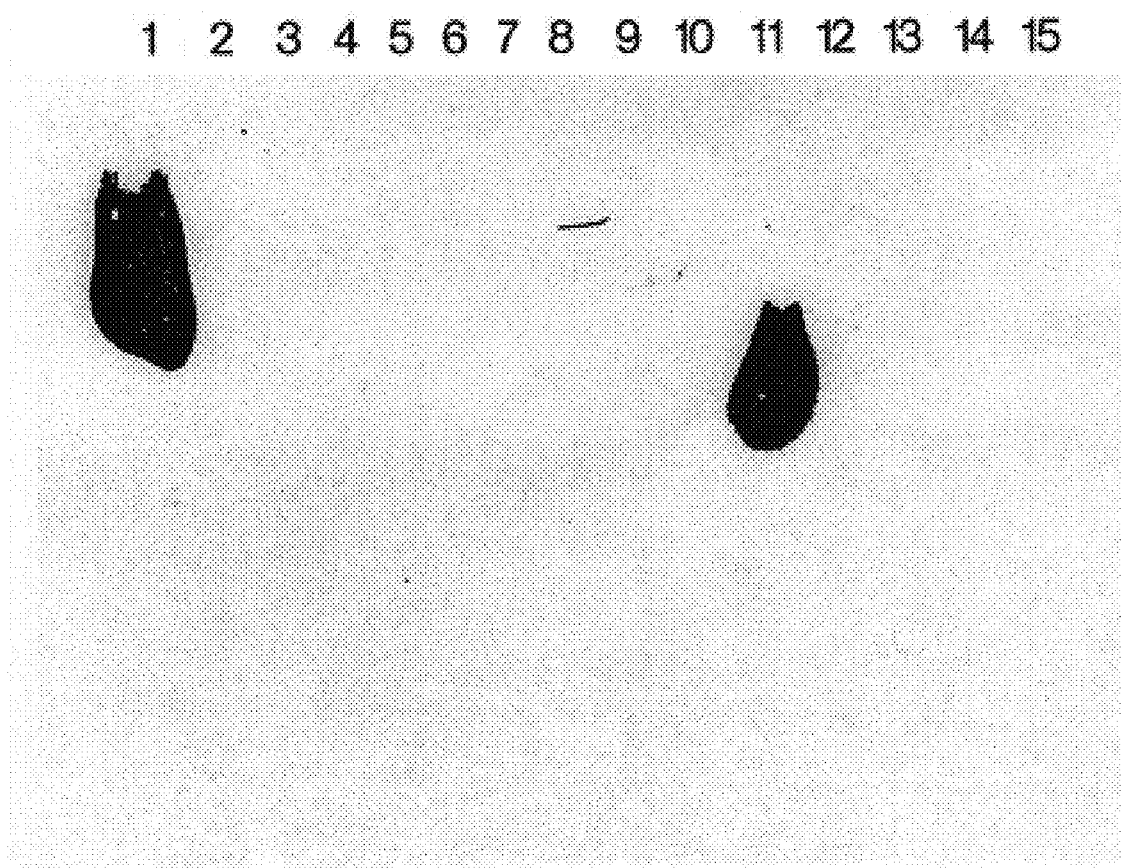

FIG. 26C is a graph showing that recombinant apourease produced and purified from mutant strain ORV273 is not activatable. Samples were treated with in vitro activation and control buffers and then separated on a native polyacrylamide gel. Gels were then stained for urease activity using urease-specific silver staining. Lane 1 contains urease from strain ORV214 incubated with in vitro activation buffer; lane 3 contains urease from strain ORV214 incubated with bicarbonate in the absence of nickel; lanes 5, 7, and 9 contain apourease from mutant strain ORV273 incubated with activation buffer; and lane 11 contains native H. pylori urease.

Figure 26D:
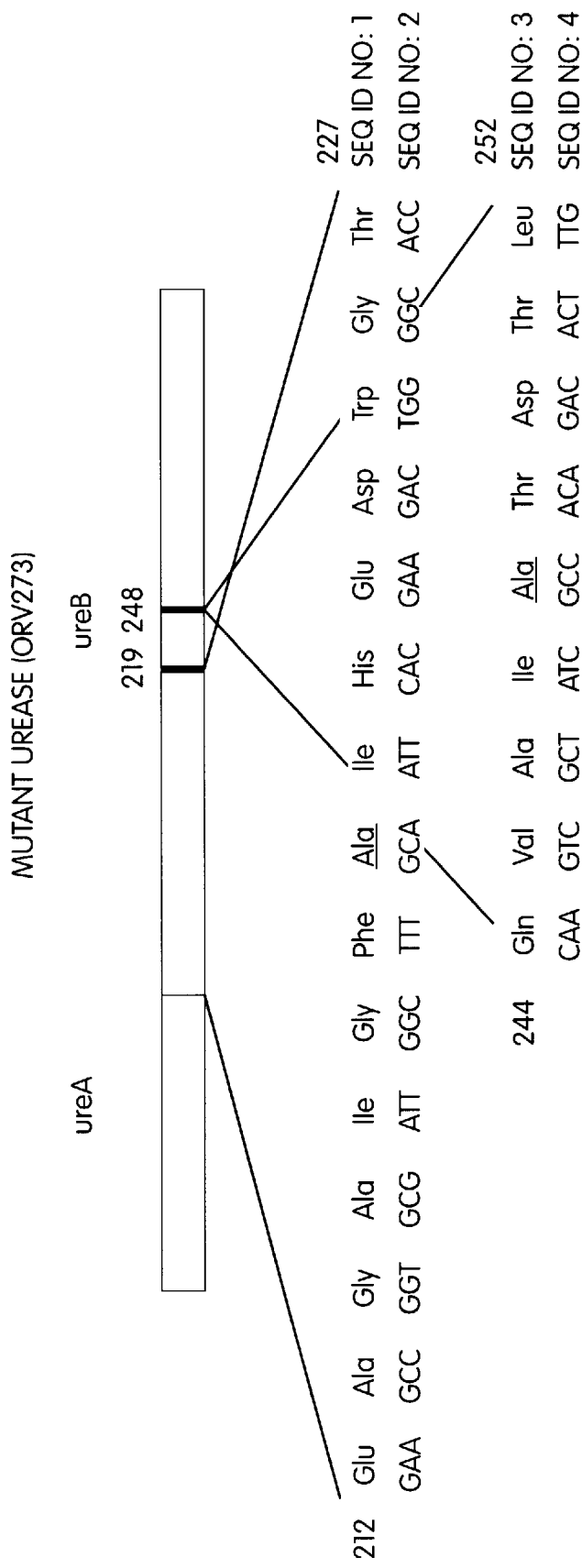

FIG. 26D is a schematic representation of the sites of mutation in ORV273. Lys 219 and His 248 of native urease are both replaced with Ala in ORV273.

FIG. 27 is a graph showing that recombinant apourease produced from the ORV273 double mutant strain (rUre 96IO1) protects mice from H. pylori infection with an efficacy comparable to that for apourease produced by strain ORV214 (rUre 94JO3). Groups of 10 mice were immunized with 4 oral doses of either 50, 500, or 5000 ng of recombinant urease admixed with 500 ng of E. coli heat-labile enterotoxin, and challenged with H. pylori. H. pylori colonization in the stomachs was determined by culture. Data points on the figure represent the number of colony forming units of H. pylori recovered from a quarter of the gastric antral tissue of a mouse. The data show that immunization with recombinant, mutant H. pylori urease (lot 96101 purified from ORV273) gave similar levels of protection as that produced with recombinant, wild type H. pylori urease (lot 94J03 purified from pORV214).

Figure 28A:
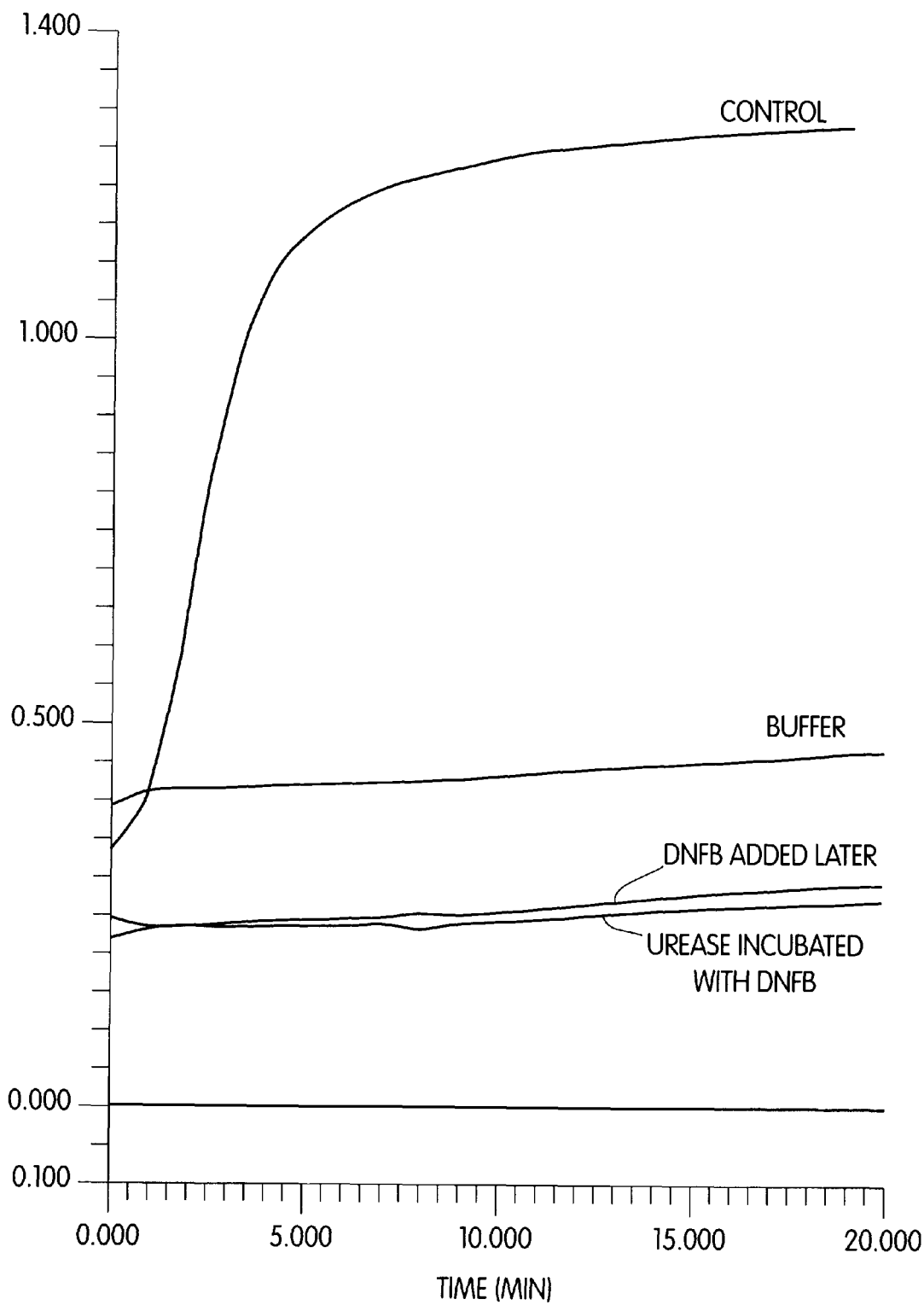

FIG. 28A is a graph showing that dinitrofluorobenzene (DNFB) treatment blocks in vitro activation of recombinant apourease. Purified recombinant urease from strain ORV214 (~4.0 mg/ml) in 50 mM phosphate (pH 8.0) was incubated with 1 mM DNFB for 1 hour at 37° C. A control sample, without DNFB, was also incubated for 1 hour at 37° C. After 1 hour of incubation, 100 μl of DNFB-treated and control samples were incubated with 100 μl of activation buffer containing Hepes, nickel chloride, and sodium bicarbonate for 2 hours and 30 minutes at 37° C. Urease enzyme activity was measured spectrophotometrically by monitoring the formation of phenolate anion at 550 nm, as described in FIG. 1. Curve "a" is a control sample, curve "b" is an DNFB-treated sample incubated with activation buffer, and curve "c" is a control sample incubated with activation buffer in the presence of DNFB. These results show that the DNFB-treated samples are not activated and that activation is blocked if DNFB is added along with activation buffer. There was precipitation in samples containing DNFB during incubation with activation buffer.

Figure 28B:
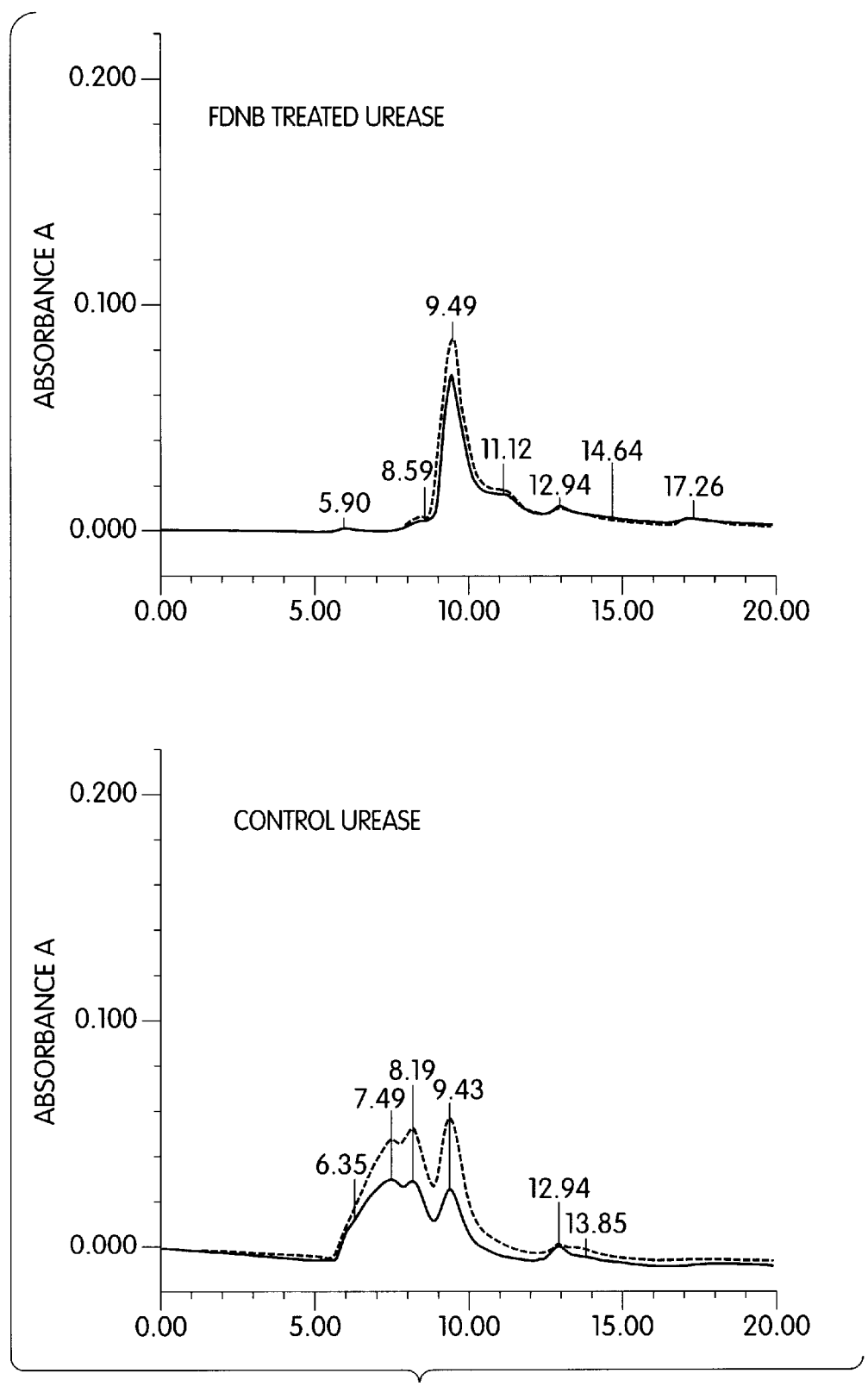

FIG. 28B is a set of graphs showing that DNFB treatment stabilizes recombinant apourease. Panel 1 shows DNFB treated urease and panel 2 shows control, untreated urease. DNFB treated and control samples as described above in reference to FIG. 28A were dialyzed against a phosphate buffer overnight. Dialyzed samples were analyzed by analytical HPLC size-exclusion chromatography as described above. These results show that molecular aggregation and degradation of control urease occurs during dialysis, and that DNFB treatment stabilizes the hexameric form of urease.

Figure 28C:
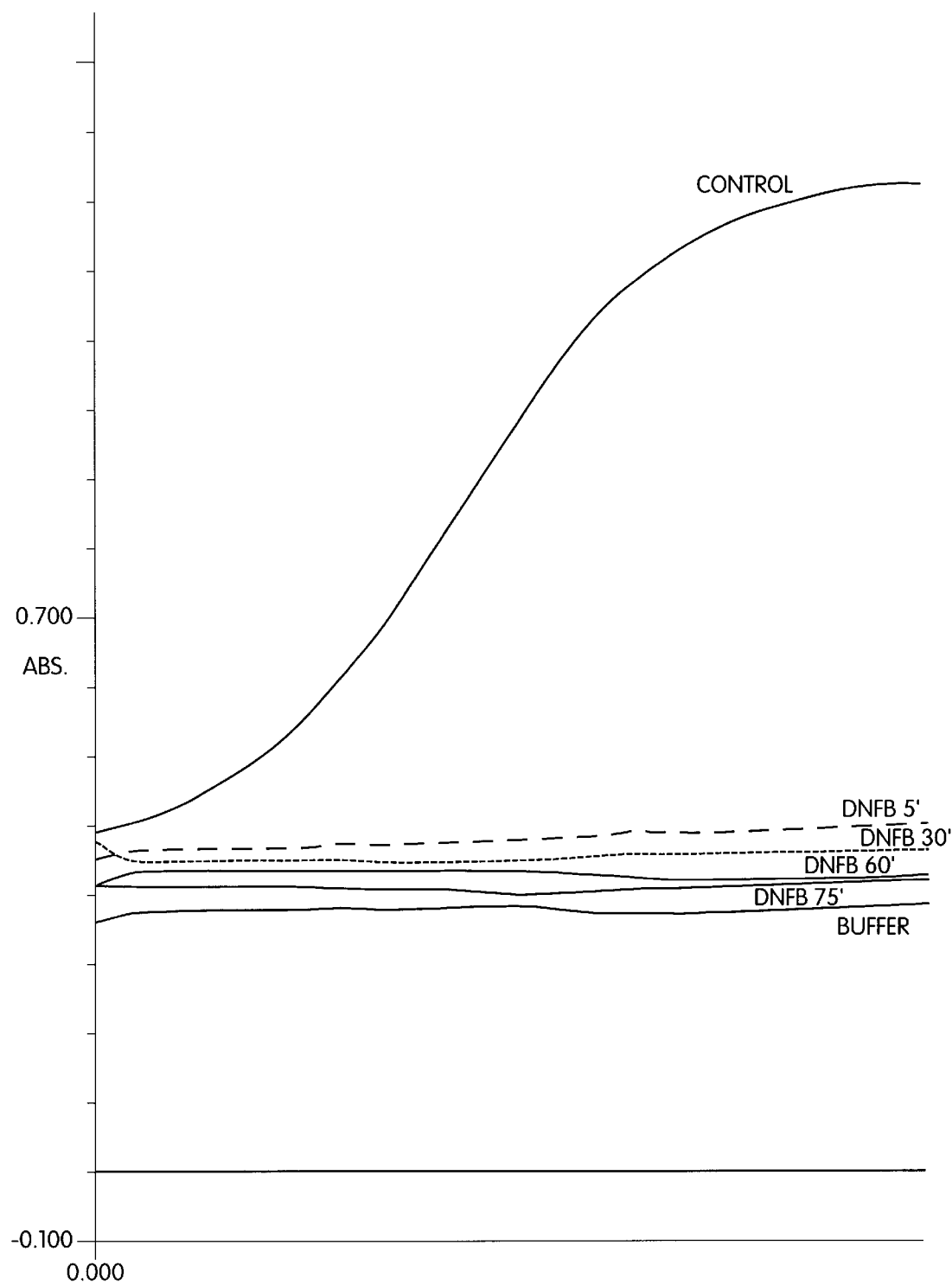

FIG. 28C is a graph showing that DNFB treatment for 5, 15, 30, and 60 minutes blocks in vitro activation of recombinant apourease. Purified recombinant urease from strain ORV214 was incubated with 0.5 mM DNFB. The reaction with DNFB was arrested at the indicated time points by transferring 1 ml aliquots to 200 μl of 100 mM Cysteine-HCl (pH 7.0). Samples were then dialyzed overnight against 20 mM phosphate buffer, pH 7.5, containing 2% sucrose. Dialyzed samples were then incubated with activation buffer containing nickel chloride and bicarbonate for 2.5 hours at 37° C. Urease catalytic activity was then monitored by using the phenol broth assay as described above in reference to FIG. 1.

Figure 28D:
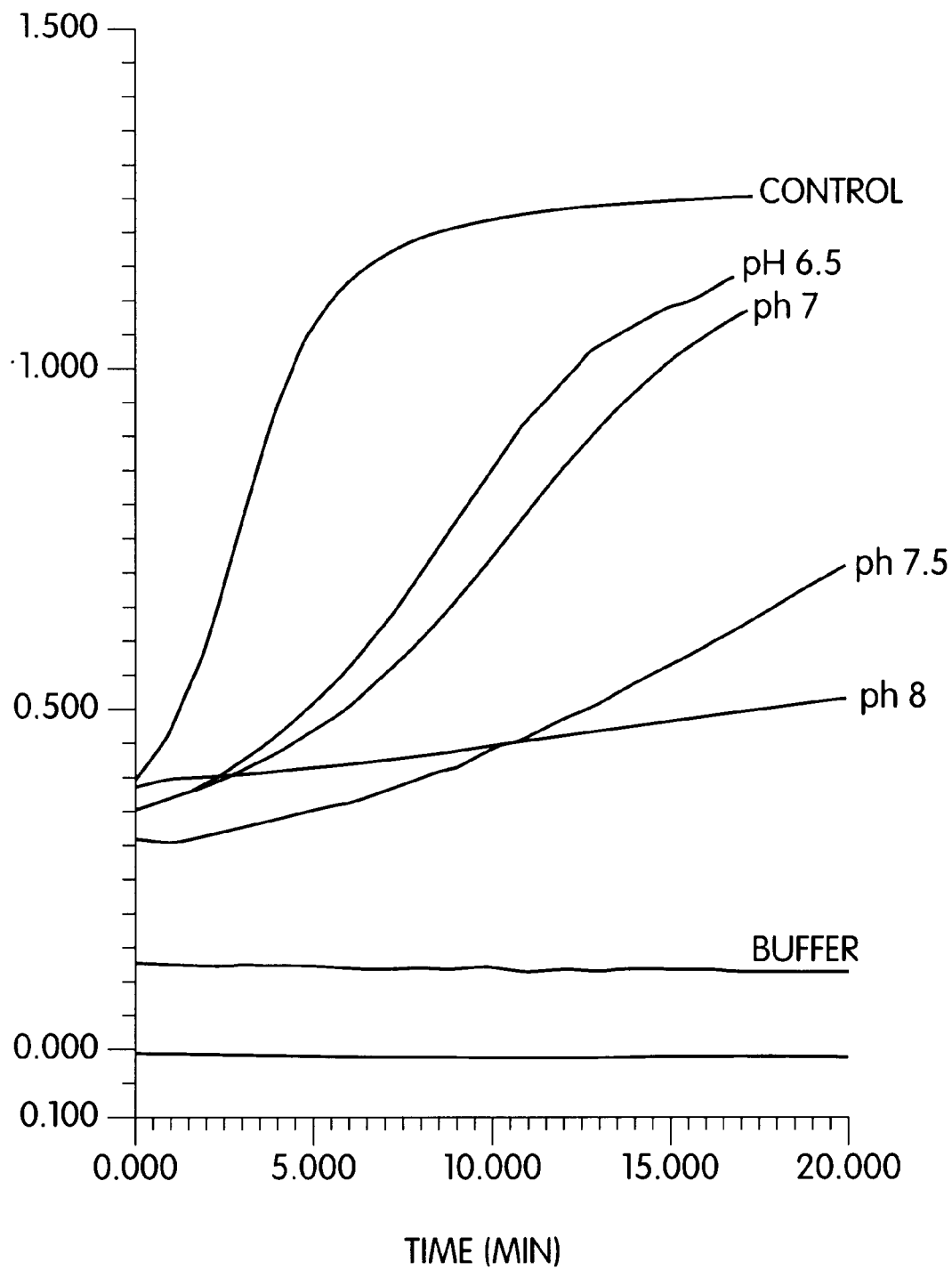

FIG. 28D is a graph showing that the effect of DNFB on blocking in vitro activation of urease is pH-dependent. Purified recombinant urease from strain ORV214 was incubated with 1 mM DNFB in 25–30 mM phosphate buffer at different pHs. After 5 minutes of incubation, samples were mixed with an equal volume of in vitro activation buffer containing nickel chloride and sodium bicarbonate in HEPES buffer, and incubation was continued at 37° C. for 3 hours. Urease enzyme activity was then determined as described above in reference to FIG. 1.

Figure 28E:
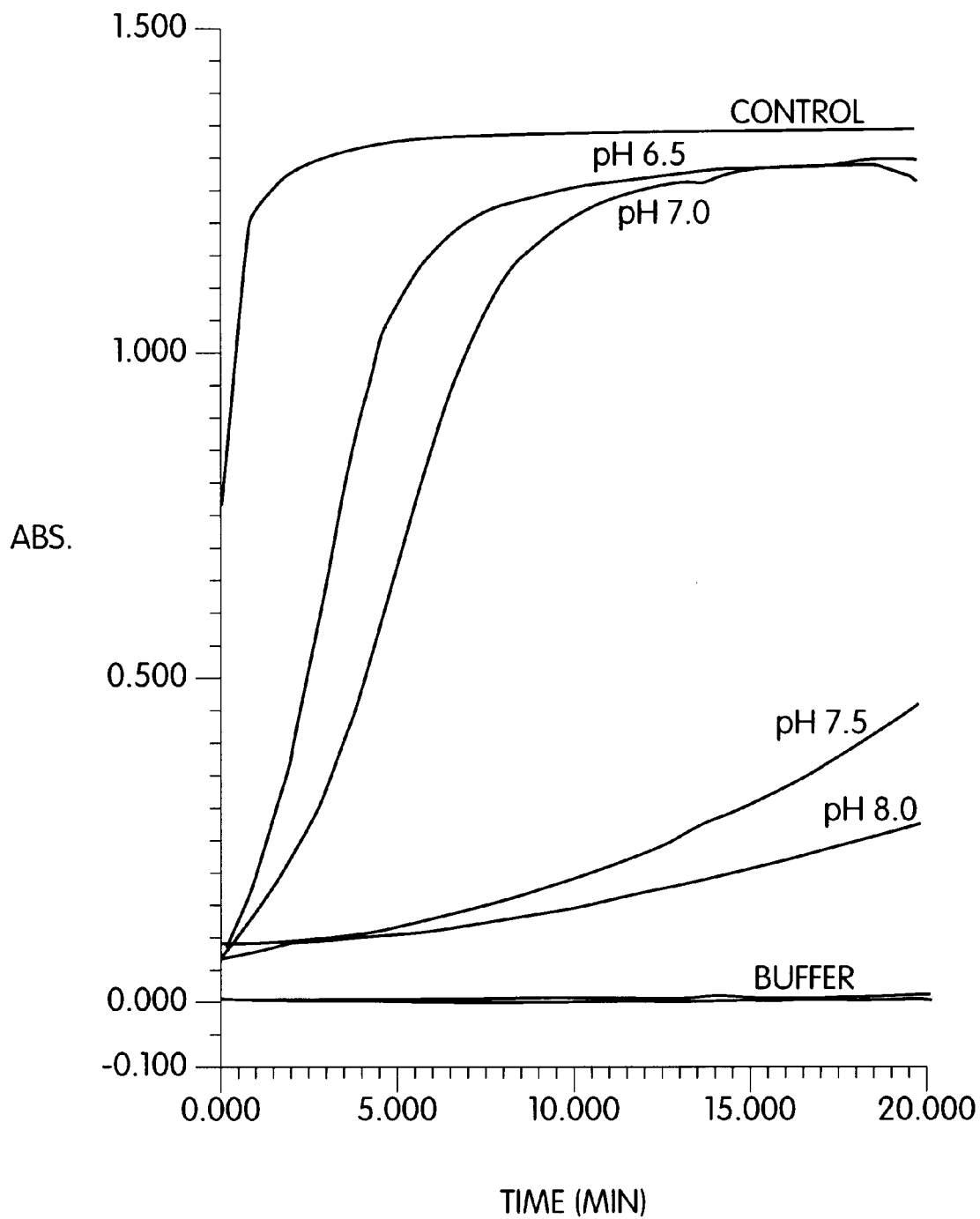

FIG. 28E is a graph showing that DNFB inactivates pre-activated urease in a pH-dependent manner, comparable to the effect of blocking in vitro activation of urease. Purified recombinant apourease from strain ORV214 was activated in vitro by incubation with bicarbonate-nickel chloride-Hepes buffer. Excess bicarbonate and nickel ions were removed by diafiltration against 10 mM phosphate, pH 7.4, using a Macrosep 100 (100 kDa NMWCO) filter centrifuge. Activated urease was then mixed with an equal volume of 200 mM phosphate buffer at the indicated pHs and incubated with 1 mM DNFB for 1 hour. Urease activity was then determined by using the phenol broth assay.

Figure 29:
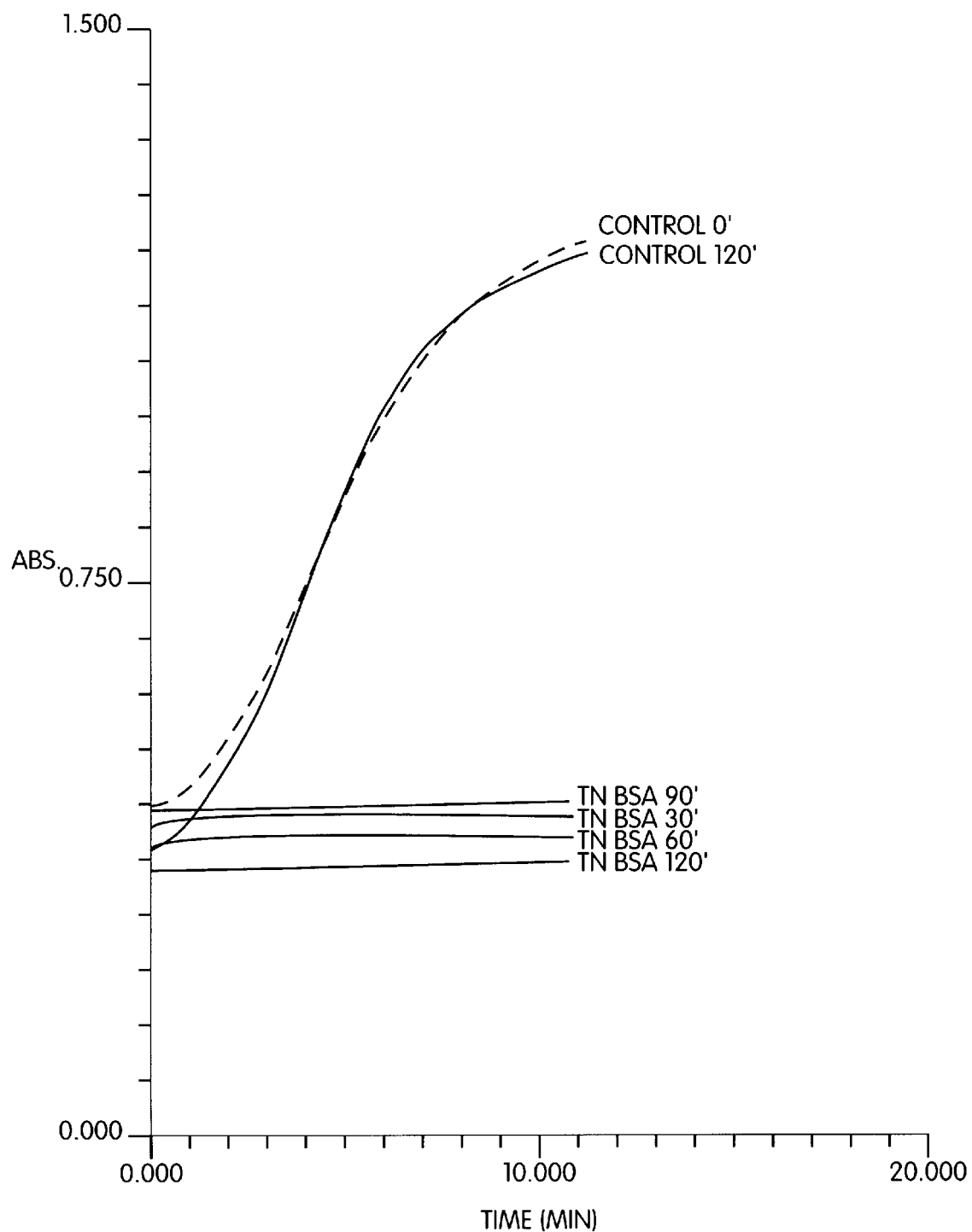

FIG. 29 is a graph showing that trinitrobenzene sulfonic acid (TNBSA) treatment blocks in vitro activation of recombinant apourease. Purified recombinant apourease from strain ORV214 was incubated with 5 mM TNBSA, pH 8.2, for 30–120 minutes. Controls without TNBSA were incubated under identical conditions. At specified time points, samples were taken, mixed with equal volumes of in vitro activation buffer containing nickel chloride, bicarbonate, and Hepes, and incubated at 37° C. for 2 hours. Urease activity was then determined by using the phenol broth assay, as described above in reference to FIG. 1.

DETAILED DESCRIPTION

As is described below, Helicobacter apourease in solution can be heterogeneous (i.e., exist in different molecular forms), unstable, aggregated, interconverted between different molecular forms, and converted from an enzymatically inactive form to an active form in vitro by incubation with bicarbonate and nickel ions.

Accordingly, the invention provides methods for stabilizing Helicobacter urease. In one example of these methods, urease is treated with a compound that modifies an amino acid of the urease so that it cannot be converted into an enzymatically active form or the high molecular weight, polymeric aggregates characteristic of untreated urease (see below). An additional method for stabilizing urease, so that it cannot be converted into an enzymatically active form, involves introducing a genetic modification (e.g., an amino acid substitution) into the urease. Urease stabilized using either of these methods can be used, for example, in vaccination methods for preventing, treating, or diagnosing Helicobacter infection.

Chemical Stabilization of Helicobacter Urease

Each of the twenty amino acids has a free side chain, and many of these side chains have reactive functional groups, such as the thiol group of cysteine or the amino group of lysine. At least nine amino acid side chains (Cys, Lys, Asp, Glu, Arg, His, Trp, Tyr, and Met) can react under mild conditions with quite specific reagents to yield chemically modified amino acid derivatives. Numerous specific reagents for modifying amino acid side chains are known in the art (see, e.g., Fágáin, Biochimica et Biophysica Acta 1252:1–14, 1995; Means et al., Bioconjugate Chem. 1:2–12, 1990; Imoto etal., in *Protein Function: a Practical Approach* (Creighton, ed.) 247–277, IRL Press, Oxford, 1989; Lundblad et al., *Chemical Reagents for Protein Modification*, Vol. 1 & 2, CRC Press, Boca Raton, Fla., 1984), and can be used in the invention to stabilize Helicobacter urease.

Urease polypeptides that can be stabilized using the methods of the invention include urease polypeptides that are purified from Helicobacter (e.g., *H. pylori* or *H. felis*) cultures (Michetti et al., WO 94/09823; Dunn et al., J. Biol. Chem. 265:9464–9469; also see below), as well as urease polypeptides that are produced using recombinant methods (e.g., recombinant apourease; Lee et al., J. Infect. Dis. 172:161–172, 1995; Hu et aL, Infect. Immun. 60:2657–2666, 1992; also see below). Though there may be no differences in the amino acid sequences of a native urease and a corresponding recombinant apourease lacking nickel ions, the lack of nickel ions at the active site of the apourease may affect the conformation of the protein, particularly in the active site and nearby regions. Thus, the accessability and reactivity of functional amino acid residues in the active site of the apoprotein is likely to be very different from those of the native protein. The experiments described below show that chemical reagents used for amino acid modification can react with recombinant apourease and influence the activation and stability of the apourease.

Examples of chemical compounds that can be used to stabilize urease are as follows. Compounds that modify thiol groups, including disulfide-reactive agents, such as 5,5'-dithiobis(2-nitrobenzoic acid) (DTNB), 2,2'-dithiodipyridine (DTDP), cystine, cystamine, methyl methanethiolsulfonate (MMTS), and dinitrofluorobenzene (DNFB), as well as alkylating agents, such as iodoacetate (IAA), iodoacetamide (IAM; this compound also modifies lysine and histidine residues), and N-ethylmaleimide (NEM), can be used. Additional compounds that modify thiol groups and can be used in the invention include proton pump inhibitors that are converted into thiol-reactive sulfenamides at low pH. Examples of such compounds include omeprazole, lansoprazole, and derivatives of these compounds (e.g., AG-2000; Nagata et al., Antimicrobial Agents and Chemotherapy 39(2):567–570, 1995).

Compounds that modify amino groups can also be used to stabilize urease. For example, acetylating agents, such as acetic anhydride, methyl acetyl phosphate, pyridoxal phosphate, fluoronitrobenzenes (e.g., dinitrofluorobenzene (DNFB)), and LAM can be used. Trinitrobenzene sulfonic acid (TNBSA), which also modifies amino groups, can also be used to stabilize urease. In addition, compounds that modify histidine (e.g., iodoacetic acid and iodoacetamide) or arginine (phenylglyoxal and glyoxal) residues can be used in the invention to stabilize urease.

Methods for using these and other compounds to modify amino acids are known in the art and can readily be adapted for use with urease by one skilled in the art. For example, in the case of IAA, urease (e.g., 4 mg/ml) can be incubated with 0.1–25 mM IAA, e.g., 1 mM IAA, at room temperature for 5–20 minutes. Amounts of other compounds that can be used to stabilize urease are as follows: 1–200 mM LAM, 5–200 mM NEM, 0.1–5.0 mM DTNB, 0.01–4.5 mM DTDP, 0.5–1.0 mM Cystine, 0.25–1.0 mM Cystamine, and 25–100 $\mu$M MMTS. Stabilization reactions can be carried out, for example, in 80 mM HEPES (pH 7.75), 8 mM EDTA, at 20–40° C., e.g., at room temperature or 37° C.

Appropriate reaction conditions (e.g., reaction volume, buffer, incubation temperature, incubation length) for use with any of the above-listed compounds can readily be determined by one skilled in the art. For example, 0.5–10 mg/ml (e.g., 3–4 mg/ml) urease can be incubated with 0.1–100 mM modifying agent. Additional examples of reaction parameters that can be used are set forth below.

Chemical modification of urease can be performed after the final step of purification. For example, purified urease in a Tris or phosphate buffer (pH 7.5–8.6) can be incubated with 1–5 mM Iodoacetamide, 1–10 mM NEM, or 0.3–1 mM DTNB for 1 hour at room temperature. After this incubation, the samples can be diafiltered into 2% sucrose, with or without buffer, and concentrated to about 4.0 mg/ml.

Genetic Stabilization of Helicobacter Urease

In addition to the chemical methods described above, urease polypeptides can be stabilized, in order to prevent activation (e.g., in vitro activation), using genetic modification methods. Methods for modifying a nucleic acid so that it encodes an amino acid sequence containing a modification (i.e., an amino acid substitution, deletion, or addition), for example, site-directed and PCR mutagenesis methods, are well known in the art (see, e.g., Ausubel et al., eds. *Current Protocols in Molecular Biology*, Wiley & Sons, New York, 1989). A nucleic acid modified using these methods can be used to produce the modified protein using standard expression methods, such as those described below (also see, e.g., Ausubel et al., supra).

Amino acids that can be modified in order to produce stabilized Helicobacter urease of the invention include, for example, residues that are at the active site of the molecule (e.g., lysine 219), as well as residues that are involved in the formation of disulfide bridges. Specific examples of modifications included in the invention are as follows. A histidine residue at position 136, 138, 221, 248, 274, 314, 322, or 323 can be replaced, for example, with alanine or leucine. The aspartate residue at 362 or the lysine residue at position 219 can be replaced with alanine or leucine. In addition, cysteine (e.g., Cys 321 and Cys 257) and arginine (e.g., Arg 338 and Arg 340) residues of urease can be modified (for example, substituted, e.g., with alanine or leucine) according to the invention.

Use of stabilized Urease in Methods for Preventing or Treating Helicobacter Infection Urease that has been stabilized using the methods described above can be formulated for administration using standard methods appropriate for the intended mode of administration. For example, the stabilized urease can be combined with a stabilizer (e.g., a carbohydrate mannitol) and the product freeze dried (i.e., lyophilized). This process further prevents degradation by aggregation and fragmentation. In addition, the product is stable for months following lyophilization.

Stabilized urease can be freeze-dried following the final purification step (see below). The purified protein product (approximately 4 mg/ml) is dialyzed against 2% sucrose or diafiltered using a 10–100 kDa NMCO diafiltration membrane, and this solution is transferred to lyophilization vials. The vialed solution is either frozen in liquid nitrogen and then placed into the lyophilizer, or cooled to 4° C. and then placed in the lyophilizer, where it is frozen to −40° C., or lower. Lyophilization is carried out using standard methods. The freeze-dried product can be reconstituted in water.

Stabilized urease can be administered to a mucosal surface of a patient, such as a human patient, in order to stimulate a mucosal immune response effective to provide protection to subsequent exposure to Helicobacter and/or facilitate clearance of a pre-existing Helicobacter infection. Preferably, stabilized urease is administered to elicit a mucosal immune response associated with production of anti-urease IgA antibodies and/or infiltration of lymphocytes into the gastric mucosa. The stabilized urease can be administered to any mucosal surface of the patient. Preferable mucosal surfaces are oral, intranasal, and rectal (e.g., by use of an anal suppository) surfaces. In addition to being administered to a single mucosal surface, the vaccine of the invention can be administered to combinations of mucosal surfaces (e.g., oral+rectal, oral+intranasal, or rectal+ intranasal) or a combination of mucosal and parenteral administration can be used. In the case of oral administration, it is preferable that the administration involves ingestion of the vaccine, but the vaccine can also be administered as a mouth wash, so that an immune response is stimulated in the mucosal surface of the oral cavity, without actual ingestion of the vaccine. Alternatively, stabilized urease can be administered to a patient by the parenteral route, e.g., by subcutaneous, intravenous, or intramuscular injection.

Appropriate dosages of stabilized urease administered to a patient, whether for prevention or treatment of Helicobacter infection, can be determined by one skilled in the art. Generally, dosages will contain between about 10 $\mu$g to 1,000 mg stabilized urease. For mucosal immunization, preferred doses are between about 10 mg and 100 mg, while for parenteral immunization, preferred doses are between about 10 $\mu$g and 100 $\mu$g.

At least one dose of the stabilized urease can be administered to the patient, for example, at least two, four, six, or more total doses can be administered. It may be desirable to administer booster doses of the stabilized urease at one or two week intervals after the last immunization. Generally one booster dose containing less than, or the same amount of, stabilized urease as the initial dose is administered. For example, the vaccine regimen can be administered in four doses at one week intervals. For mucosal immunization, priming and booster doses can be administered to the same or different mucosal surfaces. In the case of different mucosal surfaces, for example, an oral priming dose can be followed by intranasal or rectal boosters, an intranasal priming dose can be followed by oral or rectal boosters, or a rectal priming dose can be followed by oral or intranasal boosters.

Stabilized urease can be co-administered with an adjuvant. For mucosal immunization, any mucosal adjuvant known in the art that is appropriate for use in the patient can be used. For example, the mucosal adjuvant can be cholera toxin (CT), enterotoxigenic *E. coli* heat-labile toxin (LT), or a derivative, subunit, or fragment of CT or LT that retains adjuvant activity. The mucosal adjuvant is co-administered with stabilized urease in an amount effective to elicit or enhance an immune response, particularly a humoral and/or a mucosal immune response. The ratio of adjuvant to stabilized urease that is administered can be determined by standard methods by one skilled in the art. For example, the adjuvant can be present at a ratio of 1 part adjuvant to 10 parts stabilized urease. Stabilized urease can be co-administered by the parenteral route with one or more of many adjuvants or immunomodulators known in the art. For example, the parenteral adjuvant can be aluminum hydroxide, aluminum phosphate, calcium phosphate, muramyl tripeptide, muramyl dipeptide, immunostimulatory complexes (ISCOMs), saponin derivatives, such as QS 21, oil-in-water emulsions, liposomes, block polymers, or any combinations of the above.

A buffer can be administered prior to administration of stabilized urease, in order to neutralize or increase the pH of the gastric acid of the stomach. Any buffer that is effective in raising the pH of gastric acid and is appropriate for use in the patient can be used. For example, buffers, such as sodium bicarbonate, potassium bicarbonate, and sodium phosphate, can be used. In the case of oral administration, the vaccine can be buffer-free, meaning that a pH-raising buffer compound effective to significantly affect gastric acid pH is not administered to the patient either prior to, or concomitant with, administration of the vaccine.

The vaccine formulation containing stabilized urease can also contain any of a variety of other components, including stabilizers, flavor enhancers (e.g., sugar), or, where the vaccine is administered as an antibacterial therapeutic, other compounds effective in facilitating clearance and/or eradication of the infecting bacteria (e.g., antibiotic compounds and proton pump inhibitors).

For prophylactic therapy, the vaccine containing stabilized urease can be administered at any time prior to contact with, or establishment of, Helicobacter infection. Because the vaccine can also act as an antibacterial therapy, there is no contraindication for administration of the vaccine if there is marginal evidence or suspicion of a pre-existing Helicobacter infection (e.g., an asymptomatic infection).

For use of the vaccine in antibacterial therapy, stabilized urease can be administered at any time before, during, or after the onset of symptoms associated with Helicobacter infection or with gastritis, peptic ulcers or other gastrointestinal disorders. Although it is not a prerequisite to the initiation of therapy, one can confirm diagnosis of Helicobacter infection by, e.g., a $^{13}C$ breath test, serology, gastroscopy, biopsy, or another Helicobacter detection method known in the art. The progress of immunized patients can be followed by general medical evaluation, screening for Helicobacter infection by serology, $^{13}C$. breath test, and/or gastroscopic examination.

In addition to its use for immunization against Helicobacter, stabilized urease can be used to immunize animals or humans against other conditions, such as ulcerative colitis and ammonia toxicity associated with hepatic failure.

Experimental Results
In Vitro Activation of Recombinant *Helicobacter pylori* Apourease Expressed in *Escherichia coli* by Bicarbonate and Nickel Ions Recombinant *H. pylori* urease apoprotein expressed in *E. coli* strain ORV214 can be used as an oral vaccine for the prophylactic and therapeutic treatment of peptic ulcer caused by *H. pylori* infection. Since it does not contain $Ni^{++}$ ions and is synthesized by recombinant *E. coli* lacking urease accessory assembly genes, the urease apoprotein is predicted to be catalytically inactive. The experiments described below show that recombinant *H. pylori* urease apoprotein expressed in, and purified from, the ORV214 *E. coli* strain can be activated by in vitro incubation with supra-physiological concentrations of $Ni^{++}$ and bicarbonate.
Activation of recombinant urease with $Ni^{++}$ and bicarbonate Urease enzyme causes cleavage of urea as follows:

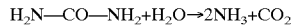
$$H_2N-CO-NH_2 + H_2O \rightarrow 2NH_3 + CO_2$$

Figure 2A:
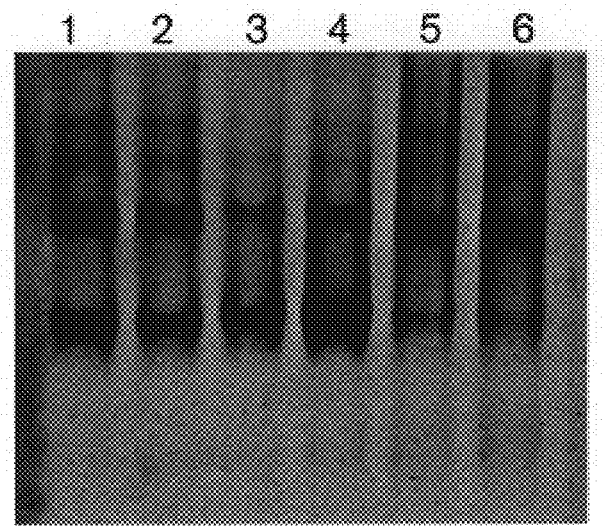
FIG. 2A is a photograph showing the activation of recombinant $H.$ $pylori$ urease by $Ni^{++}$ ions and bicarbonate. Recombinant urease was incubated with HEPES, NaCl, EDTA buffer containing bicarbonate and/or $Ni^{++}$ ions, as described above for FIG. 1. Samples 1 and 2 were incubated with both bicarbonate and $Ni^{++}$, samples 3 and 4 were incubated with bicarbonate alone, and samples 5 and 6 were incubated with $Ni^{++}$ alone. After 35 minutes of incubation at 37° C., the samples were transferred to a 4° C. refrigerator and stored overnight. The samples were then fractionated on a 4% polyacrylamide gel (precast gel from Novex) under non-reducing and non-dissociating conditions and stained using Coomassie blue.
Figure 2B:
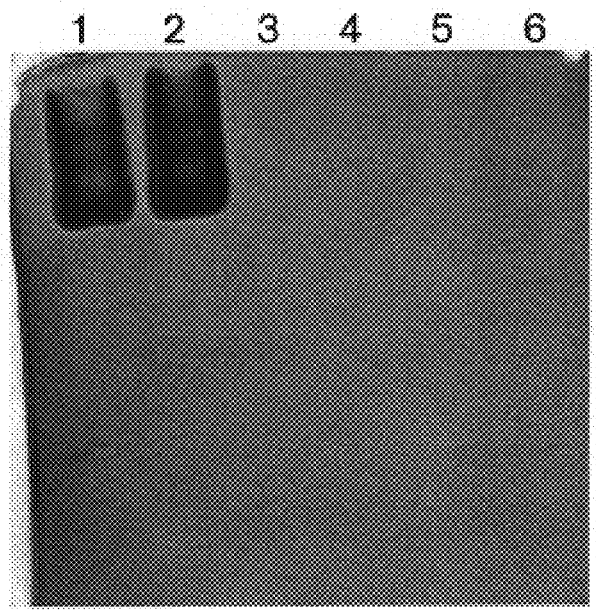
FIG. 2B is a photograph of urease-specific silver staining of the fractionated samples described above for FIG. 2A. (See, e.g., de Llano et al., Analytical Biochemistry 77:37–40, 1989, for details of urease-specific silver staining protocol.)
Figure 3:
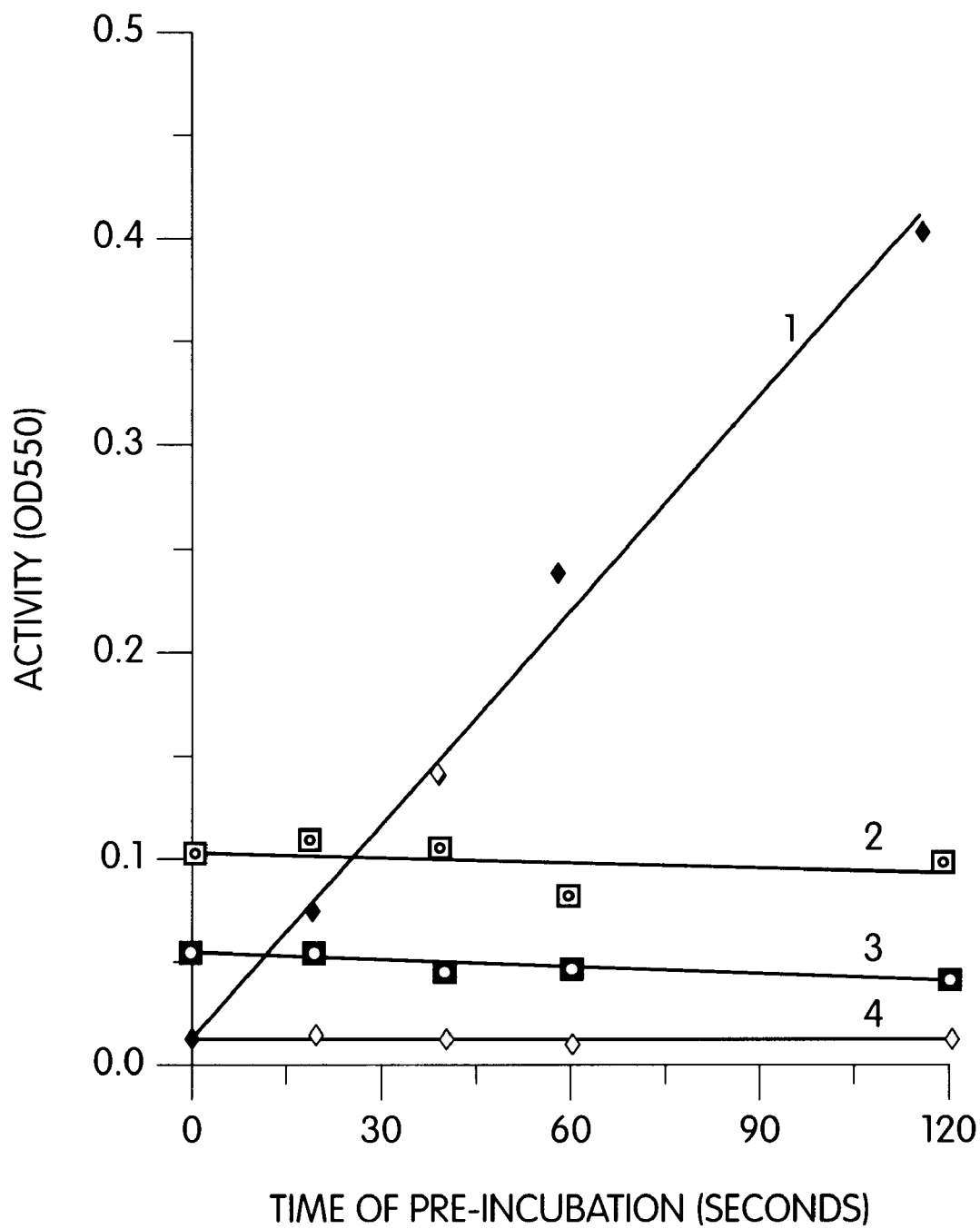
FIG. 3 is a graph showing the kinetics of activation of recombinant $H.$ $pylori$ urease incubated with $Ni^{++}$ ions and bicarbonate. Recombinant $H.$ $pylori$ urease was incubated at 37° C. with activation buffer. The activation mixture contained 2 mg/ml urease, 100 mM HEPES (pH 8.3), 0.3 M NaCl, 1 mM EDTA, 200 µM $Ni^{++}$, and 200 mM sodium bicarbonate. At the indicated time points, 10 µl of the activation mixture was transferred to 1 ml urea-broth, mixed well, and the absorbance at 550 nm followed for 15 minutes. The zero time reading is subtracted from the 15 minute reading and plotted against the time of activation at 37° C. in the activation system (1). Curves 2–4 show the results of Jack bean urease assayed at the different time points. The concentrations of urease in the assay system are (1) 20 µg/ml activated, recombinant $H.$ $pylori$ urease, (2) 2 µg/ml Jack bean urease, (3) 1 µg/ml Jack bean urease, and (4) 0.5 µg/ml Jack bean urease.
Figure 4:
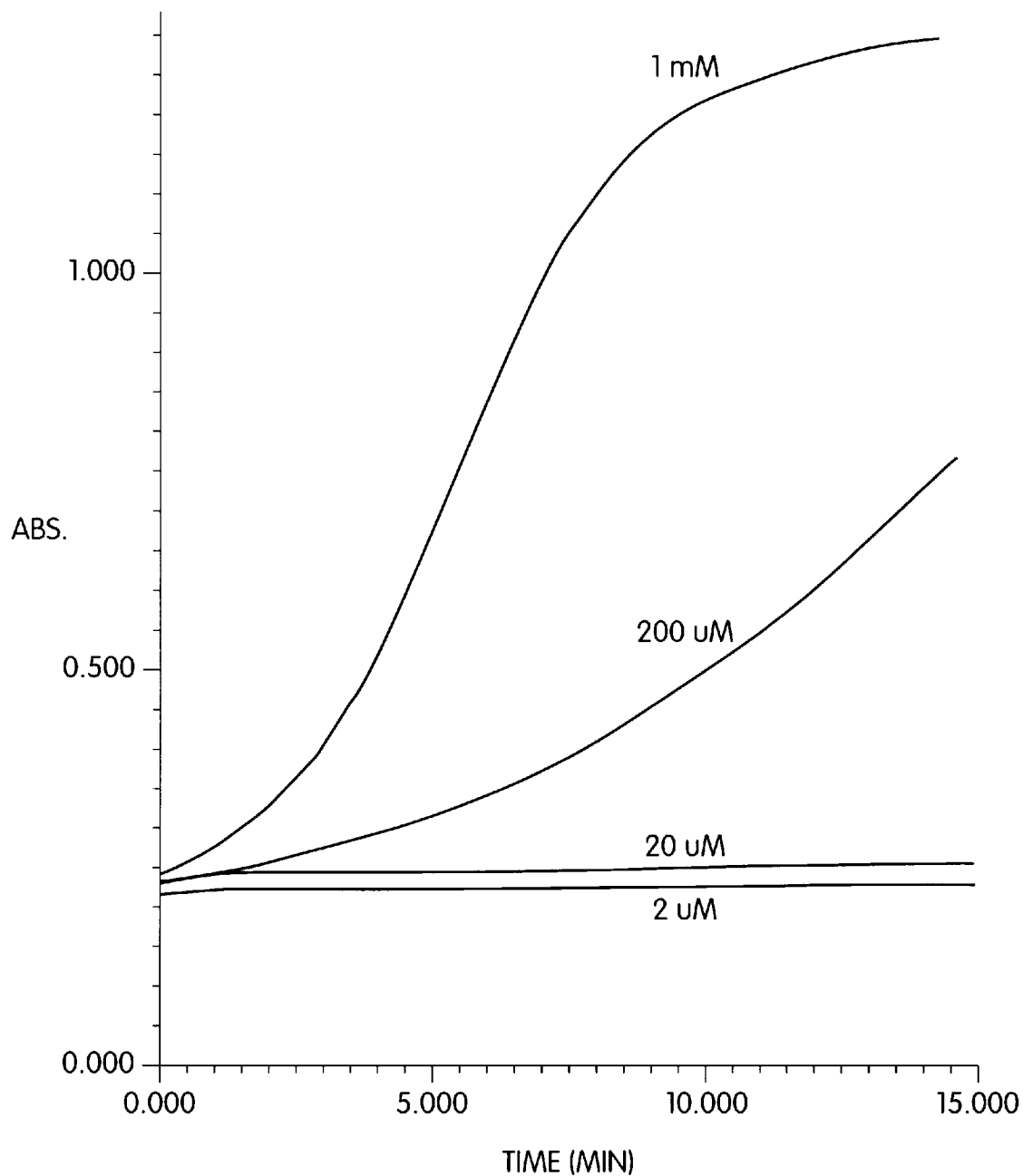
FIG. 4 is a graph showing that activation of recombinant $H.$ $pylori$ apourease increases with increasing $Ni^{++}$ ion concentrations (2 µM, 20 µM, 200 µM, and 1 mM). Recombinant $H.$ $pylori$ apourease was incubated at 37° C. for 1 hour in activation buffer (100 mM HEPES (pH 8.3), 0.3 M NaCl, 1 mM EDTA, 200 mM sodium bicarbonate) containing different amounts of $Ni^{++}$, as indicated in the Figure. After 1 hour of incubation, 10 µl of activated urease was transferred to 1 ml of urea broth, mixed well, and increases in absorbance at 550 nm were monitored for 15 minutes.

Urease activity was detected in urease preparations that were pre-incubated with bicarbonate and $Ni^{++}$ ions using the assay methods described below. The activation effect of bicarbonate and $Ni^{++}$ ions on recombinant urease measured using the phenol red urea broth colorimetric method is shown in FIG. 1. The conversion of urea to ammonia and carbon dioxide results in an increase in pH of the medium. The assay mixture contains phenol red, which undergoes ionization in alkaline pH to form a pink colored product, as measured by optical density readings at 550 nm. The reactions are performed in 1 cm cuvettes and increases in absorbance at 550 nm are continuously monitored using a Shimadzu Model UV-2101 PC with a CPM 260 multi-channel, temperature-controlled cuvette holder. Activity was detected only when both bicarbonate and $Ni^{++}$ ions were present in the pre-incubation system. These results are consistent with observations of *K. aerogenes* urease activity (Park et al., Science 267:1156–1158, 1995). Formation of ammonia was confirmed by direct estimation of ammonia from urea. Detection of urease activity by native PAGE and urease-specific silver staining is shown in FIG. 2. The urease protein is fractionated by electrophoresis in a polyacrylamide gel under non-denaturing conditions. The gel is then incubated with urea and stained with a pH sensitive redox system consisting of hydroquinone and p-aminophenol, followed by incubation with silver nitrate. Metallic silver is deposited on the gel at sites of urease enzymatic activity.
Time dependence of activation A time course of urease activation is shown in FIG. 3. These results show that activation is a time-dependent process, consistent with the occurrence of time-dependent modification of the protein.
$Ni^{++}$, bicarbonate, temperature, and pH-dependence of activation Experiments showing the $Ni^{++}$ ion concentration dependence of urease activation are shown in FIG. 4. Activation increases with increasing $Ni^{++}$ ion concentrations. Under the experimental conditions used, $Ni^{++}$ ion concentrations at or below 20 $\mu M$ in the pre-incubation system did not cause any significant activation of recombinant urease. In separate experiments, activation of recombinant urease was observed to occur at $Ni^{++}$ concentrations of 50 $\mu M$ and 100 $\mu M$.

Figure 5:
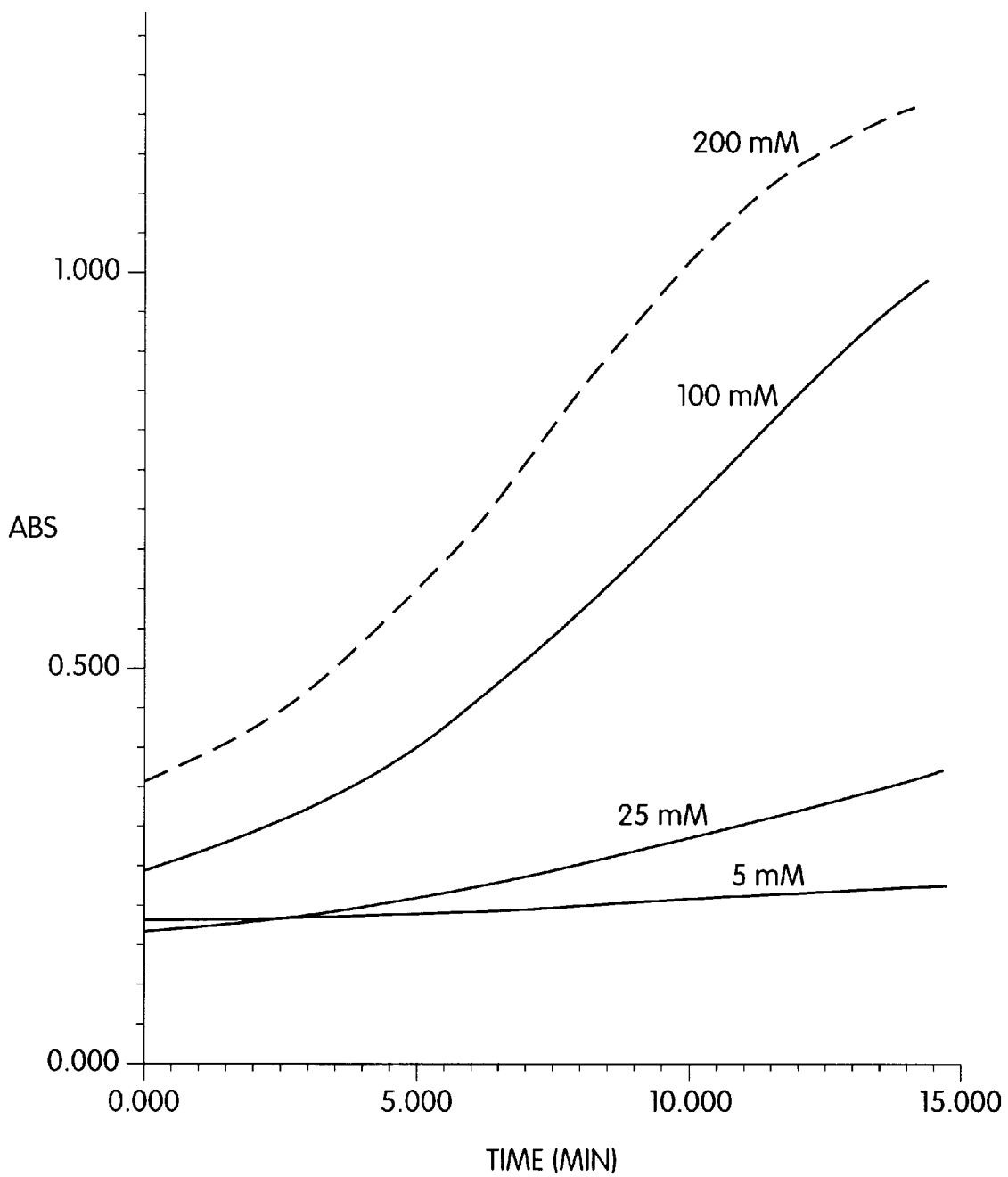
FIG. 5 is a graph showing that the activation of recombinant $H.$ $pylori$ apourease increases with increasing bicarbonate concentrations. Recombinant $H.$ $pylori$ apourease was incubated at 37° C. for 1 hour in activation buffer (100 mM HEPES (pH 8.3), 0.3 M NaCl, 1 mM EDTA, 200 µM $Ni^{++}$) containing different amounts of sodium bicarbonate, as indicated in the Figure. After 1 hour of incubation, 10 µl of activated urease was transferred to 1 ml of urea broth, mixed well, and increases in absorbance at 550 nm were monitored for 15 minutes.

Experiments showing the dependence of activation on bicarbonate concentration are shown in FIG. 5. The extent of activation increased with increasing bicarbonate concentrations, within the range of concentrations tested (5–500 mM bicarbonate).

Figure 6:
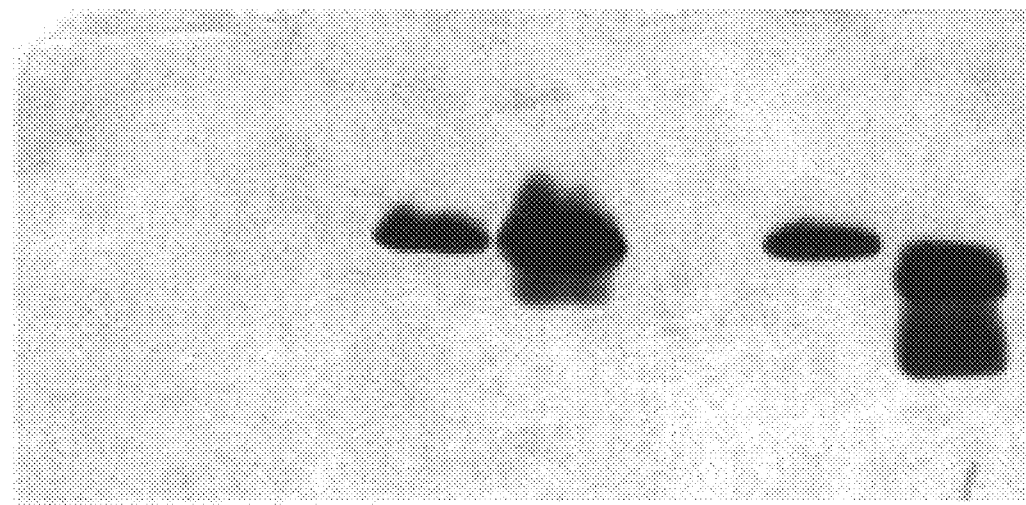
FIG. 6 is a photograph of a gel showing the effect of $Ni^{++}$ ions and bicarbonate on the activation of recombinant urease. Recombinant $H.$ $pylori$ urease was incubated at 37° C. for 1 hour in activation buffer containing 200 mM bicarbonate and different concentrations of $Ni^{++}$ (lane 1 is 2 µM $Ni^{++}$, lane 2 is 20 µM $Ni^{++}$, lane 3 is 200 µM $Ni^{++}$, and lane 4 is 1 mM $Ni^{++}$), 200 µM $Ni^{++}$ with 5 mM bicarbonate (lane 5), or 200 µM $Ni^{++}$ with 200 mM bicarbonate (lane 6). Samples were mixed with an equal volume of non-reducing and non-associating sample buffer and fractionated by electrophoresis on a 4% native polyacrylamide gel. After electrophoresis, the gel was stained using the urease activity-specific silver staining protocol. Lane 7 contains jack bean urease.
Figure 7A:
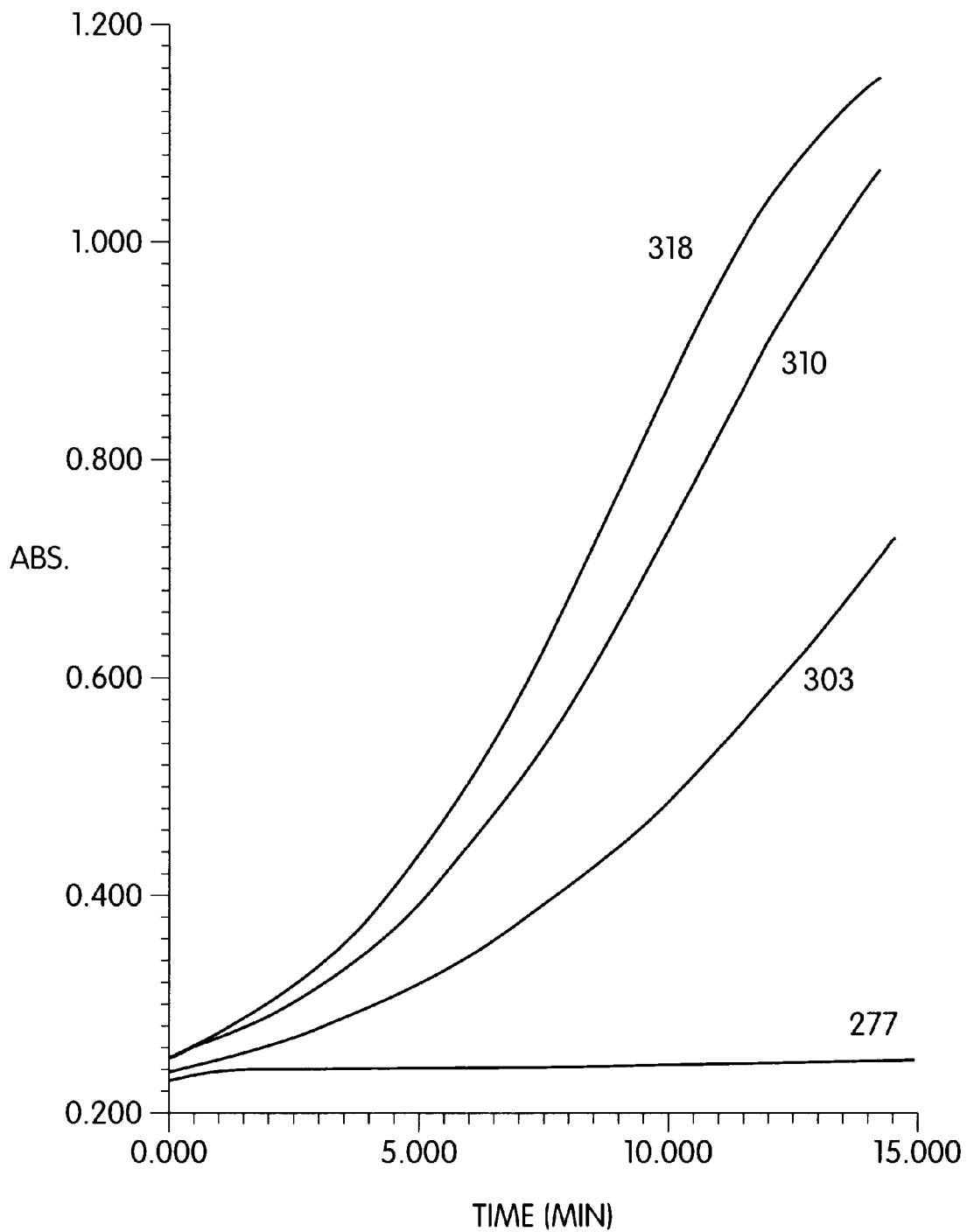
FIG. 7A is a graph showing that activation of recombinant *H. pylori* urease with bicarbonate and nickel ions is temperature dependent. Recombinant *H. pylori* apourease (2.0 mg/ml) was incubated in 100 mM HEPES (pH 8.3), 0.3 M NaCl, 1 mM EDTA, 200 μM $Ni^{++}$, 200 mM sodium bicarbonate for 1 hour at the indicated temperatures (temperature is expressed in absolute degrees (° K.)). After 1 hour of incubation, 10 μl of the activated urease was transferred to 1 ml of urease broth, mixed well, and the increase in absorbance was then monitored at 550 nmn.
Figure 7B:
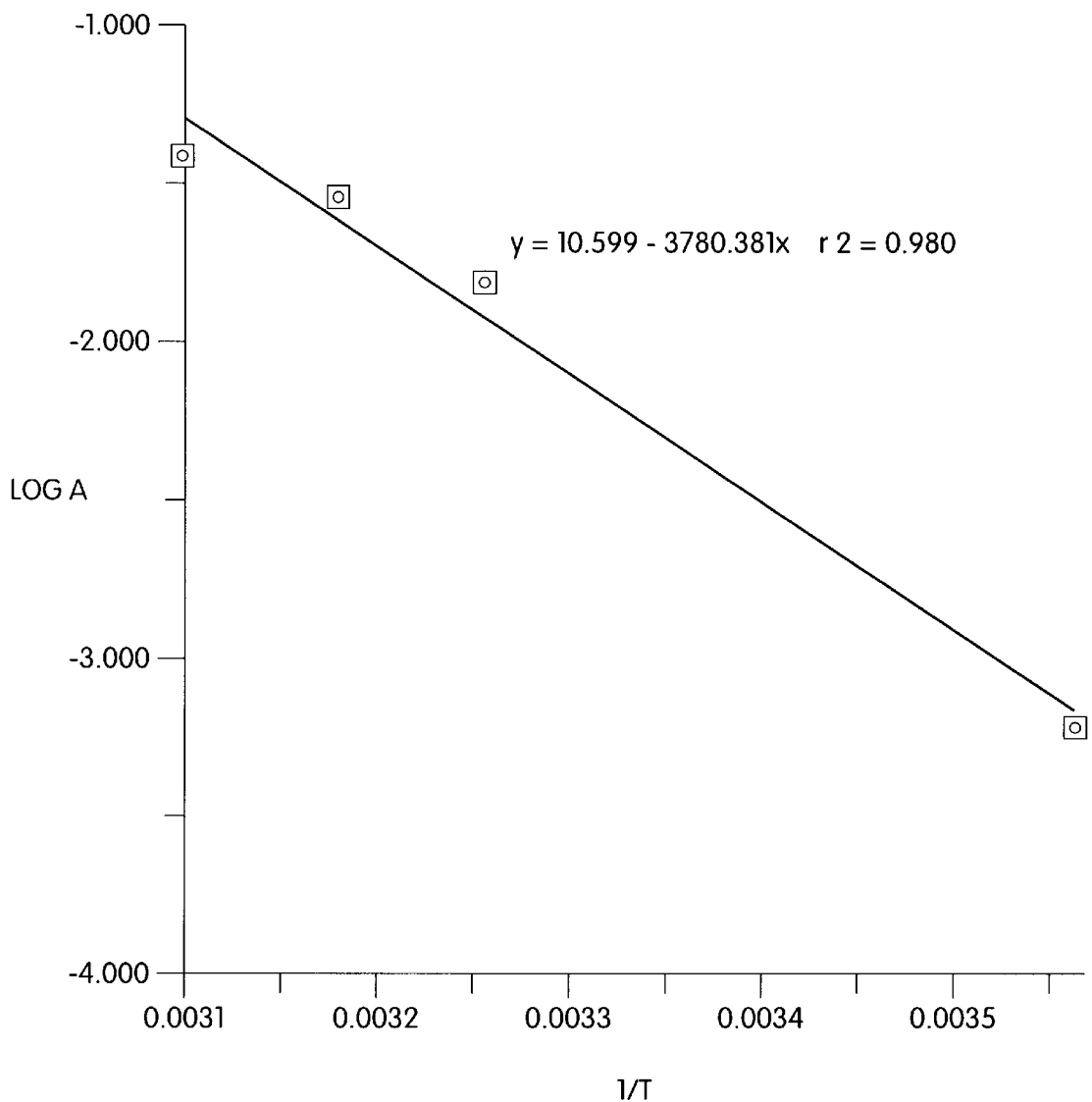
FIG. 7B is an Arrhenius plot of urease activation, which was constructed using relative activity, as measured by increase in absorbance (FIG. 7A) and absolute temperature.

Experiments showing the urease activity-specific silver staining of recombinant urease activated with different concentrations of $Ni^{++}$ and bicarbonate are shown in FIG. 6, and experiments showing the effect of temperature on the activation of recombinant urease are shown in FIG. 7. Activation is a temperature-dependent process, with the extent of activation increasing with increasing temperatures, ranging from 4–40° C. The slope of the best linear portion of the time course kinetics was assumed to be a relative measure of the activity. Because the substrate concentration in the assay mixture was far above the saturating concentration, the activity measured was very close to the maximal velocity, and hence is a measure of the apparent turnover rate constant. An Arrhenius plot of the activity resulted in a straight line, and an energy of activation of 17.4 kcals was calculated for urease activation.

pH dependence of activation

Figure 8:
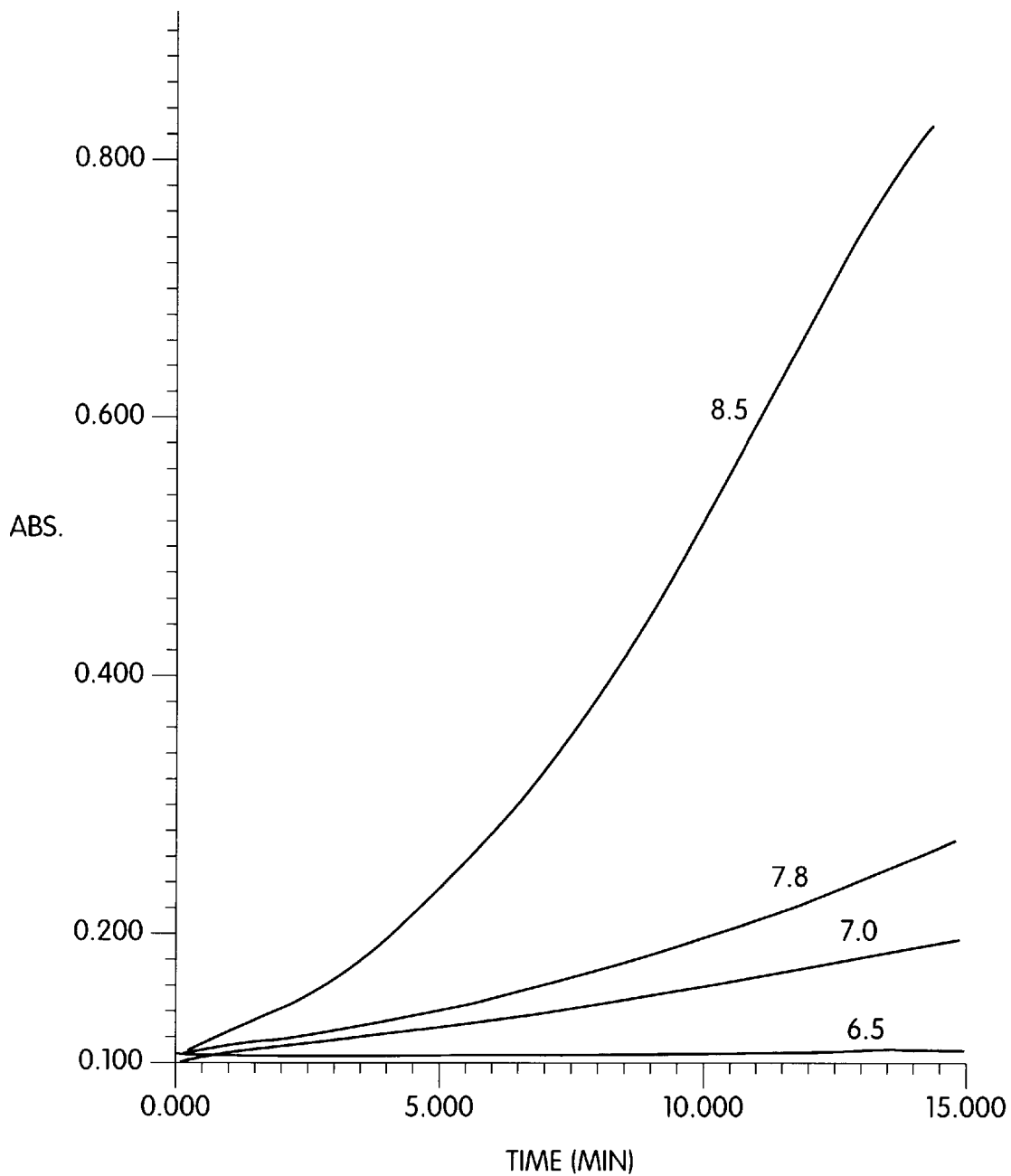
FIG. 8 is a graph showing that in vitro activation of recombinant *H. pylori* urease by $Ni^{++}$ and bicarbonate is pH dependent. Recombinant *H. pylori* apourease was incubated with 100 mM HEPES buffer, at the indicated pHs, containing 200 mM bicarbonate, 200 μM $Ni^{++}$ ions, 1 mM EDTA, and 0.3 M NaCl for 1 hour at 37° C. After 1 hour of incubation, 10 μl of the urease sample was added to 1 ml urea broth, and the increase in absorbance at 550 nm was monitored.

The results of an experiment showing the pH dependence of urease activation is shown in FIG. 8. No detectable activation occurred at pH 6.5. In separate experiments, it was found that activation does not occur at lower pH (<6.0).

Urease binding affinity of activated recombinant urease

Figure 9:
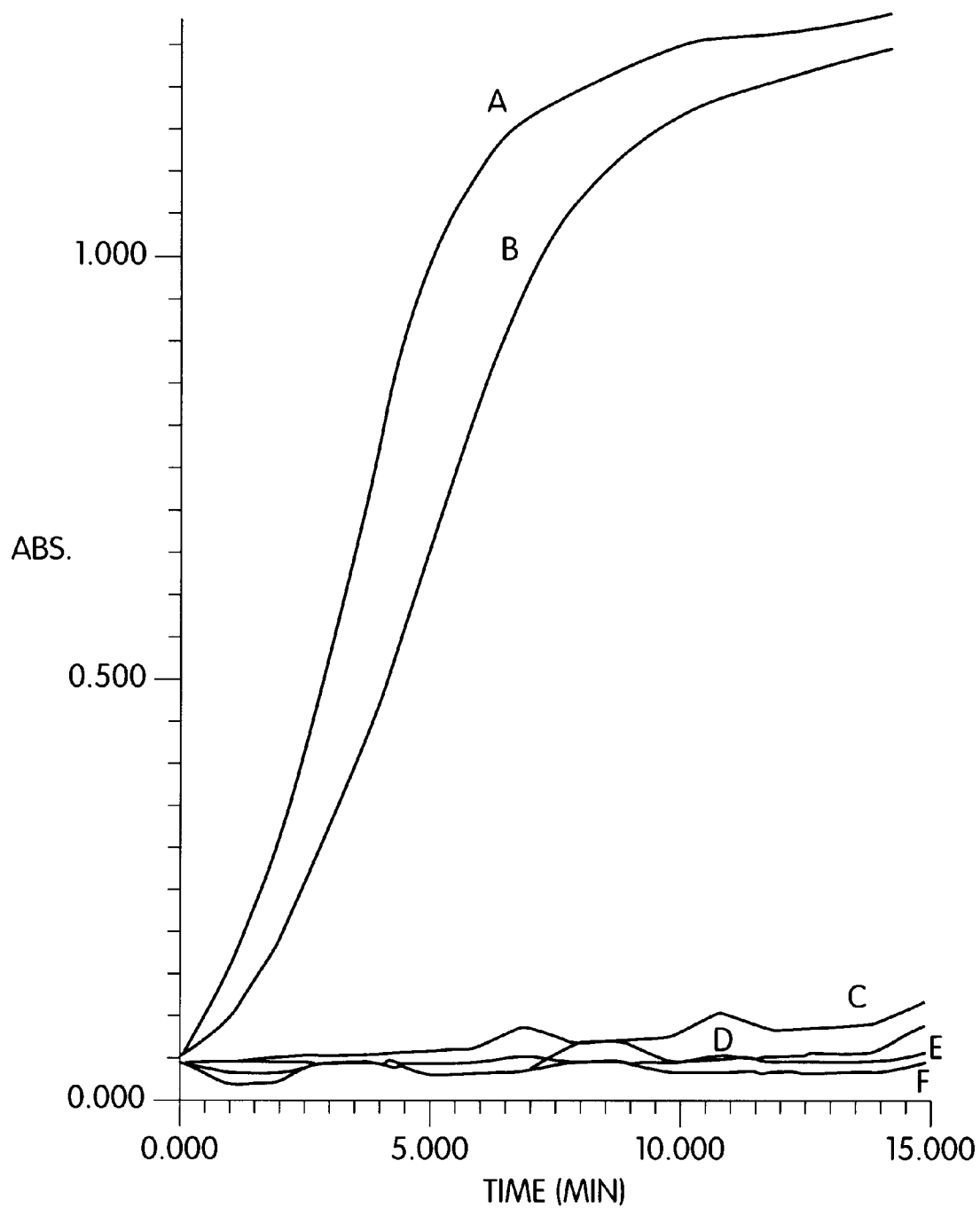
FIG. 9 is a graph showing that activated recombinant *H. pylori* urease retains catalytic activity after dialysis of unbound nickel and bicarbonate. Recombinant *H. pylori* apourease was incubated for 1 hour at 37° C. with 0.1 M HEPES (pH 8.3), 0.3 M NaCl, 1 mM EDTA, 1 mM $Ni^{++}$, and 200 mM sodium bicarbonate. Samples without bicarbonate or $Ni^{++}$ were also incubated at the same time. After 1 hour of incubation, the samples were dialyzed against 2% sucrose overnight. The dialyzed samples were analyzed immediately after dialysis and also after 6 days of storage at 4° C. after dialysis. Only urease that was preincubated with both bicarbonate and $Ni^{++}$ showed activity. Activity was retained after 6 days of storage at 4° C. in 2% sucrose. The curves are labeled as follows: urease incubated with $Ni^{++}$ plus bicarbonate immediately after dialysis (a) and 6 days after dialysis (b); urease incubated with $Ni^{++}$ immediately after dialysis (c) and 6 days after dialysis (d); urease incubated with bicarbonate immediately after dialysis (e) and 6 days after dialysis (f).

The activated urease retained catalytic activity after dialysis of unbound $Ni^{++}$ ions and bicarbonate. The activity of the dialyzed sample was retained for at least 1 week after storage at 4° C. in 2% sucrose (FIG. 9). The binding affinity of activated urease for urea was determined by carrying out spectrophotometric measurements of the decrease in NADH absorption at 340 nm accompanying NADH-dependent glutamate dehydrogenase catalyzed conversion of ammonia, produced by the hydrolysis of urea, and α-ketoglutarate to L-glutamic acid. The glutamate dehydrogenase reaction utilizes NADH that is converted to NAD. The NADH to NAD conversion is accompanied by a decrease in absorption at 340 nm. The reactions are performed in 1 cm cuvettes and decreases in absorbance at 340 nm are continuously monitored using a Shimadzu Model UV-2101 PC with a CPM 260 multi-channel, temperature-controlled cuvette holder.

Figure 10:
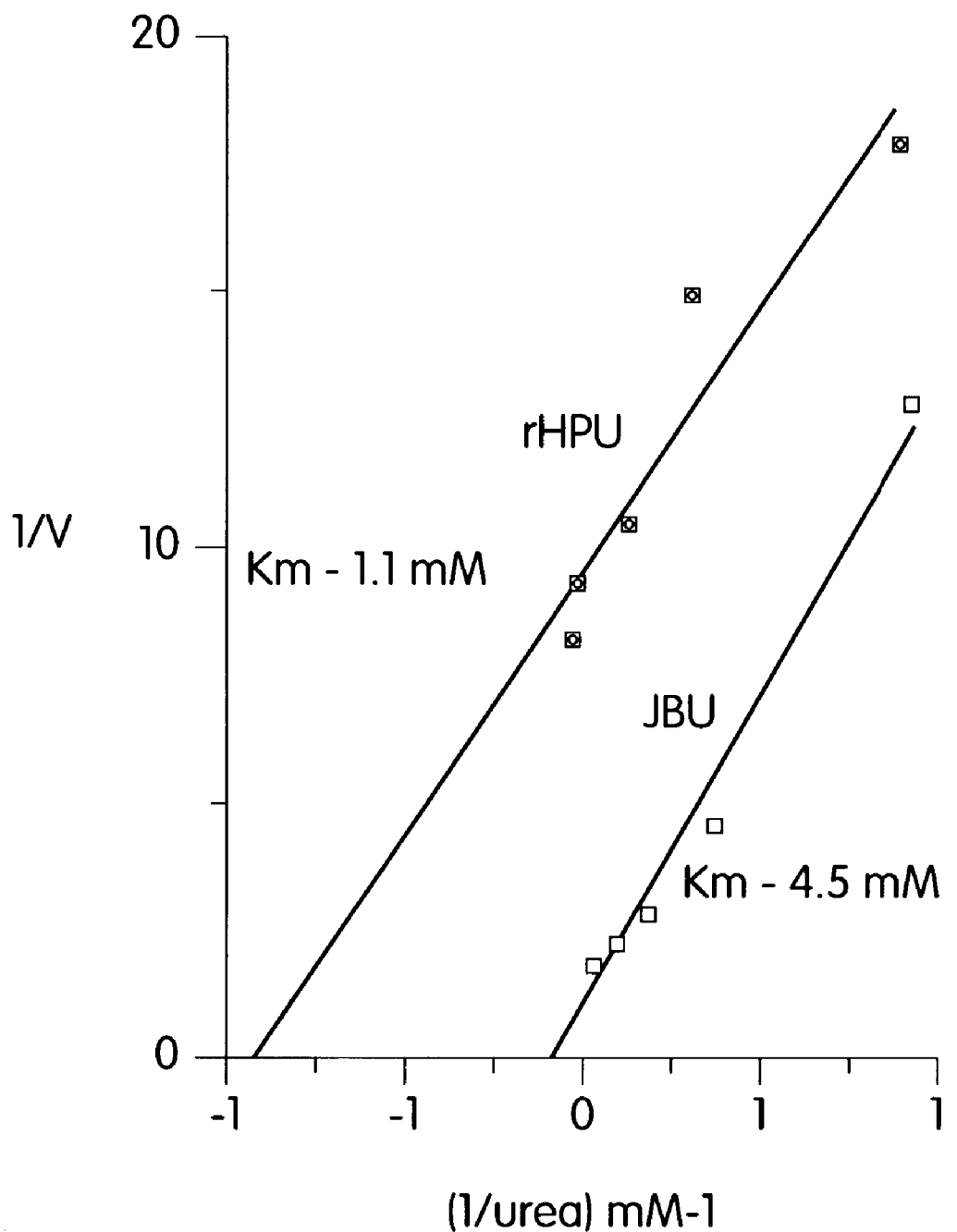
FIG. 10 is a graph showing a comparison of the affinities of activated *H. pylori* urease and jack bean urease for urea. Recombinant *H. pylori* urease was activated in vitro by incubation in urease activation buffer for 1 hour at 37° C. The activation system contained 2 mg/ml urease, 100 mM HEPES, 1 mM EDTA, 0.3 M NaCl, 200 mM sodium bicarbonate, and 1 mM $Ni^{++}$. After 1 hour of incubation at 37° C., the activated urease was dialyzed overnight against 2% sucrose. The activity of the urease was determined over urea concentrations ranging from 0.2–10.0 mM using the urease-coupled glutamate dehydrogenase assay. The assay system contained 50 mM Tris-HCl (pH 7.5), 1 mg/ml α-ketoglutarate, 0.4 mg/ml NADH, 6.5–300 μg/ml glutamate dehydrogenase, and varying concentrations of urea. Activated *H. pylori* urease and jack bean urease were used as sources of urease enzyme. The reaction tubes were blanked without urease and NADH. NADH was added to all of the tubes and absorbance was monitored for 1–2 minutes. One hundred and ten μl of urease enzyme was added, rapidly mixed, and decreases in absorbance at 340 nm were monitored. The slope of the best linear fit region of the kinetics of 340 nm absorbance decrease was taken as a measure of the initial velocity. A Lineweaver-Burk plot (1/V vs 1/S) was constructed and a $K_m$ value was determined from the slope and intercept.
Figure 11:
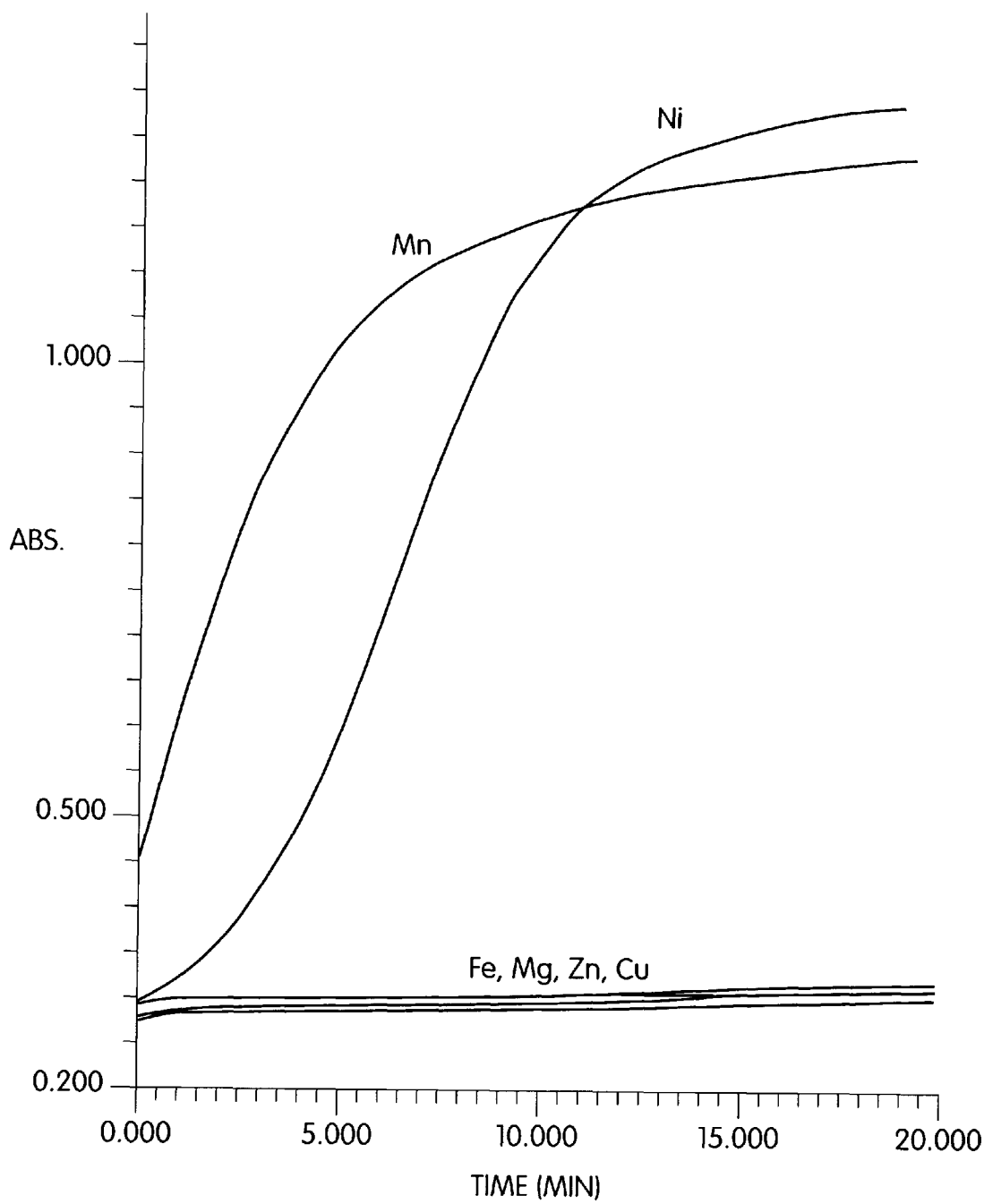
FIG. 11 is a graph showing the effect of other metal ions and bicarbonate on recombinant *H. pylori* apourease. Recombinant *H. pylori* apourease was incubated with 0.1 M HEPES (pH 8.3), 0.5 M sodium chloride, 1 mM EDTA, 200 mM sodium bicarbonate, and 200 μM of different metallic ions, as indicated in the Figure, for 1 hour at 37° C. After 1 hour of incubation, 10 μl of the urease sample were added to 1 ml of urea broth, and the absorbance at 550 nm was monitored.

Initial velocities computed from the slopes of the linear portions of the curves showing the kinetics of decreases in 340 nm absorption at varying concentrations of urea were plotted in Lineweaver-Burk double reciprocal plots. The Lineweaver-Burk plot for reactivated recombinant *H. pylori* urease is compared with that for jack bean (type IV (EC 3.5.1.5) Sigma catalog # U2000, Lot 122H7115) urease in FIG. 10. The $K_m$ value of 1.1 mM calculated for the recombinant urease is slightly higher than the values reported for native *H. pylori* urease (Mobley et al., Microbiol. Rev. 59:451–480, 1995), but is within the limits of experimental variations. The value is nearly four-fold lower than that estimated for jack bean urease under similar conditions.

Figure 12:
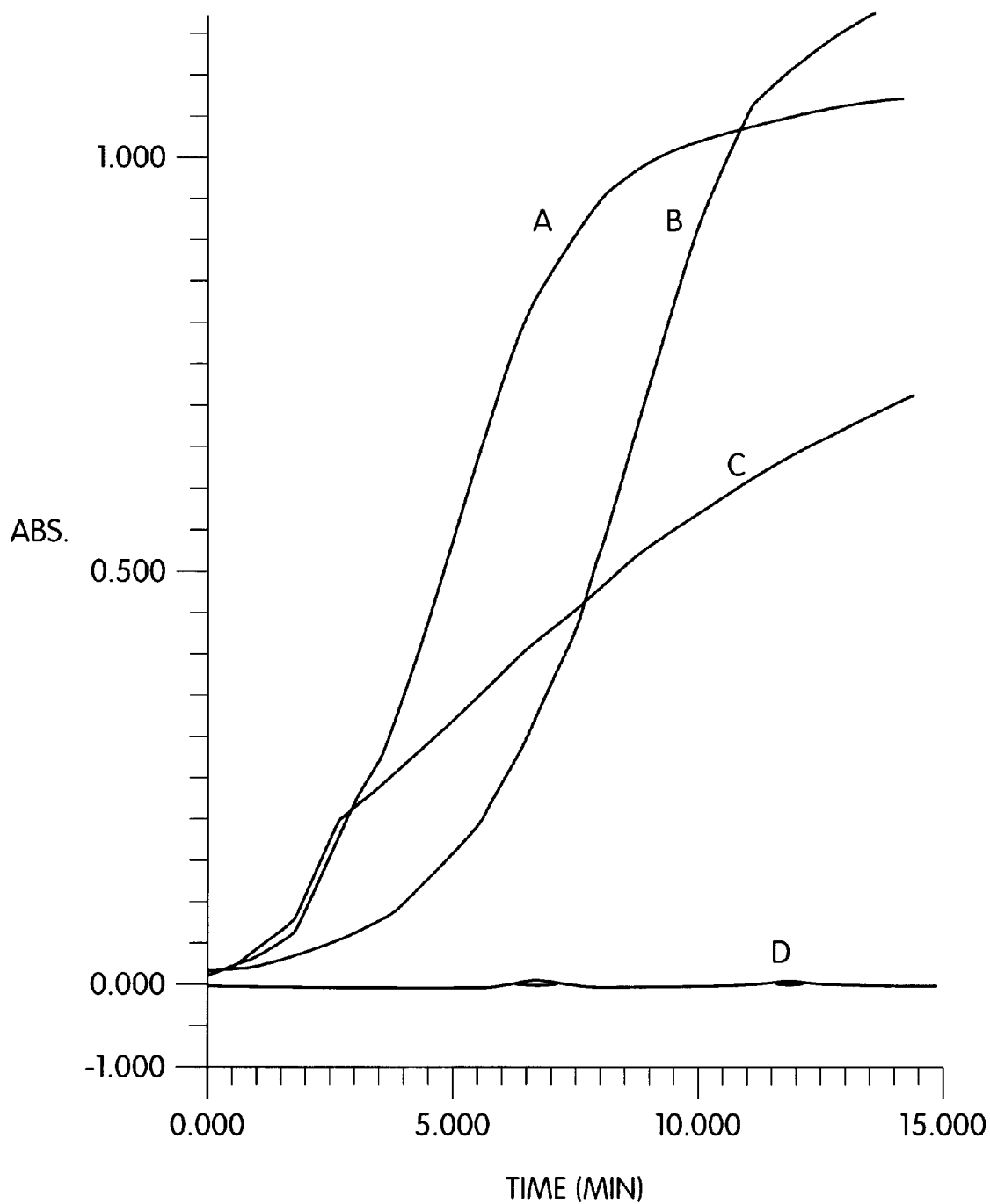
FIG. 12 is a graph showing that manganous and bicarbonate-activated recombinant *H. pylori* urease lost catalytic activity after dialysis. Recombinant *H. pylori* apourease was activated by incubation with 100 mM HEPES (pH 8.0), 0.3 M NaCl, 1 mM EDTA, 200 mM sodium bicarbonate, and either 1 mM $Ni^{++}$ (a and c) or 1 mM Manganous Chloride (b and d). Samples were incubated at 37° C. for 1 hour and immediately assayed for urease activity (a and b), or dialyzed against 2% sucrose at 4° C. overnight and then assayed for activity (c) and d). The $Mn^{++}$ ion-activated urease lost activity after dialysis. Activity was not restored by addition of $Mn^{++}$ ions, even after preincubation for several hours with $Mn^{++}$ ion before activity was assayed. The titration curves are normalized for zero time readings.

Effect of other metal ions and imidazole on activation of recombinant urease $Ni^{++}$, $Mn^{++}$, $Zn^{++}$, $Cu^{++}$, $Fe^{++}$, and $Mg^{++}$ ions were tested for their abilities to activate recombinant urease. Pre-incubation of recombinant urease with $Ni^{++}$ ions or $Mn^{++}$ ions resulted in activation of urease, as monitored by its ability to cause an increase in pH when incubated with urea in a phenol red urea broth assay (FIG. 1). Activation of recombinant urease by $Mn^{++}$ ions was also demonstrated by direct estimation of liberated ammonia using Nessler's reagent. However, $Mn^{++}$ ion-activated recombinant urease did not result in detection of a band having urease activity, as detected by native PAGE and by urease-specific silver staining. Also, while recombinant urease activated with $Ni^{++}$ ions and bicarbonate retained catalytic activity after dialysis of unbound $Ni^{++}$ ions and bicarbonate, the $Mn^{++}$ ion-activated recombinant urease lost catalytic activity after dialysis (FIG. 12). In a separate experiment, it was observed that $Li^{++}$ and $Co^{++}$ ions do not cause urease activation.

Figure 13A:
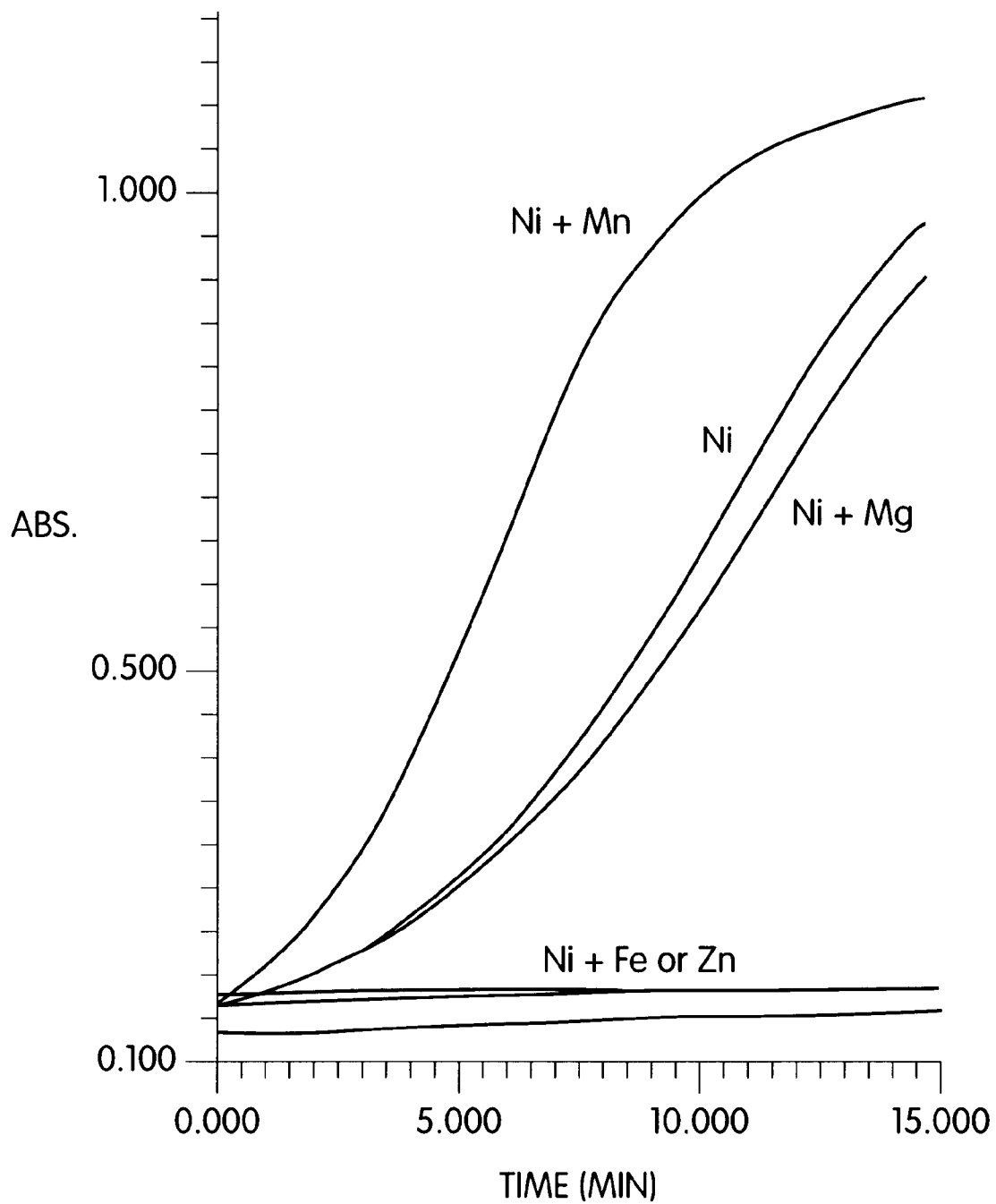
FIG. 13A is a graph showing that manganous ion has a synergistic effect and cupric, ferrous, and zinc ions have antagonistic effects on the activation of recombinant *H. pylori* apourease by nickel ions and bicarbonate. Recombinant *H. pylori* apourease was incubated with activation buffer containing 0.1 M HEPES buffer (pH 8.0), 0.3 M sodium chloride, 1 mM EDTA, 100 μM $Ni^{++}$, and 200 mM sodium bicarbonate in the absence or presence of other metal ions, as indicated in the Figure. After 2 hours of incubation at 37° C., 10 μl activated urease was added to 1 ml urea broth, and activity was followed by monitoring increases in absorbance at 550 nmn.
Figure 13B:
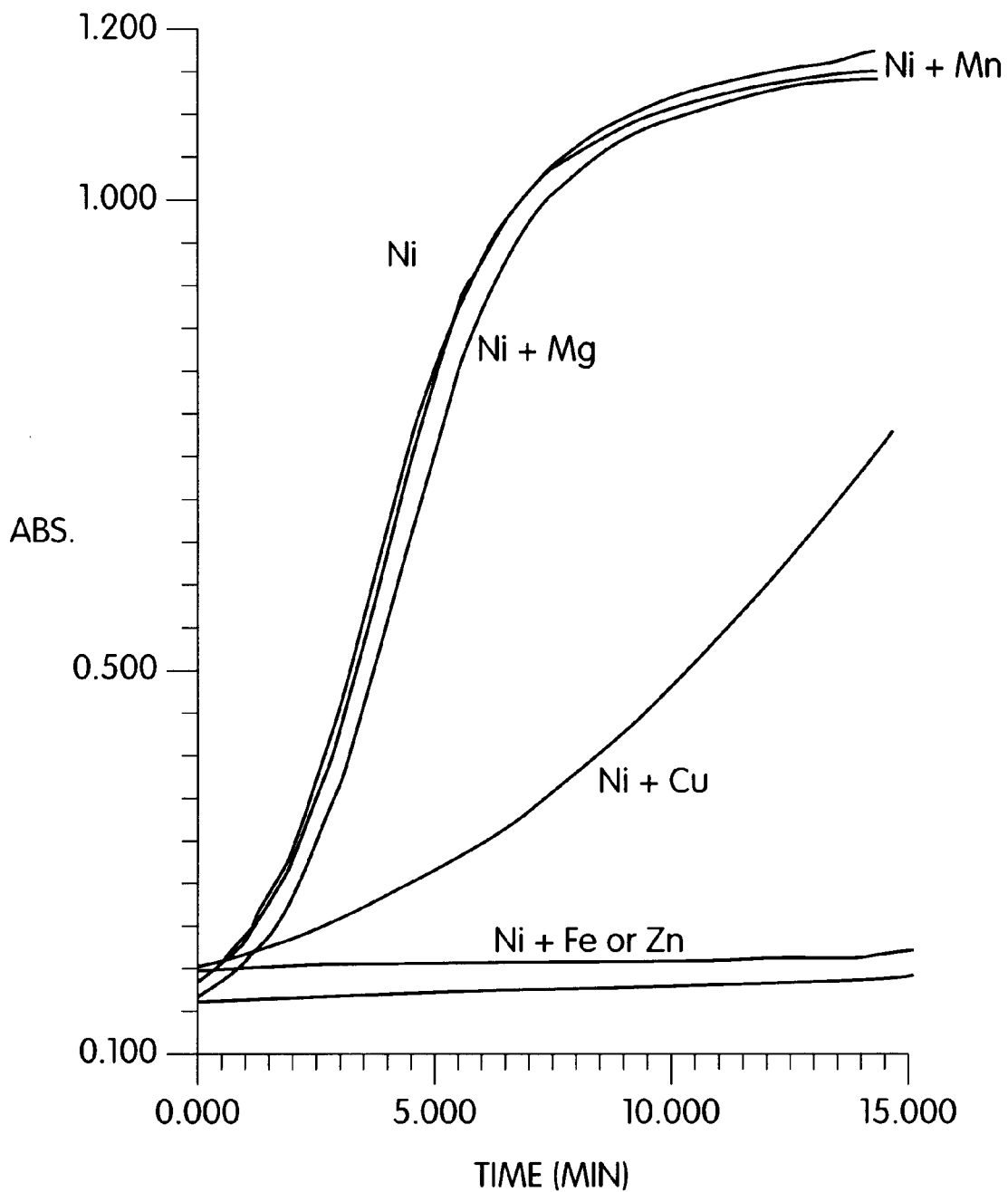
FIG. 13B is a graph showing the results of the same experiments as those described above for FIG. 13A, except that the activation buffer contained 500 μM $Ni^{++}$, rather than 100 μM $Ni^{++}$.
Figure 14:
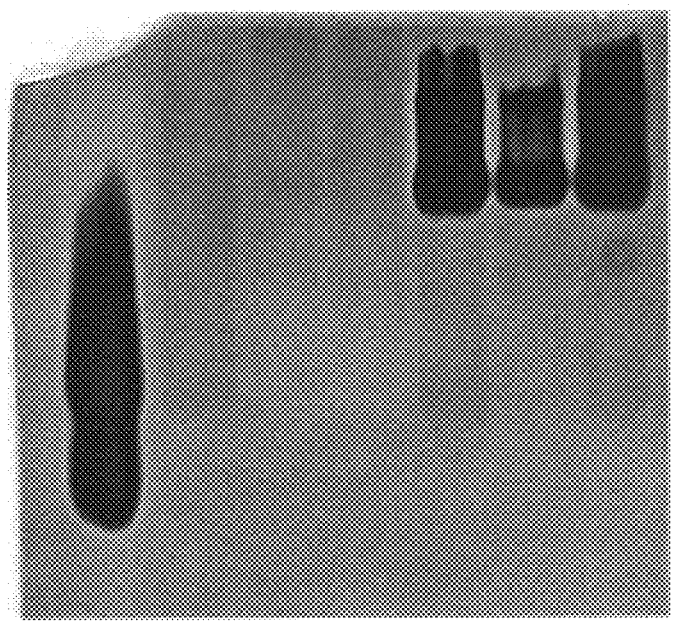
FIG. 14 is a photograph of a gel showing that use of a combination of manganous and $Ni^{++}$ ions results in a reduced amount of active urease, as determined by native PAGE and urease-specific silver staining. Recombinant urease activated under the conditions described above for FIG. 13A was stored at 4° C. overnight. The activity was monitored using the phenol red urea broth assay. The samples were mixed with an equal volume of sample buffer, separated on a 4% PAGE gel under non-reducing and non-denaturing conditions, and activity staining was performed using urease-specific staining conditions. Lane 1 contains jack bean urease, lane 2 contains sample incubated with $Cu^{++}$ and $Ni^{++}$ ions, lane 3 contains sample incubated with $Zn^{++}$ and $Ni^{++}$ ions, lane 4 contains sample incubated with $Fe^{++}$ and $Ni^{++}$ ions, lane 5 contains sample incubated with $Mg^{++}$ and $Ni^{++}$ ions, lane 6 contains sample incubated with $Mn^{++}$ and $Ni^{++}$ ions, and lane 7 contains sample incubated with $Ni^{++}$ ions.
Figure 15:
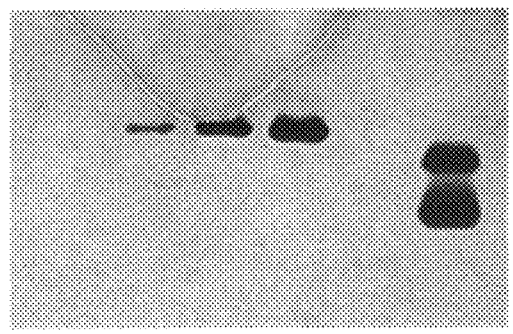
FIG. 15 is a photograph of a gel showing that imidazole inhibits urease activation by $Ni^{++}$ ions and bicarbonate. Recombinant *H. pylori* apourease was incubated at 37° C.

Combinations of $Ni^{++}$ and other metal ions were tested to see whether the other metal ions can interfere with the activation of recombinant urease by $Ni^{++}$ (FIG. 13). $Ni^{++}$ ions (0.1 mM) and 1 mM of the other metal ions were used. Under these conditions, $Mg^{++}$ ions had no detectable effect. $Mn^{++}$ ions enhanced the activation of recombinant urease, showing that there is a synergistic effect of $Ni^{++}$ and $Mn^{++}$ ions. $Cu^{++}$, $Fe^{++}$, and $Zn^{++}$ ions inhibited activation of recombinant urease by $Ni^{++}$. In a separate experiment, it was found that $Co^{++}$ ions also inhibit activation with $Ni^{++}$ and bicarbonate. The synergistic effect of $Ni^{++}$ was not detected when the pre-incubation system contained a higher concentration of $Ni^{++}$ (500 EM). Native PAGE and urease-specific silver staining of urease activated with $Ni^{++}$ and the combinations of other metal ions conformed the inhibitory effect of $Cu^{++}$, $Fe^{++}$, and $Zn^{++}$ ions on urease activation. However, the activation effect of $Mn^{++}$ was not detected by analysis of the stained gel. In contrast, the activity in the $Mn^{++}$ and $Ni^{++}$ ion-activated system was less than that of $Ni^{++}$ alone or $Ni^{++}$ and $Mg^{++}$ (FIG. 14), indicating that the fraction of urease that had $Mn^{++}$ ions in the active site had lost the activity during electrophoresis. This observation is consistent with the results obtained with $Mn^{++}$ ions. The active site of urease is known to contain a cluster of histidine residues that serve as the binding site for $Ni^{++}$. Imidazole is known to complex with $Ni^{++}$, and hence should inhibit the binding of $Ni^{++}$ to the active site of recombinant urease. Imidazole concentrations ranging from 2.5–25 mM were found to inhibit the activation of recombinant urease in a concentration-dependent manner (FIG. 15).

Effect of iodoacetamide and DTNB on activation of recombinant urease

Chemical modification of recombinant urease using iodoacetamide or 5-5'-dithio-bis-2-nitrobenzoic acid (DTNB) has a stabilizing effect on urease in solution, showing that sulfhydryl groups play a role in maintaining the molecular state of recombinant urease in solution. It was observed that recombinant urease alkylated by iodoacetamide or DTNB is not activated with $Ni^{++}$ and bicarbonate, and that including iodoacetamide or DTNB in the activation mixture also resulted in the blocking of activation. In addition, iodoacetamide or DTNB-modified urease, after removal of excess modifying agent, was also not activated (FIGS. 16A and 16B).

N-ethyl maleimide is another sulfhydryl group modification reagent. Incubation of recombinant apourease (3–4.0 mg/ml) in 20 mM Hepes buffer (pH 7.5) with 9 mM NEM at room temperature for 60 minutes resulted in blocking of the sulfhydryl groups, as determined by reactivity with the thiol-specific reagent DTNB (FIG. 17A). The modified protein was not activated by bicarbonate and nickel, while the unmodified, control urease was activated under identical conditions (FIG. 17B). After fifteen days of storage at 2–8° C., the control (unmodified apourease) was aggregated and degraded significantly, as shown by a loss of more than 50% of urease by HPLC analysis (the loss being interpreted as due to removal of aggregates during filtration of the sample through a 0.2 µm filter before HPLC), while the NEM modified urease retained its molecular integrity (FIGS. 18A and 18B).

Park et al. (Science 267:1156–1158, 1995) have proposed that carbamylation of lysine 217 in *K. aerogenes* apourease, which is in a similar location as lysine 219 in Helicobacter urease, could be involved in the mechanism of in vitro activation of urease. We have used several amino group modifying reagents to chemically modify recombinant Helicobacter apourease and we have tested the effect of such modifications on in vitro activation. For example, modification of apourease with dinitrofluorobenzene (DNFB) blocked in vitro activation (FIGS. 28A–28C).

The effect of DNFB was pH dependent, as the modification was more effective at alkaline pH (pH>7.5) than at neutral or acidic pH (FIG. 28D). This is consistent with the proposed reactivity of lysine 219. Similar inactivation of enzymatic activity was noted for an already activated urease (FIG. 28E). This result shows that modification of lysine 219 may not be the cause of in vitro activation by DNFB modification. DNFB can also react with cysteine residues and other functional residues, and this could explain the effect of DNFB on apourease and reactivated urease.

Trinitrobenzene sulfonic acid (TNBSA, 5 mM) effectively blocked apourease from being reactivated in vitro (FIG. 29). Under similar conditions, incubation of in vitro activated urease with 5 mM TNBSA did not inactivate the enzymatic activity. This observation shows that a lysyl group modification in apourease may result in blocking of in vitro activation and the group in apourease modified by TNBSA is not available in activated urease. This observation is consistent with the carbamylation of a lysine residue being involved in the mechanism for in vitro activation.

In order to obtain more evidence for the binding of $Ni^{++}$ to recombinant urease, activated urease was prepared by incubation of recombinant urease with activation buffer containing $Ni^{++}$ and bicarbonate. Excess bicarbonate and $Ni^{++}$ ions were removed by extensive dialysis against 2% sucrose. The activated urease was then concentrated using a Macrosep 100 filter centrifuge (Filtron, Inc.) to a concentration of 10 mg/ml, as determined by spectrophotometric analysis at $OD_{280}$. The absorbance spectrum of the urease was recorded in the presence and absence of β-mercaptoethanol, and in the presence of β-mercaptoethanol, two distinct absorption maxima were detected at 410–407 mn and 330–325 nm (FIGS. 19A and 19B).

Recombinant H. pylori urease was purified from E. coli carrying cloned urease structural subunit genes ureA and ureB. The recombinant protein was structurally and immunologically identical to native H. pylori urease, but had no detectable enzymatic activity. Four molecular forms of urease, designated tetrameric, hexameric, octomeric, and higher polymeric forms, were isolated from urease stored in solution. The octomeric and hexameric forms also were enzymatically inactive and showed similar immunoreactivity with a mouse anti-H. pylori urease polyclonal antibody, MPA3, and an anti-H. felis urease B monoclonal IgA, MAB71. Electron microscopic examination revealed that the different molecular forms appear as particles of different sizes. There was a decrease in the total number of free sulfhydryl groups in recombinant urease solutions stored at 4° C., as compared to freshly prepared urease. Blocking free sulfhydryl groups of recombinant urease with 5, 5'-dithiobis-(2-nitrobenzoic acid) (DTNB) or iodoacetamide was shown to reduce the molecular associations. Consistent with these observations, β-mercaptoethanol stabilized urease in the hexameric form. These results demonstrate the existence of inter-subunit disulfide linkages between different UreB subunits, UreA subunits, and UreA and UreB subunits. These results are described further, as follows.

Comparison of the properties of native and recombinant H. pylori urease

Recombinant H. pylori urease-producing E. coli strain ORV214, containing structural genes encoding UreA and UreB, was constructed in an IPTG inducible expression system (Lee et al., J. Infect. Dis. 172:161–172, 1995; Pappo et al., Infect. Immun. 63:1246–1252, 1995). The bacteria were grown in 40 or 400 liter fermentation tanks in production media containing yeast extract, tryptone, and 0.6–1.5% glycerol without antibiotics. After 16–24 hours of induction, the bacteria were harvested, washed by centrifugation, and stored at −20° C. Recombinant urease was purified from the frozen bacteria by a procedure involving bacterial lysis using a microfluidizer, clarification by centrifugation, and a purification procedure involving the use of non-adsorptive DEAE-Sepharose, ultrafiltration-diafiltration (100 kDa MW cut-off, Omega membranes, Filtron, Inc.), adsorptive DEAE-Sepharose chromatography, ultrafiltration/diafiltration, and non-adsorptive Q-Sepharose anion exchange chromatography. The urease that did not bind to the Q-Sepharose under the chromatographic conditions was buffer-exchanged into 2% sucrose.

The urease purified using the above-described protocol was visualized as 29 kDa (UreA) and 60 kDa (UreB) protein bands by Coomassie staining of a reducing SDS-PAGE gel. Densitometric scanning showed that the protein was more than 95% pure. Both the UreA and UreB subunits reacted in Western blot analysis with the mouse polyclonal antibody MPA3, which was raised against purified H. pylori urease. The mouse polyclonal antibody MPA6, which was raised against the UreB subunit of H. pylori urease, reacted with the UreB subunit, and the mouse polyclonal antibody MPA4, raised against the UreA subunit of H. pylori urease, reacted with the UreA subunit of the recombinant urease. N-terminal amino acid sequencing of the reducing SDS-PAGE-separated UreA and UreB subunits of the recombinant urease was compared with the theoretical sequence derived by translation of the sequences of the genes encoding UreA and UreB (Clayton et al., Infect. Immun. 57:623–629, 1989). There was 100% amino acid sequence identity, for the 25 residues analyzed, between the actual sequence and the predicted sequence. These results established the identity of the purified recombinant urease. The amino acid composition of recombinant urease is compared with those reported for other bacterial and plant ureases in Table 1.

Analytical size exclusion HPLC revealed that urease purified according to the above-described protocol consisted of a major peak (80–90% of the total area) with a peak retention time of 9.1–9.4 minutes under the chromatographic conditions used (FIG. 20A, chromatogram 3). The HPLC column was calibrated using calibration markers from Pharmacia-LKB. The apparent molecular weight of this peak is between 550–600 kDa. This peak was designated as the hexameric form of urease $(UreA-UreB)_6$. Another minor peak, with a retention time of 8.3–8.5 minutes, was also detected. This peak contributed 5–20% of the total area in different preparations. This form, having a molecular weight of 700 kDa, was designated as the higher molecular weight, octomeric form of urease. Both of the forms were isolated from the analytical size-exclusion HPLC and identified to be different forms of urease by SDS-PAGE, native PAGE, Coomassie staining, Western blot analysis, and ELISA using polyclonal and monoclonal anti-urease antibodies (FIG. 21).

The properties of purified recombinant urease were compared with those of H. pylori urease purified from the bacterial strain CPM 630. The native urease has a slightly lower molecular weight, as detected by analytical size exclusion HPLC (FIG. 20A, chromatogram 1). A minor, high molecular weight protein peak was detected in native urease stored in PBS (FIG. 20A, chromatogram 2). This peak was absent in freshly purified urease or urease dialyzed against PBS containing 50% glycerol and stored at −20° C. This high molecular weight component was analogous to the minor, high molecular weight urease peak seen with recombinant urease. In non-reducing SDS-PAGE, the recombinant urease, as well as the native urease stored in PBS at 4° C., showed a small amount of high molecular weight protein bands that reacted with anti-ureases antibodies. The native urease and recombinant urease were shown to have identical morphologies by electron microscopic examination (Lee et al., J. Infect. Dis. 172:161–172, 1995). Native and recombinant urease showed comparable ELISA reactivity with MPA3 and MAB71. The native PAGE and Coomassie staining, as well as the Western blot analysis with MPA3 (FIG. 20B), of native urease showed discrete high molecular weight protein bands (lanes 1 and 2), but recombinant urease (lane 3) showed more heterogeneity. In isoelectric focusing (IEF) gels, native urease migrated as a sharp protein band (FIG. 20C, lanes 1 and 2) with a pI value of 6.1–6.15. The recombinant urease had a pI value of 6.25–6.35 and appeared to be more heterogenous (FIG. 20C, lane 3). These results show that native urease and recombinant apourease lacking nickel have apparently similar physicochemical and immunochemical properties. The recombinant urease apoenzyme did not exhibit any urease enzymatic activity, and such activity was not inducible by in vitro incubation of the protein with nickel ions. Activity was induced by incubation of recombinant urease with nickel and bicarbonate.

Stability of recombinant urease under different conditions

The purified, recombinant *H. pylori* urease was stable for at least one year when freeze-dried and stored at −20° C., as evaluated by analytical size exclusion HPLC. The protein retained its molecular integrity, as determined by reducing SDS-PAGE, Coomassie staining, and densitometry, as well as by Western blot analysis using MPA3. The protein also retained immunoreactivity, as detected by ELISA analysis, using MPA3 and MAB71.

Molecular changes occurred in recombinant urease solutions stored at 4° C. under some conditions. Molecular association occurred initially. Subsequently, the solutions became turbid and the protein precipitated. After initial molecular association and precipitation, breakdown products were also detected. In 2% sucrose at 4° C., the area of the hexameric urease peak (H) decreased with time, with an increase in the area of the high molecular weight, octomeric urease (O) peak at 8.3 minutes. After a few days, the molecule started to breakdown to a low molecular weight peak, with a retention time of 10.1–10.3 minutes, corresponding to a putative pentameric or tetrameric (T) urease. A high molecular weight, soluble, polymeric form (P) that eluted in the void volume of the column (retention time of approximately 6 minutes) was also frequently detected. A chromatographic profile of a recombinant urease solution stored at 4° C. for one month is shown in FIG. 21A. Reducing SDS-PAGE and Coomassie staining showed no difference in profile between freshly prepared and stored urease solutions. Only UreA and UreB subunits were detected. However, native gel analysis showed that molecular changes took place in the course of storage. Non-reducing SDS-PAGE revealed a number of high molecular weight bands in addition to UreA and UreB subunits. In a freshly prepared sample, more than 80% of the protein was in the UreA and UreB forms, suggesting that there were little inter-subunit covalent disulfide bonds. However, in the samples stored in solution for different, longer time periods, the intensity of UreA and UreB bands decreased significantly, while the intensity of high molecular weight components increased. Those high molecular weight components reacted with anti-UreB, as well as anti-UreA, antibodies in Western blot analysis. These results showed that the high molecular weight components contain both UreA and UreB subunits held together by covalent inter-subunit disulfide bonds. The urease could also be stabilized by storage in 50% glycerol at −20° C.

Biochemical and immunochemical properties of the different forms of urease

Because different molecular forms of urease were detected by size-exclusion HPLC analysis of urease stored in solution, these forms were separated and the biochemical and immunochemical characteristics of the forms were studied by reducing SDS-PAGE (FIG. 21B), native PAGE, Western blot analysis (FIG. 21C), UV-visible absorption spectroscopy (FIG. 21D), ELISA using different anti-urease antibodies (FIG. 22A), and electron microscopy (FIG. 22B). The reducing SDS-PAGE and Coomassie staining showed that the different peaks all contain UreA and UreB subunits. Native PAGE and immunoblot analysis revealed the presence of multiple urease bands with different molecular weights (FIG. 21C). The peaks with lower retention times in HPLC showed higher proportions of high molecular weight protein bands (FIG. 21C, lane P), and peaks with higher retention times showed low molecular weight protein bands in native PAGE (FIG. 21C, lane T). These results showed that the different peaks of urease separated by HPLC represent different molecular forms of urease. The absorption spectrum of the different peaks of urease separated by HPLC is shown in FIG. 21D. While the spectral properties of the peaks with retention times of 8.3 (octomer), 9.3 (hexamer), and 10.1 (tetramer) minutes are apparently similar, the spectral properties of the higher molecular weight form that eluted in the void volume of the column was strikingly different. The absorption spectrum of the polymeric form suggests significant contribution by Raleigh light scattering. The observed spectrum of the polymeric (P) form is analogous to that reported for the polyribosyl ribitol phosphate-outer membrane protein complex from *Neisseria meningitiidis* (Mach et al., Biotechniques 15:240–242, 1993). Under all storage conditions, this peak had a higher absorption at 254 nm, compared to that at 280 nm, as evaluated from the HPLC traces and peak integration. The immunoreactivity of the four different forms with MPA3 and MAB71 were determined (FIG. 22A). The hexamer and octomer forms of recombinant urease showed apparently similar reactivities with MPA3 and MAB71. The polymeric form (P) showed much lower reactivity with both MPA3 and MAB71.

Electron micrograph of different forms recombinant urease

Electron microscopic evaluation (FIG. 22B) of octomeric (O) and hexameric (H) forms revealed that these fractions are composed of relatively pure monodispersed macromolecular particles that are 12 nm in diameter, and most of which are oriented with the central core facing up. The high molecular weight, polymeric (P) form that eluted in the void volume of the column consisted of a mixture of 12 nm macromolecular particles and randomly oriented particulate material aggregated together into thick masses that failed to disperse over the carbon surface. The tetrameric form (T) of urease consisted of finely dispersed particles of less than 10 μm and a few isolated 12 nm particles.

Effect of β-mercaptoethanol, EDTA, and Tween 20 on the stability of recombinant urease The effect of β-mercaptoethanol, EDTA, and Tween 20 on the stability of purified recombinant urease was also studied. Table 2 shows the effect of β-mercaptoethanol on the stability of purified recombinant urease, as evaluated by HPLC analysis. Dialysis of samples against PBS for 12–24 hours resulted in formation of high molecular weight forms of urease. This was evident from detection of a significant reduction in the total area of the urease peak analyzed immediately after dialysis (peak area 51), compared to the urease dialyzed in PBS containing 0.01–1 mM urease (peak area 72–80). Protein analysis by a modified Lowry method (Zak et al., Clin. Chim. Acta 6:665–670, 1961) and SDS-PAGE under reducing conditions revealed no difference in protein concentration or UreB and UreA band intensities between the samples dialyzed in PBS in the absence or presence of β-mercaptoethanol. These results show that the urease dialyzed in PBS is aggregated and is removed by the Z-spin filters used in filtering the samples for HPLC analysis. Formation of high molecular weight forms of urease upon dialysis against PBS is also supported by detection of a significant increase in the area of the high molecular weight urease peak eluting at the void volume. Inclusion of 0.01–1 mM β-mercaptoethanol in the dialysis buffer prevented the molecular associations. EDTA (1 mM) or Tween 80 (0.2%) did not have any significant effect on this. The extent of association and precipitation continued to increase with time of storage in the absence of β-mercaptoethanol. During 1 week of storage at 4° C., in the absence of β-mercaptoethanol, nearly 90% of urease was removed by filtration using the 0.2 μm Z-spin filter, as evident from the reduction in the total area (peak area 51.0 in day 1 and 5.0 in day 7). β-mercaptoethanol (0.01 mM to 1 mM) afforded significant protection against this molecular association. The presence of β-mercaptoethanol not only prevented the association of urease into different, high molecular weight forms, but it also resulted in the breakdown of some of the urease to small molecular weight components. Sucrose significantly reduced the extent of aggregation of urease, and, in the presence of sucrose, the effect of β-mercaptoethanol was marginal. The protective effect of β-mercaptoethanol can be explained by the ability of β-mercaptoethanol to prevent inter-subunit disulfide bridges between UreA and UreB. The increased breakdown of the high molecular weight forms to lower molecular weight forms can similarly be explained by the ability of β-mercaptoethanol to break intermolecular disulfide bonds between urease subunits.

Effect of DTNB treatment on the molecular state and immunochemical properties of recombinant urease These results show stabilization of recombinant urease by β-mercaptoethanol. Because instability caused by molecular association leads to inter-subunit disulfide bridges, blocking of free SH groups of urease should prevent the molecular association. To test this, DTNB was used to block the free sulfhydryl groups in the recombinant protein. The amino acid composition predicted by the nucleic acid sequences of the genes encoding UreA and UreB suggest the presence of three cysteine residues in each UreB subunit and one SH group in each UreA subunit. Thus, the nucleotide sequences of the genes encoding UreA and UreB predict the presence of four SH groups for a urease (UreA-UreB) monomeric unit. The SH groups of recombinant urease were titrated with DTNB (FIG. 23A). More than three moles of SH groups were titrated for each mole of (UreB-UreA) monomer of freshly prepared urease. This observation shows that 70–80% of the total SH groups are free and titratable with DTNB. Addition of 1% SDS to the reaction mixture resulted in enhanced reactivity of the SH groups, but the total number of SH groups titrated was the same in the presence and absence of SDS. Non-reducing SDS-PAGE analysis of a freshly prepared urease sample, followed by Coomassie staining and densitometry, revealed that 70–75% of the UreB and UreA subunits are non-covalently associated and breakdown in SDS. The remaining 20–30% were covalently associated and migrated as high molecular weight protein bands above the UreB band. This result confirms the presence of inter-subunit disulfide linkages in recombinant urease. The results from non-reducing SDS-PAGE were consistent with the DTNB titration results.

SH group reactivity decreases with time of storage

Recombinant urease solutions stored at 4° C. for different time periods showed a time-dependent reduction in titratable SH groups (FIG. 23B). Consistent with this reduction in free SH groups, there was an increase in high molecular weight protein bands as detected by non-reducing SDS-PAGE (FIG. 24B, lanes 1–3) and native PAGE (FIG. 24C, lanes 1–3), with very little change detected by reducing SDS-PAGE (FIG. 25A, lanes 1–3). The high molecular weight protein bands detected by non-reducing SDS-PAGE reacted with MPA3 (FIG. 25A), MPA4 (FIG. 25B), and MPA6 (FIG. 25C), suggesting the formation of UreA-UreB covalent associations.

Blocking the SH groups stabilizes recombinant urease by preventing molecular associations To determine the role of sulfhydryl groups on the molecular associations of urease, the free SH groups were blocked by titration with DTNB. The properties of DTNB-treated urease were compared with those of untreated controls (FIGS. 24 and 25). An analytical size exclusion HPLC profile of DTNB-treated urease is compared with those of untreated controls in FIG. 23C. Dialysis of urease in PBS under the experimental conditions resulted in a significant reduction in the area of the hexameric and octomeric urease, with a concomitant increase in the high molecular weight urease peak in the column void volume (FIG. 23C, chromatogram c). However, DTNB treatment, followed by dialysis in PBS, prevented the molecular associations (FIG. 23C, chromatogram b). In fact, the DTNB-treated sample showed a slight increase in the low molecular weight urease peak (tetrameric or pentameric urease). These results (FIGS. 24A–24C, lanes 5 and 6, FIGS. 25A–25C, lanes 3 and 4, and FIG. 23C) show that DTNB treatment stabilized the hexamer form of urease and prevented molecular association. The control urease, not treated with DTNB, but otherwise treated identically to the DTNB-treated samples, was highly polymerized. DTNB treatment did not affect the immunoreactivity of the urease, as determined by Western Blot analysis. DTNB-treated samples retained immunoreactivity with MPA3 and MAB71, as determined by ELISA analysis, but the control sample, which was treated identically, had much lower ELISA reactivity. Alkylation of recombinant urease using iodoacetamide also stabilized the hexameric form of urease and prevented molecular association.

Freshly isolated urease stored in 20 mM Tris pH 8.6 was alkylated by incubation with 1 mM iodoacetamide for 1 hour at room temperature. The resulting product was diafiltered into 2% sucrose. The alkylated and control urease were titrated with DTNB and the number of titratable SH groups for each monomeric urease was estimated. DTNB titration of freshly isolated urease showed the presence of 2.5–3.0 moles of titratable SH groups and analysis of the alkylated urease showed the presence of 0.4 titratable SH groups in the absence of SDS. In the presence of 1% SDS, the alkylated urease showed the presence of 1–1.2 moles of SH group and control urease showed the presence of nearly 3.1 moles of SH groups. These results showed that nearly three SH groups are free for every UreA-UreB complex, and, under the experimental conditions, two of the SH groups are blocked by iodoacetamide. The free SH group that was not blocked by iodoacetamide became reactive with DTNB in the presence of 1% SDS, but not in the absence of SDS.

The abbreviations used in the description set forth above are as follows: HPLC, high pressure liquid chromatography; FPLC, fast protein liquid chromatography; MPA, mouse polyclonal ascites; PBS, phosphate-buffered saline (10 mM Phosphate, 150 mM sodium chloride, pH 7.4); DTNB, 5-5'-Dithiobis-(2-Nitrobenzoic acid); PEM, 20 mM phosphate, 1 M EDTA, 1 mM β-mercaptoethanol; and CAPS, 3-[cyclohexylamino]-1-propanesulfonic acid.

TABLE 1

Amino acid composition of recombinant *H. pylori* urease compared with the amino acid compositions of native *H. pylori* urease and ureases from other sources.

| | Mole % in different ureases[c] | | | | |
|---|---|---|---|---|---|
| Amino Acid[a] | r. urease[b] | *H. pylori* urease[d] | Jack Bean urease[e] | *K. aerogenes* urease[f] | Brevibacterium ammoniagenes urease[g] |
| Asx* | 11.8(0.4) | 15.6 | 10.6 | 9.2 | 11.6 |
| Glx** | 11.1(1.2) | 11.2 | 8.2 | 10.3 | 10.2 |
| Ser | 4.5(0.1) | 5.1 | 5.6 | 6.1 | 3.6 |
| Gly | 9.5(0.3) | 11.1 | 9.4 | 12.4 | 9.7 |
| His | 3.4(0.2) | 5.6 | 3.0 | 3.0 | 2.9 |
| Arg | 3.2(0.8)*** | 3.9 | 4.5 | 4.0 | 4.9 |
| Thr | 7.2(0.4) | 6.2 | 6.6 | 6.9 | 7.2 |
| Ala | 9.4(0.5) | 9.8 | 8.6 | 10.5 | 10.7 |
| Pro | 4.1(0.1) | 3.4 | 5.0 | 5.5 | 4.7 |
| Tyr | 2.3(0.2) | 2.1 | 2.5 | 6.9 | 7.2 |
| Val | 5.8(0.2) | 6.1 | 6.6 | 7.5 | 7.8 |
| Met | 3.4(0.4) | 2.4 | 2.5 | 1.7 | 1.8 |
| Cys | | | | | |
| Ile | 6.9(0.3) | 5.9 | 7.9 | 5.7 | 7.1 |
| Leu | 6.4(0.3) | 7.4 | 8.2 | 6.6 | 7.5 |
| Phe | 3.8(0.5) | 4.1 | 2.9 | 2.6 | 3.0 |
| Lys | 7.3(0.5) | | | | |
| Try | | | | | |

[a]Cys, Lys, and Try were not detectable by the methods used.
[b]Average of 7 estimations with standard deviations in parentheses.
[c]Amino acid composition predicted from the nucleotide sequence.
[d]Data from Hu et al., Infection and Immun. 58:992–998, 1990.
[e]Data from Mamiya et al., Proc. Jpn. Acad. 61:395–398.
[f]Data from Todd et al., J. Biol. Chem. 263:5963–5967, 1987.
[g]Data from Nakano et al., Agric. Biol. Chem. 48:1495–1502, 1984.
*Represents sum of asparagine and aspartic acid.
**Represents sum of glutamine and glutamic acid.
***Very high standard deviation, between the results from runs at two different time points.

Bacterial strains and media

*H. pylori* strain ATCC 43504 (American Type Culture Collection, Rockville, Md.) was used for the production and purification of urease for the generation of immunological reagents. *H. pylori* strain CPM 630 (from Soad Tabaqchali's Laboratory, St. Bartholomew's Hospital Medical School, London) was used for production and purification of native *H. pylori* holoenzyme for comparison with recombinant urease. *H. pylori* was grown in Mueller Hinton (MH) agar (Difco Laboratories, Detroit, Mich.) containing 5% sheep red blood cells (Crane Labs, Syracuse, N.Y.) and antibiotics (5 μg/ml trimethoprim, 10 μg/ml vancomycin, and 10 U polymyxin B sulfate (TVP) per ml; Sigma Chemical Co., St. Louis, Mo.). Plates were incubated for 3–4 days at 37° C. in 7% $CO_2$ and 90% humidity.

Production and purification of urease

The expression, production, and purification of recombinant urease, as well as the purification of native *H. pylori* urease and generation of antibodies, has been described (Lee et al., J. Infect. Dis. 172:161–172, 1995; Pappo et aL, Infect. Inuun. 63. 1246–1252, 1995). Recombinant *H. pylori* urease was produced in genetically engineered *E. coli* transformed with a plasmid containing the structural genes of *H. pylori* urease. The production strain, designated ORV214, contained the structural genes encoding UreA and UreB in an isopropylthiogalactoside (IPTG)-inducible expression system (Lee et al., J. Infect. Dis. 172:161–172, 1995; Pappo et al., Infect. Immun. 63:1246–1252, 1995).

Recombinant urease was produced in large scale by growing the recombinant *E. coli* strain (ORV214) in 40–400 liter fermentation tanks. Bacteria from the fermentation systems were harvested by centrifugation. Urease was extracted by breaking the bacteria in 20 mM phosphate, 1 mM EDTA (PE) buffer, pH 6.8, by passing the bacteria through a Microfluidizer at a pressure of 13,000–19,000 psi, and clarified by centrifugation at 28,000–30,000× g in a Sorvall 6C high speed centrifuge at 4° C. The soluble urease from the extract was purified using a combination of ion-exchange chromatography on DEAE-Sepharose and Q-Sepharose (Pharmacia Biotechnology), and by an ultrafiltration diafiltration procedure.

Native *H. pylori* urease was purified using a modification of the procedure reported by Hu et al. (Infect. Immun. 58:992–998, 1990). *H. pylori* strain ATCC 43504 or CPM 630 was grown in blood agar plus TVPA plates. Bacteria

TABLE 2

Effect of β-mercaptoethanol on the stability of urease

| Condition β-mercaptoethanol | Peak area (Hexamer) | | Peak area (Octomer) | | Peak area Higher form | | Total urease peak area | |
|---|---|---|---|---|---|---|---|---|
| (mM) | Day 1 | Day 7 | Day 1 | Day 7 | Day 1 | Day 7 | Day 1 | Day 7 |
| 0.0 | 39.1 | 3.2 | 9.3 | 1.1 | 2.13 | 0.66 | 51.0 | 5.0 |
| 0.01 | 60.2 | 30.04 | 9.1 | 7.64 | 2.7 | 1.64 | 72.0 | 39.3 |
| 0.1 | 73.2 | 54.7 | 3.4 | 3.3 | 3.2 | 2.0 | 80 | 60 |
| 1.0 | 75 | 49 | 0.0 | 0.0 | 3.2 | 1.1 | 78 | 50.1 |

Purified recombinant urease (2–2.3 mg/ml) was dialyzed for 24 hours against phosphate-buffered saline, pH 7.0, containing 0, 0.01, 0.1, and 1 mM β-mercaptoethanol. The samples were analyzed immediately after dialysis and 7 days after storage at 4° C. by analytical size exclusion HPLC. Samples were pre-filtered using 0.2 μm Z-spin filters before injection into HPLC columns. The absolute peak area of different forms of urease is shown. The hexamer form(Rt = 9.2–9.4 minutes), octomer form (Rt = 8.2–8.4 minutes), and higher molecular weight form (Rt = 6.0 minutes) are evaluated.

The results set forth above were obtained using the following materials and methods.

were harvested by centrifugation (20,000× g in Sorvall 6C high speed centrifuge for 15 minutes at 4° C.), resuspended in 3 volumes of water or 20 mM phosphate, 1 mM EDTA, 1 mM β-mercaptoethanol (pH 6.8), lysed by sonication using a Branson sonifier (Ultrasonics, Danbury, Conn.) with three 15 second pulses, at 50% duty cycle and a power setting of and clarified by centrifugation (30,000× g for 45 minutes at 4° C.). The clarified supernatant was mixed with 3 M sodium chloride to a final sodium chloride concentration of 0.15 M and passed through a 1.6×10 cm DEAE-Sepharose column (Fast Flow). The fractions with urease activity that passed through the column under these conditions were collected, concentrated using a Filtron Macrosep 100 centrifugal filtration unit, and then passed through a Superose 12 (1×30 cm) or Superdex 200 (1.6×60 cm) size exclusion column. Superose 12 chromatography was performed at a sample load of 0.5 ml and a flow rate of 30 ml/hour. Superdex-200 column chromatography was performed at a sample load of 2–4 ml and a flow rate of 120 ml/hour. Size-exclusion chromatography was performed using Pharmacia prepacked columns and an FPLC system. The fractions containing urease activity were pooled, concentrated, and further purified by anion-exchange chromatography on a Mono Q-Sepharose column. Mono Q anion-exchange chromatography was performed using a prepacked (0.5×5 cm) column from Pharmacia and an FPLC system. The column was equilibrated with PEM buffer. The bound urease was eluted using a 0–1 M sodium chloride gradient in PEM buffer. The fractions with urease activity were pooled and concentrated using Macrosep 100 centrifugal filters. In cases where the purity was less than 90%, as determined by SDS-PAGE and densitometry, further purification was achieved by a final analytical size exclusion FPLC fractionation on Superose 12 columns.

Production of high titer anti-urease polyclonal mouse antibodies

Polyclonal mouse antibodies were raised against the purified *H. pylori* urease and urease subunits. The MPA3 antibody was generated using purified urease. The UreB and UreA subunits were purified by separating the subunits by SDS-PAGE and electroeluting the separated subunits from gel slices. The electroeluted proteins were used for generation of MPA4 and MPA6. The generation of MPA3 (anti-urease), MPA4 (anti-UreA), and MPA6 (anti-UreB) have been described (Lee et al., J. Infect. Dis. 172:161–172, 1995). A rabbit polyclonal antibody against purified *H. pylori* urease was generated by subcutaneous injection of purified urease (150 μg) in Freund's complete adjuvant, followed by 2 booster doses on days 27 and 45 with 150 μg purified urease in Freund's incomplete adjuvant. Serum IgG was purified by ammonium sulphate precipitation and dialysis (Lee et al., J. Infect. Dis. 172:161–172, 1995). A monoclonal hybridoma that secretes IgA recognizing the UreB subunit was produced in the laboratory of Dr. S. Czinn (Blanchard et al., Infect. Immun. 63:1394–1395, 1995). This hybridoma was prepared using *H. felis* sonicate antigens. The hybridoma was grown in serum-free and protein-free medium (Sigma).

Analytical Methods

Analytical columns (Superdex 200, Superdex 75, and Superose 12 columns) were either obtained as prepacked FPLC columns or packed in-house using Pharmacia XK series columns with adaptors and resins from Pharmacia-LKB. Analytical size exclusion HPLC columns (Progel TSK-G4000 SWxL, 7.8 mm×30 cm) and Progel SWxL guard columns were obtained from SupelCo. The chromatographic resins DEAE-Sepharose (FF) and Q-Sepharose (FF) were obtained from Pharmacia.

Analytical size exclusion HPLC of purified urease was performed using the Gold HPLC system from Beckman, Inc. The system consisted of Pump 126, Diode array UV-visible dual wavelength detector 168, and System Gold software package V711. Chromatography was performed under isocratic conditions using a Progel TSK 4000 SWxL (7 μm) column (7.8 mm×30 cm i.d.) and a GWxL guard column in 100 mM phosphate, 100 mM sodium chloride (pH 7.0) at a flow rate of 1 ml/minute, and a pressure of 450–500 psi.

Reducing SDS-PAGE was performed in 10% or 12.5% polyacrylamide gels. Non-reducing SDS-PAGE was performed using a 4–20% precast gradient gel from NOVEX (Novel Experimental Technology, San Diego, Calif.). Native-PAGE was performed using a 4% or 6% polyacrylamide gel. Densitometric scanning of Coomassie stained gels was performed using the Ultroscan XL laser densitometer from Pharmacia-LKB.

For Western blots, proteins separated on polyacrylamide gels were transferred to nitrocellulose paper, blocked with 2.5% nonfat dry milk in 50 mM Tris, 0.5 M NaCl (pH 7.5), and then incubated overnight at 4° C. with anti-urease antibodies appropriately diluted in the blocking buffer. The unbound antibodies were washed off by three minute washings with blocking buffer. The blotted papers were then incubated with alkaline-phosphatase conjugated anti-mouse IgG for 2 hours at room temperature. The unbound antibodies were washed off by three 10 minute washings with 50 mM Tris, 0.5 M NaCl and then developed using Sigmafast alkaline-phosphatase substrate (1 tablet dissolved in 10 ml water).

For N-terminal sequencing, the UreA and UreB subunits were separated by 10% reducing SDS-PAGE, transferred to a transblot PVDF membrane (BioRad) using 10 mM CAPS, 10% methanol, pH 11.0, stained using 0.1% Coomassie brilliant blue R in 50% methanol, destained using 50% methanol, washed, and air-dried. N-terminal sequencing was performed at the Molecular Biology Core facility at Dana Farber Cancer Institute, Boston, Mass. Sequencing was performed on an Applied Biosystem automated sequencer using post-liquid Technology by Edman degradation.

For analysis of total amino acid composition, the purified product was extensively dialyzed against HPLC-quality water. Aliquots of dialyzed samples were immediately transferred to hydrolysis tubes. Amino acid hydrolysis and analysis was performed at the Molecular Biology Core facility at Dana-Farber Cancer Institute, Boston, Mass. Hydrolysis was performed with 6 N HCl in vacua containing phenol for 1 hour at 110° C. and analysis was performed using an analyzer from ABI and the Pico-tag method.

For characterization of different molecular forms of urease formed during the course of storage under different conditions, the molecular forms were separated by analytical size exclusion HPLC. Different fractions were collected and analyzed by native and reducing SDS-PAGE, Coomassie blue staining, and Western blot analysis using anti-urease antibodies. The fractions corresponding to the peak positions of different molecular forms were analyzed for ELISA reactivity using the mouse polyclonal anti-urease antibody MPA3 and mouse monoclonal anti-urease IgA MAB71 in a standardized ELISA. ELISA reactivity using these antibodies was measured using a standardized urease capture ELISA (Lee et al., J. Infect. Dis. 172:161–172, 1995).

The HPLC-separated urease peaks were applied to carbon support film copper grids (Electron Microscopy Sciences, Fort Washington, Pa.), negative stained with 1% ammonium molybdate containing 0. 1% glycerol, pH 7.5, and examined with a JEM-1010 electron microscope (JEOL, Inc., Peabody, Mass.). The original magnification was 240,000×.

The total number of reactive thiol groups in urease was estimated by spectrophotometric titration at 412 nm using 5-5'-Dithio-bis-(2-Nitro benzoic acid) (DTNB). DTNB-blocked urease was prepared by incubating purified, reconstituted urease in 100 mM Tris-HCl (pH 8.0) with 0.4% DTNB. The total number of SH groups reacted were calculated using a molar extinction coefficient of 13,000 (Ellman, Arch. Biochem. Biophys. 74:443–450, 1958), as determined using a standard curve run under similar conditions using cysteine.

Stabilization of Urease by Genetic Modification

We have constructed several urease structural protein mutants in which functional residues were substituted with alanine or other nonfunctional residues. These mutants include, for example, strain ORV261, in which histidine 136 is substituted with alanine (H136A), and ORV273, in which lysine 219 is substituted with alanine (K219A). ORV273 also includes a histidine 248 to alanine (H248A) substitution, which was introduced by chance (FIG. 26D). Construction and testing of these nonactivatable mutant forms of recombinant apourease is described further, as follows.

UreA and UreB genes were obtained from Institute Pasteur's clone pILL944 (pET11a (ureA+B)). This plasmid contains an engineered NdeI site at the start codon for ureA, which minimizes the untranslated region between vector regulatory sequences and the start of ureA. The NdeI/EcoRI fragment of pILL944, containing the ureA and ureB units, was subcloned into similarly digested pET29a+ to create pORV261. The plasmid was introduced into BL21 DE3 for expression of UreA and UreB under T7 regulatory control. This strain (ORV261) was confirmed to express urease and the strain could be cultivated and urease purified from it using methods for ORV214. The nucleotide sequence for ureA and ureB was confirmed to match the published sequence. This plasmid was used as template for introduction of subsequent mutations intended for prevention of reactivation.

Specific amino acid substitutions were introduced into pORV261 via site directed mutagenesis using the Kunkel method (Kunkel et al., Methods in Enzymology 154:367, 1987; Kunkel, Proc. Natl. Acad. Sci. USA 82:488, 1985). We have constructed several mutant strains. Two of the mutant strains (ORV261-H136A and ORV261-K219A plus H248A) were cloned and characterized extensively. Recombinant *E. coli* strains expressing H136A mutant urease and K219A plus H248A double mutated urease structural genes produced urease structurally analogues to the apourease produced by ORV214. Urease purified from *E. coli* pellets were purified by similar method used for purification of apourease from ORV214 pellet. Urease purified from the mutant strains were structurally identical to the urease purified from ORV214 strain, as detected by analytical size exclusion HPLC, SDS-PAGE, and Coomassie staining, and did not exhibit urease enzymatic activity. Unlike the apourease from ORV214, the apourease from this mutant strain was not activated in vitro by incubation with bicarbonate and nickel ions. This data confirmed that mutations H136A and the double mutation K219A plus H248A resulted in prevention of in vitro activation.

The K219A plus H248A double mutant was further characterized. This mutation was confirmed in clone 273 by sequencing of mutation and fall length sequencing of the urease insert. (The attempted mutation was K219A and the H248A mutation was incidental.) Research cell bank and master and working cell banks are constructed for production of urease. Urease was purified from fermentation pellets of ORV273 working cell banks using a method similar to that used for purification ORV214 pellet. The purified urease was structurally similar to apourease produced from ORV214, was not enzymatically active, and was not activatable in vitro under conditions in which apourease from ORV214 is activated (FIGS. 26A–26D).

The apourease purified from ORV273 was tested in a mouse model for its efficacy in protecting against *H. pylori* challenge. In a comparative study using urease from ORV273 and ORV214, both induced similar immune responses and showed equal efficacies in protecting the mice from bacterial infection (FIG. 27). This observation confirms that blocking in vitro activation has no effect on the protective effect of urease against Helicobacter infection. In addition, genetically altered urease purified from strain ORV273 showed similar reactivity as wild type urease with MAB71, which is a monoclonal IgA antibody raised against UreB (Table 3). These results further show that the mutations in ORV273 do not affect the antigenicity, immunogenicity, and protective effect of urease against bacterial challenge.

TABLE 3

Comparison of the immunoreactivity of recombinant mutant urease purified from strain ORV273 with the immunoreactivity of recombinant urease purified from strain ORV273

| Recombinant Urease | Relative ELISA titer to MAb71* | Relative ELISA titer to MPA3* |
|---|---|---|
| ORV214 | 92% | 102% |
| ORV273 | 122% | 111% |

*ELISA titer is calculated from standard curves constructed using reference standard purified urease from strain ORV214. The reactivity of the urease used in standard curve is arbitrarily taken as 100% for comparison. The reactivity of urease from strain ORV273 is similar to that of the standard recombinant urease from ORV214, within the assay variability. ELISA titrations were performed using standardized urease capture ELISA, as described in analytical methods, and the values were calculated using standard protocols used in the laboratory.

What is claimed is:

1. A method of preventing activation of inactive, recombinant *Helicobacter pylori* apourease comprising reacting said apourease with a compound that modifies a sulfhydryl or lysyl residue of said apourease.

2. The method of claim 1, wherein said amino acid comprises a sulfhydryl group and said compound is a sulfhydryl-reactive compound.

3. The method of claim 2 wherein said compound is iodoacetamide (IAM) or iodoacefic acid (IAA).

4. The method of claim 2, wherein said compound is selected from the group consisting of 5-5'-dithio-bis-2-nitrobenzoic acid (DTNB), 2,2'-dithiodipyridine (DTDP), cystine, cystamine, methyl methanethiolsulfonate (MMTS), N-ethyl maleimide (NEM), dinitrofluorobenzene (DNFB), and trinitrobenzene sulfonic acid (TNBSA).

* * * * *

SEQUENCE LISTING (1) GENERAL INFORMATION:

(iii) NUMBER OF SEQUENCES: 4

(2) INFORMATION FOR SEQ ID NO:1:

(i) SEQUENCE CHARACTERISTICS:
      (A) LENGTH: 15 amino acids

```
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:1:

Glu Ala Gly Ala Ile Gly Phe Ala Ile His Glu Asp Trp Gly Thr
1               5                   10                  15

(2) INFORMATION FOR SEQ ID NO:2:

(i) SEQUENCE CHARACTERISTICS:
            (A) LENGTH: 45 base pairs
            (B) TYPE: nucleic acid
            (C) STRANDEDNESS: single
            (D) TOPOLOGY: linear (ii) MOLECULE TYPE: Genomic DNA (xi) SEQUENCE DESCRIPTION: SEQ ID NO:2:

GAAGCCGGTG CGATTGGCTT TGCAATTCAC GAAGACTGGG GCACC                    45

(2) INFORMATION FOR SEQ ID NO:3:

(i) SEQUENCE CHARACTERISTICS:
            (A) LENGTH: 9 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:3:

Gln Val Ala Ile Ala Thr Asp Thr Leu
1               5

(2) INFORMATION FOR SEQ ID NO:4:

(i) SEQUENCE CHARACTERISTICS:
            (A) LENGTH: 27 base pairs
            (B) TYPE: nucleic acid
            (C) STRANDEDNESS: single
            (D) TOPOLOGY: linear (ii) MOLECULE TYPE: Genomic DNA (xi) SEQUENCE DESCRIPTION: SEQ ID NO:4:

CAAGTCGCTA TCGCCACAGA CACTTTG                                        27
```